(12) United States Patent
Nielsen et al.

(10) Patent No.: US 7,767,884 B2
(45) Date of Patent: Aug. 3, 2010

(54) METHOD OF REPRESSING FLOWERING IN A PLANT

(75) Inventors: Klaus K. Nielsen, Copenhagen NV (DK); Christian Sig Jensen, Ferderiksberg (DK); Caixa Gao, Solroad Strand (DK); Klaus Salchert, Gernrode (DE)

(73) Assignee: DLF-Trifolium A/S, Store Heddinge (DK)

( * ) Notice: Subject to any disclaimer, the term of this patent is extended or adjusted under 35 U.S.C. 154(b) by 445 days.

(21) Appl. No.: 10/507,355

(22) PCT Filed: Mar. 10, 2003

(86) PCT No.: PCT/EP03/02629

§ 371 (c)(1), (2), (4) Date: Jun. 9, 2005

(87) PCT Pub. No.: WO03/076612

PCT Pub. Date: Sep. 18, 2003

(65) Prior Publication Data

US 2006/0070141 A1 Mar. 30, 2006

Related U.S. Application Data

(60) Provisional application No. 60/363,125, filed on Mar. 11, 2002.

(51) Int. Cl.
*C12N 15/82* (2006.01)
*A01H 5/00* (2006.01)

(52) U.S. Cl. ............ 800/298; 800/278; 800/290; 800/287; 800/312; 800/320; 800/318; 800/309

(58) Field of Classification Search ........... 800/278, 800/290, 298, 287, 306
See application file for complete search history.

(56) References Cited

U.S. PATENT DOCUMENTS 7,538,260 B2    5/2009  Demmer et al.
2002/0029395 A1*  3/2002  Weigel et al. ............... 800/290

FOREIGN PATENT DOCUMENTS

| WO | WO 97/10339 A | 3/1997 |
| WO | WO 02/14524 A | 2/2002 |
| WO | WO 02/33091 A | 4/2002 |

OTHER PUBLICATIONS

Bowie et al, Science 247:1306-1310, 1990.*
McConnell et al, Nature 411 (6838):709-713, 2001.*
Ratcliffe et al (1998, Development 125:1609-1615).*
Jensen et al (2001, Plant Physiology 125:1517-1528).*
Jensen, Christian S et al: "A Terminal Flower1-like gene from perennial ryegrass involved in floral transition and axillary meristem identity." Plant Physiology (Rockville), vol. 125, No. 3, Mar. 2001, pp. 1517-1528.
Page 1526, col. 1, paragraph 2 -& Database EMBL 'Online! Nov. 13, 2000 Jensen and Nielsen: "L. perenne terminal flower 1-like protein (TFL1) mRNA, complete cds" retrieved from EBI.
Database accession No. AF316419 XP002250087 abstract -& Database EMBL 'Online! Mar. 1, 2001 Jensen et al.: "Terminal flower 1-like protein" retrieved from EBI Database accession No. Q9FUA6 XP002250088 abstract.
Ohshima S et al: "Cloning and molecular analysis of the Arabidopsis gene Terminal Flower 1." Molecular & General Genetics, vol. 254, No. 2, 1997, pp. 186-194.

* cited by examiner

*Primary Examiner*—Stuart F. Baum
(74) *Attorney, Agent, or Firm*—Birch, Stewart, Kolasch & Birch, LLP

(57) ABSTRACT

The isolation and function of a plant LpTFL1 from *Lolium perenne* (perennial ryegrass) are described, along with generation of transgenic *Arabidopsis* ryegrass, and red fescue plants. The gene prevents or represses flowering of transgenic plants. Methods for using the gene to repress or prevent flowering are described.

35 Claims, 14 Drawing Sheets

FIGURE 1
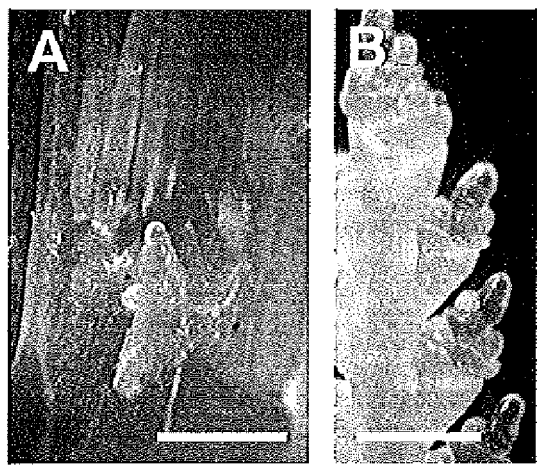
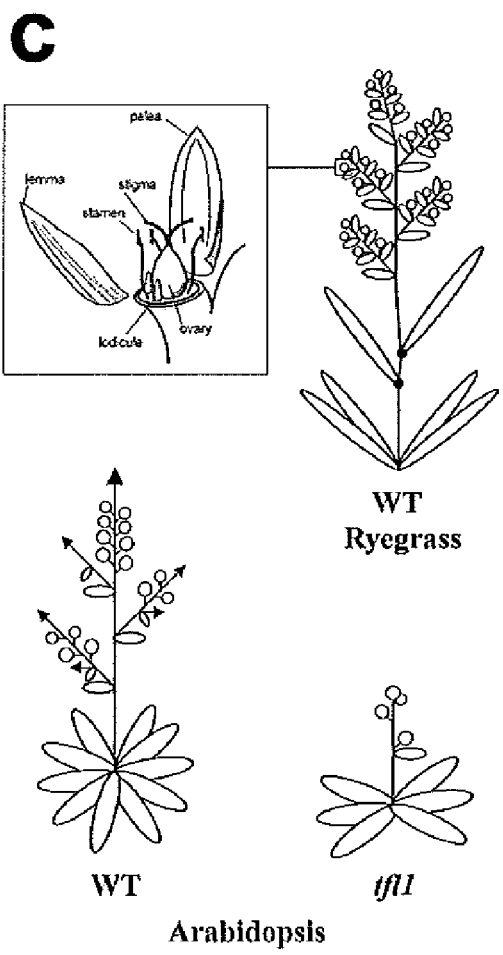
WT
Ryegrass
WT     *tfl1*
Arabidopsis

FIGURE 2

```
                                                                              GCC    -76
 -75  CAAGCCACTTCAAAGCTTTGCTACTACCAGATAGAGCATTCACCGTGCAATATAGAAATACTTGCCTCTCCAACC    -1
   1  ATGTCTAGGTCTGTGGAGCCTCTTATTGTTGGTCGTGTCATTGGAGAAGTTCTCGATCCATTTAACCCATGTGTG    75
  76  AAGATGGTAGCAACCTATAACTCAAACAAGCTGGTCTTCAATGGTCATGAGCTCTACCCATCAGCAGTTGTATCT   150
 151  AAACCAAGAGTAGAGGTTCAGGGGGGTGACTTGCGATCCTTATTCACATTGGTTATGACGGACCCAGATGTGCCA   225
 226  GGACCAAGTGATCCGTATCTGCGGGAGCATCTTCACTGGATTGTCAGTAATATACCTGGGACAACAGATGCTTCA   300
 301  TTTGGGGGGAGGTCATGAGCTATGAGAGCCCAAAGCCCAACATTGGAATCCACAGGTTCATTTTTGTGCTCTTC   375
 375  AACCACAAGCCAACGGACACTGTATCTGTCCCTTCCTTCAGCGATCATTTCAACACCCGCCACTTTGCTGTCGAT   450
 451  AATGATCTTGGCCTCCCTGTGGCTGCTGTTTACTTCAATTGTCAGAGAGAGACTGCTGCCAGGAGGCGCTGAAAA   525
 526  TCGAGTTCTTGGCTATCCCAGTTGTGCCAAATAAAGGCTTTTGGAGTTATGCACCTTCTTTCTGAAGTCAATGCT   600
 601  CCTCTTCTACATTACTTCCTCGTGGACCATTGCTTCTTTACTACAGTTTTTGCTCAGGGATCAAATAAATCAAGT   675
 675  GCATTTTGGAGATTGTATTAGATTATATTGTAAGCAGTGAGATCAGCAACCATGTGTTAACATAAGCCAGTACAT   750
 751  TAGCAGGTCCATGTTTATGGTTTCATGTTGTGTGTAAGCAGTTATCACTAGAAGGAAGGTCAGGTAGACAACCCA   825
 826  AACTGGCAAAAAAAAACCTTTATCTA                                                  851
```

FIGURE 3A

```
-3600   cactagtaacggccgccagtgtgctggaattcagggtaatacgactcactatagggmgctcgaggatcttccac   -3526
-3525   cagtgtgcattcatgtgttacttaccactctccaacttgagggactcaagattggtgggcggctccttttcgctg   -3451
-3450   aagcgatccaaaggtgtcgggtaacggttatgacagcaaacagaaaacatcgccatctgcacggaagccagaagt   -3376
-3375   agttactatgtcaaagggatataaaaaactcactaatgaaggggatgctattgctgagataaactgctatctca   -3301
-3300   tctacaggtgagattgcaagtatacttgacaacagggccagatggtatggcatgaagaaaattagggctggagta   -3226
-3225   gaaaggtaagatatgcatggatttggatgagatggctagaggggttgcgagatatcaaatagaagacocttcttca   -3151
-3150   atgattcaatagaagatgcatgtgccattacagagtggattattatgtcctttttaaagagatgcttacgtccct   -3076
-3075   gacctttcctataacacaattactactccctttgctagacttttcctgctataattgtcttttcctcgccaaaagaat   -3001
-3000   aatactatagaacttcctaatttaatttccctttattttcttggactctatcttaattctcctcctattgttcag   -2926
-2925   ccaaggactgctccttccatttacttgcgccacgggctgactgacaatgacacctgcgcgctttgtgatcaagag   -2851
-2850   cctgaatctatttctcacctcatgctgcaatgctccttctcacagcaaatatggtatgatatctgcagtaagctc   -2776
-2775   aaccttctgccatgtatgccagttggcaacgccgagttcagcatttggttcgccgcagctgccgccaacgctcaa   -2701
-2700   ccagccctgcagaagggtgctaaatccatcatcatccttactctctggagattatggaagacgaggaacgatgct   -2626
-2625   atcttcaaaaatctggccccaacagactcgccttagttcagtcgatcctagatgaagcctgtcaatggtcgtta   -2551
-2550   gccggtgctaaggcgctacgtcagttacctttacatgctagaccccctgatgttagccttgatgaggaactctag   -2476
-2475   gtctaactaagttagccctgtacagttttttttttctcttttcctttttcttttttgctttctcttcttttcgtt   -2401
-2400   tttggtagctttgctactcttgtatgctcccgtcttctcgacggcttcttctaatatataatgacgcatgctttg   -2326
-2325   gcatgtgttcgagaaaaaaatttacttacctcttaggctatattctcttcaccaacttggactccacaaagcttc   -2251
-2250   aatcgcaacttgtccaagctgctgccgctggtgctgctgtcctttccaatgcatccatacactgtcctagtcag   -2176
-2175   cataccaaacaaaaaagctaatgccgccoctgttgtttcaaatgaattatctgattgtgatgctgctaatcttttt   -2101
-2100   gcatatgagtctcgggcatatgaatgaacttggtttggcagaatgaaacaagagaggacttcttgatggatatag   -2026
-2025   cactggtaagctgaagttctgtgagcaggctatgatgttccctgttaaaaaaaaggctatgaaaacttgtgat    -1951
-1950   aggtgttaagtattggtttttattttgcgtgcaaattggtatgcatggaaagttgtagtgctactagtctgtggtg   -1876
-1875   ctactgtgctaccaacacactgtagcactgccaaaaatttatgaaaaagtctgaacagacgagatgtatctatca   -1801
-1800   attcatgaccccatttttgttataattttctttttaaaataaaaaattccgtaaagaatcaataagtggaattattg   -1726
-1725   gaaatgaaaaaagtaaccaaaatactaaactttttttttcaaatacagatcggatatcatggagacacactggctac   -1651
-1650   cattggttggaatagctactagattccactacagctaggtgtcaagcaactataatggcatcagaatggagcaga   -1576
-1575   aaaatgtcacaagctgtacttcactccactacttctagctgcacaaatgtcaagcaggcatgattgcactagacc   -1501
-1500   agaacatagtaatgcataaagctgtaattggctccactacttatggaaacgaagaaatctattatttattgtttt   -1426
-1425   aatcgagatgaagctgtgataattttatcgctgaaatgacatttcagcactagacagcaccctagacaattaagt   -1351
-1350   ggtggtggcactgtattccattccttattctcttccatggtgtgttcccatagtactacaaagaagagaataaa   -1276
-1275   cagataataatggtaatgcacttgggtatcgaagtttttaggaaagattctaattctagagcaattgaactcaaca   -1201
-1200   acaacttcccttttccttaacagaaaaagaatcggtcaaacgaggcttgcctaaaccaacaacactataaagacg   -1126
-1125   aacatttgagggtgaagaggcttccacgtgtgacagtgccgcatgtttctgtccactagataacacctaaataata   -1051
-1050   gttaaaaaacaagaggataagaatatcagaaagccagaccttaaatttctgcaagcaaacatcaaatgaagtatg    -976
 -975   caaaaacgaattgatagtttaggaaagcatcactccaaagtgtttttattcccgttcttttttcatttgctccacaa    -901
 -900   gggcatacttcctaaatttctgcgaacaattacatctagatcttttttaaaactgaagtattttagcatgaaaacg    -826
 -825   cattgttctgtaatgtggctgtgaatttcggactgctcatctgatttccctctggtagaatacataaataattat    -751
 -750   acacaacagcatgataatgtgcaaaactaagcatcaaaatctgcacattgtcatgcagaaactaggacaggagga    -676
 -675   ccagcactttgtcgtttgtcctaaccaatattaacatagttcagcaacataatcttcagagacccactagcatga    -601
 -600   aggtgtgttatgtttcctaaagaaataacatgtaggtagtgatctacaatacctttttggggactataagtgg     -526
 -525   gaaaccatcaacttgaaaaggtttccatttaatcaagtaaaaaaaacagtatttttttaactatcaataactaaaa    -451
 -450   ttaaaacagaatagagatatactaacaatgaaaatcaaacagttgtgcaaattgtatttatcgtagttagtatct    -376
 -375   catgttctggtgaaaaaattctctgccccctagaacttggaagaagatgcatgaagtattactccaaactccaac    -301
 -300   actgtgcaactgatagaaaagaaacaagaccttggttggctgtctcggaaaaagtggttaggtcctttctgtgg     -226
 -225   ccttttcagttctttccacgcataccaaccaaaaaagaacacagatactactcatgtctcacattctcttttga    -151
 -150   gcttacactcgaagcaggcttcttgcctctataagtagaggctcgtcgtactctagcaatgctcagtaagcaGCC    -76
  -75   CAAGCCACTTCAAAGCTTTGCTACTACCAGATAGAGCATTCACCGTGCAATATAGAAATACTTGCCTCTCCAACC    -1
    1   ATGTCTAGGTCTGTGGAGCCTCTTATTGTTGGTCGTGTCATTGGAGAAGTTCTCGATCCATTTAACCCATGTGTG     75
   76   AAGATGGTAGCAACCTATAACTCAAACAAGCTGGTCTTCAATGGTCATGAGCTCTACCCATCAGCAGTTGTATCT    150
  151   AAACCAAGAGTAGAGGTTCAGGGGGGTGACTTGCGATCCTTATTCACATTGGtagaatgcactcgactcgatctt    225
  226   ggaactccatattcaacttcgagtattgtatgcttgttttcttcttttcgcagtggccctaattattcatatttca    300
  301   gGTTATGACGGACCCAGATGTGCCAGGACCAAGTGATCCGTATCTGCGGGAGCATCTTCACTGGtaacctttctc    375
  375   atgcacagttttttctgctgggtggctactaagcacctaaatatattagtatattttttttgaaaggaaaatatat    450
```

FIGURE 3B

```
 451  tagtatatgttgctaaggaatatagaagtacatcttcttcttgcacatatatagacagagagactattttaatag   525
 526  cacttctaacgagagtcatttaccaatacctttttacacttacacaggATTGTCAGTAATATACCTGGGACAACAG   600
 601  ATGCTTCATTTGGtaggtccttctctgagatttgaattggtatattctatgttctgcatttttgaatgaataacca   675
 675  ctgaccttttgaattgcaggGGGGGAGGTCATGAGCTATGAGAGCCCAAAGCCCAACATTGGAATCCACAGGTTC   750
 751  ATTTTTGTGCTCTTCAAGCAGAAGCGAAGGCAGACTGTATCTGTGCCTTCCTTCAGGGATCATTTCAACACCCGC   825
 826  CAGTTTGCTGTGGATAATGATCTTGGCCTCCCTGTGGCTGCTGTTTACTTCAATTGTCAGAGAGAGACTGCTGCC   900
 901  AGGAGGCGCTGAAAATCGAGTTCTTGGCTATCCCAGTTGTGCCAAATAAAGGCTTTTGGAGTTATGCACCTTCTT   975
 976  TCTGAAGTCAATGCTCCTCTTCTACATTACTTCCTCGTGGACCATTGCTTCTTTACTACAGTTTTTGCTCAGGGA  1050
1051  TCAAATAAATCAAGTGCATTTTGGAGATTGTATTAGATTATATTGTAAGCAGTGAGATCAGCAACCATGTGTTAA  1125
1126  CATAAGCCAGTACATTAGCAGGTCCATGTTTATGGTTTCATGTTGTGTGTAAGCAGTTATCACTAGAAGGAAGGT  1200
1201  CAGGTAGACAACCCAAACTGGCAAAAAAAAAAGCTTTATCTActgtatggcccttgccggcttgatgttccatgc  1275
1276  acctttctgacatgctgtctactgtatgccaccgccactataatgtatgagatatgaatataaaatggagatat  1350
1351  ccaaaatatccagatgattgcccactaaatgctaaatgtacatagtgggttttccacctatttttgacttcatcat  1425
1426  gtccttacacaaaatcagaaaacatccatttcatgcacattgatgcacactgcatattaacaatctattcagatt  1500
1501  tggctgtaaacacaccttattttccgcatccattaatattatattagtaccctggacaggttaagcttttgcag  1575
1576  cacagtaagtaaccggatgaaattacaatatgatcctcgagcgcctat                              1624
```

FIGURE 4

```
  1  MSRSVEPLIVGRVIGEVLDPFNPCVKMVATYNSNKLVFNGHELYPSAVVSKPRVEVQGGDLRSLFTLVMTDPDVP   75
 76  GPSDPYLREHLHWIVSNIPGTTDASFGGEVMSYESPKPNIGIHRFIFVLFKQKRRQTVSVPSFRDHFNTRQFAVD  150
151  NDLGLPVAAVYFNCQRETAARRR                                                     173
```

FIGURE 5
A
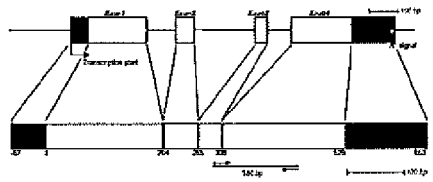
B
C
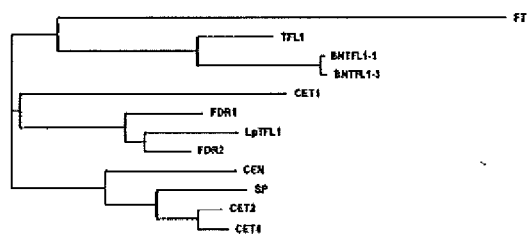

| FIGURE 15: | Transformation Efficiency and Floral Activity of the Transformants | | | |
|---|---|---|---|---|
| Cultivar | Line No. | Inflorescences | PCR | RT-PCR |
| F6 | CON | 8 | - | - |
| F6 | 7 | 18 | - | - |
| F6 | 8 | 11 | - | - |
| F6 | 17 | 5,3 | + | - |
| F6 | 18 | 13,3 | + | - |
| F6 | 24 | 12 | + | + |
| F6 | 29 | 0 | + | + |
| F6 | 32 | 0 | + | + |
| F6 | 33 | 4 | + | + |
| F6 | 36 | 0 | + | + |
| ACTION | 2 | 1,8 | - | - |
| ACTION | 5 | 3 | - | - |
| ACTION | 9 | 0,3 | - | - |
| ACTION | 12 | 2 | - | - |
| ACTION | 13 | 0 | - | - |
| ACTION | 16 | 0 | + | - |
| ACTION | 19 | 7,3 | + | - |
| ACTION | 21 | 4 | + | + |
| ACTION | 22 | 0,3 | + | + |
| ACTION | 23 | 0 | + | + |
| ACTION | 25 | 0,3 | + | + |
| ACTION | 27 | 0 | + | + |
| ACTION | 28 | 4 | + | + |
| ACTION | 31 | 0 | + | + |
| ACTION | 34 | 0 | + | + |
| ACTION | 35 | 0 | + | + |
| TELSTAR | 1 | 10 | - | - |
| TELSTAR | 3 | 1 | - | - |
| TELSTAR | 4 | 11,6 | - | - |
| TELSTAR | 6 | 10,8 | - | - |
| TELSTAR | 10 | 5 | - | - |
| TELSTAR | 11 | 3,8 | - | - |
| TELSTAR | 14 | 0 | - | - |
| TELSTAR | 15 | 3,8 | + | - |
| TELSTAR | 20 | 3,5 | + | - |
| TELSTAR | 26 | 0 | + | + |
| TELSTAR | 30 | 3,7 | + | + |

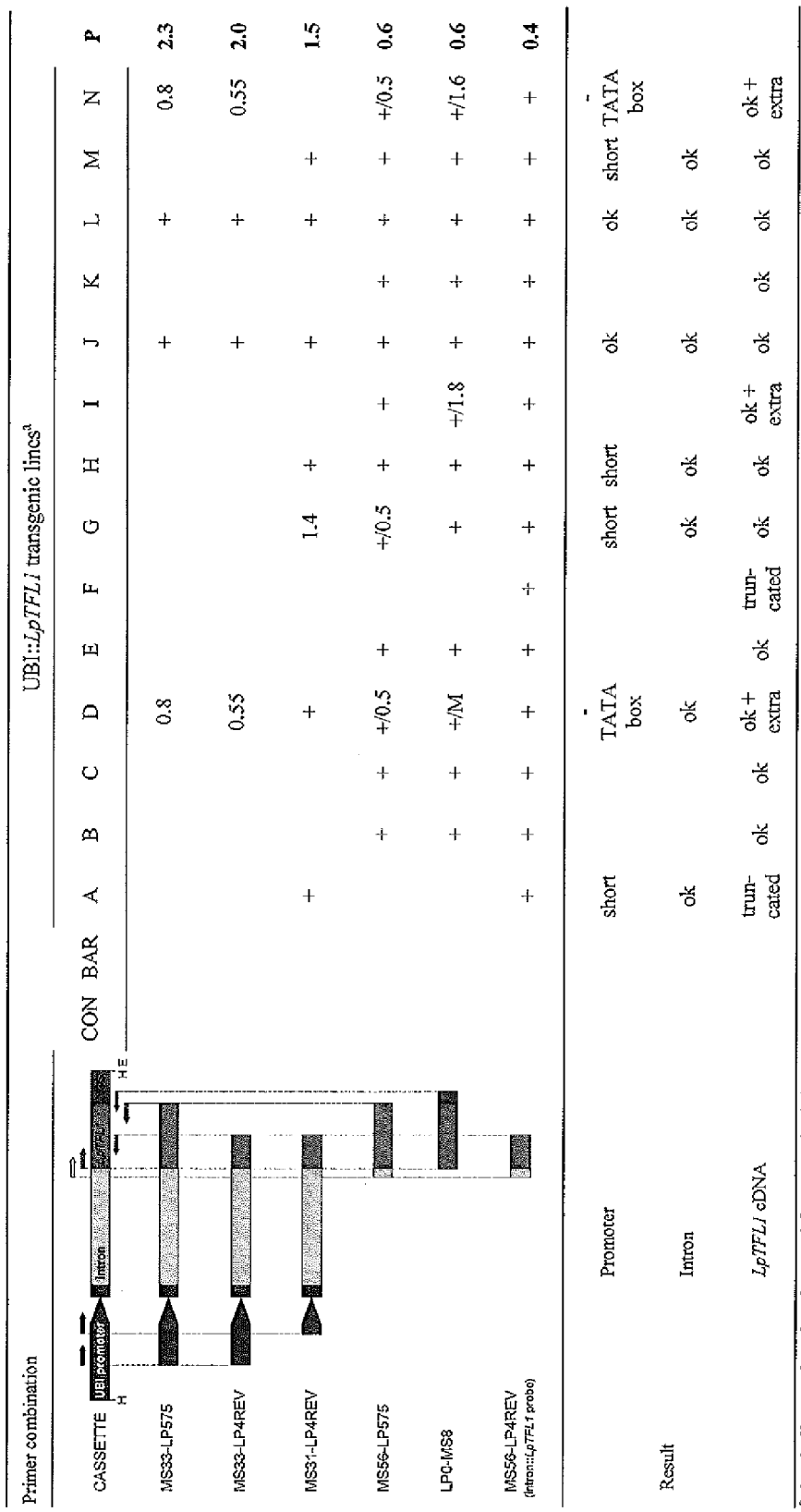
Figure 16: Transgene integration analysis by PCR using different primer combinations

METHOD OF REPRESSING FLOWERING IN A PLANT

This Application is the National Phase Under 35 U.S.C. §371 of PCT International Application No. PCT/EP2003/02629 which has an International filing date of Mar. 10, 2003, which claims priority to U.S. Provisional Application No. 60/363,125 filed on Mar. 11, 2002.

FIELD OF INVENTION

The present invention relates in part to a method of reducing or substantially preventing flowering in a plant, the method comprising expressing a newly identified flowering repressor sequence in the plant to produce a polypeptide which represses flowering in said plant. More particularly the invention relates amongst other things to the provision of vectors, cells or transgenic plants comprising said sequences or related sequences and uses thereof, and a promoter for up-regulating gene expression in the apex and leaves during long day treatment. In certain aspects of the invention, the plant may be a perennial or biennial plant; in certain further aspects of the invention, the plant may be a monocotyledonous plant.

BACKGROUND TO THE INVENTION

The life cycle of flowering plants in general can be divided into three growth phases: vegetative, inflorescence, and floral (Poethig 1990). In the vegetative phase, the shoot apical meristem (SAM) generates leaves that will later ensure the resources necessary to produce fertile offspring. Upon receiving the appropriate environmental and developmental signals, the plant switches to floral, or reproductive, growth and the SAM enters the inflorescence phase ($I_1$) and gives rise to an inflorescence with flower primordia. During this phase, the fate of the SAM and the secondary shoots that arise in the axils of the leaves is determined by a set of meristem identity genes, some of which prevent and some of which promote the development of floral meristems. Two basic types of inflorescences have been identified in plants: determinate and indeterminate (Weberling, 1989). In determinate species, such as ryegrass, the SAM eventually produces floral organs and the production of meristems is terminated with a flower. The SAM of indeterminate species is not converted to a floral identity and will therefore only produce floral meristems from its periphery, resulting in a continuous growth pattern.

The regulation of meristem identity and floral transition has been investigated in a number of dicotyledonous plants including Arabidopsis, Antirrhinum, tomato, and tobacco. However, in agronomically important seed crops such as wheat, barley, rice, forage grasses, and other monocotyledonous plants, information on how floral transition is controlled is still limited. The present inventors have undertaken a molecular investigation of the regulation of meristem identity and the control of floral transition in perennial ryegrass Lolium perenne), a cool-season perennial forage grass native to Europe, temperate Asia, and North Africa.

There are several reasons for such an investigation. Firstly the production of culm (stem) and seed head (inflorescence) formation decreases the feeding value of forage grasses. The leaf blades are more digestible, richer in crude protein and poorer in cell-wall constituents than sheaths and culms (Deinum and Dirvan, 1975; Wilman et al., 1976). The ageing of grasses is associated with an increase In lignification and a decrease in digestibility, which is markedly higher for the stems than for the leaves (Delagarde et al., 2000). Feeding trials on cows have documented that increasing the digestibility of forage grass leads to a daily increase in feed uptake and milk production (Oba and Allen, 1999). Secondly, maintenance of a vegetative forage grass requires a frequent mechanical defoliation system, which is both costly and time consuming. Too intensive defoliation can severely decrease the photosynthetic capacity of the plant and in the worst case destroy the regeneration capacity. Thirdly, flowering in many plants is associated with an uncontrollable gene flow from cultivated to wild species via the active spread of pollen. Fourthly, flowering in many perennial plants is also associated with an exposure of grass pollen allergens. A grass cultivar with an extended vegetative growth associated with decreased or even eliminated inflorescence production would thus be agronomically attractive.

In terms of plant development, the aerial parts of ryegrass are produced by the apex positioned on the base crown a few millimeters above the ground and surrounded by developing leaves (FIG. 1A). During vegetative growth the apical meristem generates lateral meristems initially recognised as semicircular ridges along the main axis. These become the leaf primordia. This morphological pattern does not change until the apex has been induced to flower by elevated temperatures and increasing day length. Flowering in perennial ryegrass is induced by a vernalization period of 12 to 14 weeks below 5° C. followed by secondary induction with long-day photoperiods (generally, more daylight hours than dark hours and, in particular, LD, 16 h of light, 8 h of darkness) and temperatures above 15 to 20° C. Upon transition to reproductive growth, the apical meristem and later also the lateral meristems start to expand and eventually turn into groups of inflorescences (spikelets), each containing three to 10 floral meristems. The flowers of the ryegrass inflorescence are arranged in a cymose, always terminating apical growth with the production of a terminal flower. In this way ryegrass represents a determinate plant architecture also seen and described at the molecular level in dicot plants such as tobacco (Amaya et al., 1999) and tomato (Pnueli et al., 1998).

In contrast to plants such as Arabidopsis and Antirrhinum, ryegrass has a determinate (cymose) inflorescence. The TERMINAL FLOWER 1 (TFL1) gene of Arabidopsis and its homolog CENTRORADIALIS (CEN) in Antirrhinum have been identified as a group of genes that specify an indeterminate identity of inflorescence meristems. Mutations in TFL1/CEN result in the conversion of the inflorescence into a terminal flower (Shannon and Meeks-Wagner, 1991; Alvarez et al., 1992;). In addition to its effect on meristem fate, TFL1 also extends the vegetative phase of Arabidopsis (Shanon and Meeks-Wagner, 1991, Ratcliff et al., 1998), but CEN does not seem to have a flowering time role in Antirrhinum (Bradley et al., 1996). CEN and TFL1 proteins have sequence similarity with mammalian phosphatidylethanolamine-binding proteins (PEBPs). The FLOWERING LOCUS T (FT) gene also belongs to the family of plant PEBP genes, but has been shown to play an opposite role to TFL1 in mediating flower inducing signals in Arabidopsis (Kardailsky et al., 1999; Kobayashi et al., 1999). Therefore the family of plant PEBP genes comprise a number of homologues proteins with different properties in relation to floral control. These differences are further revealed by the expression of different plant PEBPs from a constitutive promoter in different plant species. Expression of the TFL1 gene in tobacco from the 35S CaMV constitutive promoter, for example, does not affect the flowering time and does not affect the plant architecture of tobacco (Amaya et al., 1999).

The differences in gene function are also reflected in the different expression patterns by plant PEBPs. In Arabidopsis and *Antirrhinum*, TFL1/CEN is expressed in the centre of the SAM. Upon transition from vegetative to reproductive growth, the expression of these genes increases (Bradley et al., 1996, 1997). Expression of the floral meristem identity genes such as LFY, AP1 and CAL is also increased in the SAM upon transition to reproductive growth, but the expression is confined to the developing flowers (Mandel et al., 1992; Bradley et al., 1997; Ratcliffe et al., 1999). In tobacco the CET2/CET4 genes are mainly expressed in the axillary meristems and not in the SAM (Amaya et al., 1999).

SUMMARY OF THE INVENTION

The present invention is based on investigations on the mechanism underlying flowering control and plant architecture In a widely distributed, agronomically important monocot crop plant. The present inventors had previously isolated a gene from perennial ryegrass, LpTFL1, which shows homology to the group of plant PEBPs, and demonstrated its role in determining plant architecture and effectively repressing the vegetative-reproductive phase transition in plants. The inventors have now transformed *Arabidopsis thaliana*, red fescue (*Festuca rubra* L.), and ryegrass (*Lolium perenne* L) with LpTFL1 and the results indicate that LpTFL1 is a repressor of flowering with a unique phenotypic effect not reported before. Overexpression of LpTFL1 in *Arabidopsis*, red fescue, and ryegrass results in a dramatic extension of the vegetative-inflorescence phase and a lateral branching in *Arabidopsis* that is consequently more extreme compared with overexpression of TFL1 in *Arabidopsis*. In addition, the results illustrate that LpTFL1 is capable of repressing flowering in perennial plants in the first year of growth and also in subsequent years. Repressors capable of preventing flowering and persisting to subsequent years have not hitherto been identified. The present inventors have also isolated the promoter of LpTFL1 and determined its potential use for up-regulating gene expression during long day flower induction.

Therefore, it is an object of the present invention to provide an isolated flowering repressor gene, the encoded protein, and its flowering related promoter, from plants.

Thus, in a first aspect, the present invention provides a method of significantly reducing or substantially preventing flowering in a perennial or biennial plant, the method comprising expressing a polypeptide from an isolated polynucleotide fragment comprising a nucleotide sequence as shown in FIG. 2, or a fragment, derivative, or homologue thereof, in a perennial or biennial plant. The nucleotide sequence represents a gene sequence isolated from the ryegrass *Lolium perenne* which is hereinafter referred to as "LpTFL1". Preferably the plant is a perennial.

In a second aspect, the present invention provides a method of significantly reducing or substantially preventing flowering in a perennial or biennial plant, the method comprising expressing an isolated polypeptide having an amino acid sequence as shown in FIG. 4, or a functionally active fragment, derivative or homologue thereof. The isolated polypeptide is encoded by the isolated polynucleotide fragment as shown in FIG. 2, or a fragment, derivative, or homologue thereof. Preferably the plant is a perennial.

The term "polynucleotide fragment" as used herein refers to a chain of nucleotides such as deoxyribose nucleic acid (DNA), oligonucleotides and transcription products thereof, such as RNA, mRNA, etc. The term may also be used interchangeably herein with the terms "polynucleotide", "DNA coding sequence", "gene", "genetic material", "gene sequence" and "genetic sequence".

The polynucleotide fragment can be isolated in the sense that it is substantially free of biological material with which the whole genome is normally associated in vivo. The isolated polynucleotide fragment may be cloned to provide a recombinant molecule comprising the polynucleotide fragment. Thus, "polynucleotide fragment" includes double and single stranded DNA, RNA, oligonucleotide and polynucleotide sequences derived therefrom, for example, sub-sequences (also referred to herein as sub-fragments) of said fragment and which are of any desirable length. Where a nucleic acid is single stranded then both a given strand and a sequence complementary thereto is within the scope of the present invention.

The polynucleotide fragment may be expressed in order to provide an expression product. In general, the term "expression product" refers to both transcription and translation products of said polynucleotide fragments. When the expression product is a "polypeptide" (i.e. a chain or sequence of amino acids displaying a biological activity substantially similar to the biological activity of an essential protein, it does not refer to a specific length of the product as such. Thus, the skilled addressee will appreciate that "polypeptide" encompasses inter alia peptides, polypeptides and proteins. The polypeptide if required, can be modified in vivo and/or in vitro, for example by glycosylation, amidation, carboxylation, phosphorylation and/or post-translation cleavage.

As is well known in the art, the degeneracy of the genetic code permits substitution of bases in a codon resulting in a different codon which is still capable of coding for the same amino acid, e.g. the codon for amino acid glutamic acid is both GAT and GAA. Consequently, it is clear that for the expression of polypeptides with the amino acid sequence shown in FIG. 4, or fragments thereof, use can be made of other nucleic acid sequences with such an alternative codon composition different from the nucleic acid sequence shown in FIG. 2. These are referred to herein as "derivatives".

The terms "homologues" or "homologous" as used herein refers to nucleotide sequences of polynucleotide fragments of the present invention which have 65% identity or above with the sequence disclosed herein, such as 66%, 68%, 70%, 75%, 80%, 83%, 86%, 88%, 90%, 92%, 95%, 97% or 99% identity. Such polynucleotide fragments may include, but are not limited to, known sequences which have not previously been identified as flowering repressors, such as FDR1 (85% identity) from rice, CET1 (66% identity), CET2 (72% identity), CET4 (71% Identity) from tobacco, SP (70% identity) from tomato, and BnTFL1-1 (68% identity), BnTFL1-3 (68% identity) from rapeseed, or may include sequences which are only known to delay flowering to some extent, such as FDR2 (87% identity) and RCN2 from rice, The term "identity" with respect to nucleotide sequences is defined as the percentage of nucleotides in a polynucleotide sequence which are identical to the nucleotides in the sequence disclosed herein after alignment as determined by using sequence analysis programs. Programs which are used for database searching and sequence alignment and comparison, for example, from the Wisconsin Package Version 10.2, such as BLAST, FASTA, PILEUP, FINDPATTERNS or the like (GCG, Madison, Wis.) or public available sequence databases such as GenBank, EMBL, Swiss-Prot and PIR or private sequence databases such as PhytoSeq (Incyte Pharmaceuticals, Palo Alto, Calif.) may be used to determine sequence identity, Alignment for sequence of comparison may be conducted by the local homology algorithm of Smith and Waterman (1981: Adv. Appl. Math., 2:482), by the homology alignment algorithm of Needleman and Wunsch (1970: J. Mol. Biol., 48:443), by the search for similarity method of Pearson and Lipman (1988: Proc. Natl. Acad. Sci. USA., 85: 2444), by computerized implementations of these algorithms.

Using the information provided by the present invention, isolated polynucleotide fragments similar to the LpTFL1 polynucleotide fragments disclosed herein for use in the methods of the present invention may now be obtained from any plant source using standard methods, for example, by employing consensus oligonucleotides and PCR. By "similar" is meant an isolated polynucleotide fragment comprising a nucleotide sequence which is capable of hybridising to a sequence which is complementary to the nucleotide sequence of the inventive polynucleotide fragment. The stringency of the hybridisation is used to determine the degree of similarity between two sequences. Normally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridise to a perfectly matched sequence (probe).

In the case that the similar and inventive sequences are mixed together and denatured simultaneously, the $T_m$ values of the sequences are preferably within 10° C. of each other. More preferably hybridisation may be performed under stringent conditions, with either the similar or inventive DNA preferably being supported. Thus for example either a denatured similar or inventive sequence is preferably first bound to a support and hybridisation may be effected for a specified period of time at a temperature of between 50 and 70° C. in double strength SSC (2×NaCl 17.5 g/l and sodium citrate (SC) at 8.8 g/l) buffered saline containing 0.1% sodium dodecyl sulphate (SDS) followed by rinsing of the support at the same temperature but with a buffer having a reduced SSC concentration. Depending upon the degree of stringency required, and thus the degree of similarity of the sequences, such reduced concentration buffers are typically single strength SSC containing 0.1% SDS, half strength SSC containing 0.1% SDS and one tenth strength SSC containing 0.1% SDS.

Sequences having the greatest degree of similarity are those the hybridisation of which is least affected by washing in buffers of reduced concentration. It is most preferred that the similar and inventive sequences are so similar that the hybridisation between them is substantially unaffected by washing or incubation at high stringency, for example, in one tenth strength sodium citrate buffer containing 0.1% SDS. These similar polynucleotide fragments from plants other than ryegrass are also encompassed by the term "homologues".

Therefore, the present invention also provides a method of significantly reducing or substantially preventing flowering in a perennial or biennial plant, the method comprising expressing a polypeptide from an isolated polynucleotide fragment comprising a similar nucleotide sequence, or fragments thereof, from other plants which are complementary to the one which hybridises under stringent or moderately stringent conditions with the nucleotide sequences of the isolated polynucleotide fragments, or fragments thereof, disclosed herein. The isolated polynucleotide fragments comprising a similar nucleotide sequence employed in the present invention may be isolated from any plant including monocots and dicots and in particular agriculturally important plant species, including but not limited to, crops such as those belonging to the grass family of Poaceae, and also soybean, potato, oilseed rape, sunflower, alfalfa, sugar cane and cotton; or herbs such as anise, basil, bay laurel, caper, caraway, cayenne pepper, celery, chervil, chives, coriander, dill, fennel, garlic, horseradish, leeks, lemon balm, liquorice, marjoram, mint, oregano, parsley, rosemary, sesame, tarragon and thyme; or fruits and vegetables, such as banana, blackberry, blueberry, strawberry, and raspberry, carrot, coffee, eggplant, grapes, honeydew, mango, onion, papaya, peas, peppers, pineapple, rosaceous fruits (such as apple, peach, pear, cherry and plum) and vegetable *brassicas* (such as brussel sprouts). The homologues may also be derived from woody species, such as eucalyptus, oak, pine and poplar.

The invention also provides a method of significantly reducing or substantially preventing flowering in a perennial or biennial plant, the method comprising expressing a polypeptide from an isolated polynucleotide fragment comprising a similar nucleotide sequence which is synthetic or artificial and is complementary to one which hybridises under stringent or moderately stringent conditions with the above disclosed nucleotide sequences, or fragments thereof.

The inventors have identified the genomic sequence corresponding to the cDNA sequence of FIG. 2 (SEQ ID NO: 1), which is illustrated as bold text in FIGS. 3A and 3B (SEQ ID NO: 2). The coding sequence, including introns and exons, of LpTFL1 is from bases 1 to 912 of SEQ ID NO: 2. Therefore, the present invention further provides an isolated polynucleotide fragment comprising the nucleotide sequence of bases 1 to 912 (SEQ ID NO: 2). Although base 1242 of SEQ ID NO: 2 corresponds to the end of the cDNA sequence, it is thought that that sequence from base 1243 to base 1624 of SEQ ID NO: 2 may comprise a polyadenylation signal. Therefore, the isolated polynucleotide fragments of the present invention may further comprise bases 1243 to 1624 of SEQ ID NO: 2 in conjunction with bases 1 to 1242 of SEQ ID NO: 2. In addition, the present invention provides a method of reducing or substantially preventing flowering in a perennial or biennial plant, the method comprising expressing a polypeptide from an isolated polynucleotide fragment comprising the nucleotide sequence of bases selected from the group consisting of bases 1 to 912, bases 1 to 1624, bases −78 to 912, bases −78 to 1242, and bases −78 to 1624, all of FIGS. 3A and 3B (SEQ ID NO: 2).

The inventors have also isolated a region upstream from the start codon that comprises the native promoter for the LpTFL1 gene in ryegrass (bases 1 to 3600 of SEQ ID NO: 2). Therefore, also provided in the present invention is a polynucleotide fragment which comprises a promoter with the nucleotide sequence of bases −3600 to −1 of FIGS. 3A and 3B (bases 1 to 3600 of SEQ ID NO:2).

The inventors determined the function of the LpTFL1 promoter by characterising the expression of LpTFL1 mRNA in ryegrass. The results showed that LpTFL1 is expressed in the apex of ryegrass at the vegetative stage. In contrast to TFL1 in *Arabidopsis*, the expression of LpTFL1 mRNA not only increases in the apex but also in the leaves (more than 25 fold) upon transition to reproductive growth. The increase in LpTFL1 mRNA expression in leaves seems to be stimulated by flowering induction i.e. long day treatment and temperature increase. Therefore, in another aspect, the present invention provides an isolated polynucleotide fragment having a nucleotide sequence of bases −3600 to −1 as shown in FIGS. 3A and 3B (bases 1 to 3600 of SEQ ID NO: 2), or a fragment or derivative thereof for up-regulating gene expression in the apex and leaves of a perennial or biennial plant during conditions that lead to flowering.

Flowering induction and conditions that lead to flowering are herein defined as a period of 8 to 18 weeks, in particular 10 to 16 weeks and in particular 12 to 14 weeks below 5° C. followed by secondary induction with long-day photoperiods which are generally more daylight hours than dark hours and, in particular, 13 h of light and 11 h of darkness, 14 h of light and 10 h of darkness, 15 h of light and 9 h of darkness, or 16 h of light and 8 h of darkness, and/or temperatures above 15° C., such as 16° C., 17° C., 18° C., 19° C., 20° C. or above.

It will be understood that for the particular polypeptides embraced herein, variations can be made to the polypeptides without substantially altering their function. These variations may be demonstrated by (an) amino acid difference(s) in the overall sequence or by deletions, substitutions, insertions, inversions or additions of (an) amino acid(s) in said sequence and are referred to as "derivatives" when referred to together with polypeptides. All such polypeptide derivatives showing the recognised physiological activity are included within the scope of the invention. For example, for the purpose of the present invention conservative replacements may be made between amino acids within the following groups:
(I) Alanine, serine, threonine;
(II) Glutamic acid and aspartic acid;
(III) Arginine and leucine;
(IV) Asparagine and glutamine;
(V) Isoleucine, leucine and valine;
(VI) Phenylalanine, tyrosine and tryptophan.

Also encompassed are synthetic amino acids incorporated into the polypeptides of the present invention, either by way of addition or substitution of existing amino acids.

Polypeptides, or fragments or derivatives thereof, modified as hereinbefore described, and which retain the physiological activity of the original, full-length peptide are referred to herein as "functional variants" or "functionally active variants". Moreover, recombinant DNA technology may be used to prepare nucleic acid sequences encoding the various derivatives outlined above.

The amino acid sequence or sequence motifs of the present invention may be used in homology searches in protein databases to find LpTFL1 related proteins from other plant species. Therefore, the present invention also provides a method of significantly reducing or substantially preventing flowering in a plant, the method comprising expressing polypeptide sequences homologous to the polypeptide sequence disclosed. herein from another plant. When referred to together with polypeptides, the term "homologue" refers to polypeptide sequences which have 69% identity or above with the sequence disclosed herein, such as 70%, 72%, 75%, 80%, 83%, 87%, 90%, 92%, 95%, 97% or 99% identity. The polypeptide sequences may be isolated from a plant such as a monocot or a dicot. The plant may further be an annual, a biennial or a perennial. Such polypeptide sequences may include, but are not limited to, known sequences which have not previously been identified as flowering repressors, such as FDR1 (86% identity) from rice, CET1 (68% identity), CET2 (72% identity), and CET4 (72% identity) from tobacco, SP (71% identity) from tomato, and BnTFL1-1 (70% identity) and BnTFL1-3 (70% identity) from rapeseed; or sequences which are known to be partially effective repressors of flowering, such as FDR2 (91% identity) and RCN2 from rice The term "identity" with respect to polypeptide sequences is defined as the percentage of amino acids in an polypeptide sequence which are identical to the amino acids in the polypeptide sequence disclosed herein after alignment as determined by using sequence analysis programs. Programs which are used for database searching and sequence alignment and comparison, for example, from the Wisconsin Package Version 10.2, such as BLAST, FASTA, PILEUP, FIND-PATTERNS or the like (GCG, Madison, Wis.) or public available sequence databases such as GenBank, EMBL, Swiss-Prot and PIR or private sequence databases such as PhytoSeq (Incyte Pharmaceuticals, Palo Alto, Calif.) may be used to determine sequence identity. Alignment for sequences of comparison may be conducted by the local homology algorithm of Smith and Waterman (1981: Adv. Appl. Math., 2:482), by the homology alignment algorithm of Needleman and Wunsch (1970: J. Mol. Biol., 48:443), by the search for similarity method of Pearson and Lipman (1988: Proc. Natl. Acad. Sci. USA., 85: 2444), by computerized implementations of these algorithms.

The terms "homologue" or "homologous" may also refer to polypeptide sequences, which are estimated to be clustered together with the polypeptide disclosed herein after a cladistic analysis of two to several homologous polypeptide sequences as determined by sequence analysis programs for multiple sequence alignments available, for example ClustalW (Tompson et. al. 1994: Nucleic Acids Res., 22:4673) or PILEUP which is included in the Wisconsin Package version 10.2 (GCG, Madison, Wis.) or the like. The cladistic analysis of sequences for comparison may be conducted by using different values for the ClustalW program parameters such as, gap open penalty, gap extension penalty, gap separation penalty, and protein weight matrix. The values for these parameters may be; gap open penalty (1; 2; 5; 10; 25; 50; 100), gap extension penalty (0.05; 0.2; 0.5; 1.0; 2.5; 5.0; 7.5; 10.0), gap distance penalty (1; 2; 3; 4; 5; 6; 7; 8; 9; 10), protein weight matrix (PAM developed by Dayhoff et al., 1978: Atlas of Protein Sequence and Structure, Dayhoff, MO, ed., NBRF, Washington:345; BLOSUM developed by Henikoff and Henikoff 1992: Proc. Natl. Acad. Sci. USA., 89:10915; GONNET updated matrix of Dayhoff et al., 1978: Atlas of Protein Sequence and Structure, Dayhoff, M O, ed., NBRF, Washington:345). When using ClustalW it is most preferred that the homologous polypeptide sequences and the inventive polypeptide sequence are clustered together by using the GONNET matrix in combination with gap open penalties higher than 5, gap extension penalties higher than or equal to 0.2, and gap distance penalties higher than 3. The number of homologous polypeptide sequences which may be clustered together with the inventive polypeptide sequence by the ClustalW alignment depends on the similarity of the analysed sequences. Analysis of polypeptide sequences with a high percentage of sequence identity will result in more homologous sequences being clustered together with the inventive sequence and analysis of polypeptide sequences with a lower percentage of sequence identity will result in fewer homologous sequences being clustered together with the inventive sequence. It is most preferred that the polypeptide sequences for comparison included in the ClustalW, or PILEUP, or the like, multiple alignment have 60% identity or above with the inventive polypeptide sequence disclosed herein.

Eleven amino acid residues in the plant PEBP sequences have so far been identified as essential for a functional protein by crystallography (Banfield and Brady, 2000) or by mutation (Bradley et al., 1997; Ohshima et al., 1997; Pnueli et al., 1998). At these residues, LpTFL1 differs from the consensus at only one position (110) which is also the position with the highest degree of amino acid variation between species. It is postulated that the Serine residue at position 110 may confer the superior repressor activity of flowering demonstrated herein. Therefore, the polypeptides expressed from the polynucleotide fragments of the present invention may include the sequence of YESP (KIR) (SEQ ID NOS: 30 and 31) located between about residues 100 and 120, from the N-terminus.

The present invention further provides a method of significantly reducing or substantially preventing flowering in a perennial or biennial plant, the method comprising inserting an expression cassette into a plant host cell, the expression cassette comprising a promoter and a nucleotide sequence as shown in FIG. 2, or a fragment or derivative thereof, growing the said transformed host cell in a suitable culture medium and expressing said DNA sequence to produce said protein, and wherein said expressed protein substantially reduces and/or prevents flowering in said plant. The promoter may be, for example, the monocot and dicot actin and ubiquitin promoters, monocot and dicot glyceraldehyde dehydrogenase (GAPDH) promoters, the cauliflower mosaic virus 35S (CaMV 35S) and 19S (CaMV 19S) promoters, the 35S CaMV promoter containing the translational enhancer (TMV omega element), the nopaline synthase (NOS) promoter, octopine synthase (OCS) promoter.

Expression of the flowering repressor protein may only be desirable for a limited period of time, for example, a limited number of seasons. Therefore, the polynucleotide of the present invention may be included in a controllable expression cassette wherein expression of the associated polynucleotide can be induced or reduced by an administered signal. In doing so, flowering will either become repressed or no longer be repressed and the plant will then proceed to flower.

In a yet further aspect the present invention provides a nucleotide sequence comprising a transcriptional regulatory sequence, a sequence under the transcriptional control thereof which encodes an RNA sequence characterised in that the RNA sequence is anti-sense to an mRNA which codes for LpTFL1 or functional homologues hereof.

The nucleotide sequence encoding the antisense RNA molecule can be of any length provided that the antisense RNA molecule transcribable therefrom is sufficiently long so as to be able to form a complex with a sense mRNA molecule encoding for LpTFL1. Thus, without the intention of being bound by theory it is thought that the antisense RNA molecule complexes with the mRNA for the protein or proteins and prevents or substantially inhibits the synthesis of a functional LpTFL1 or functional homologues hereof. As a consequence of the interference by the antisense RNA, flowering repressor activity of LpTFL1 or homologues hereof is substantially decreased or eliminated.

The DNA encoding the antisense RNA can be from about 20 nucleotides in length up to the length of the relevant mRNA produced by the cell. Preferably, the length of the DNA encoding the antisense RNA will be from 50 to 1500 nucleotides in length. The preferred source of antisense RNA transcribed from DNA constructs of the present invention is DNA showing substantial identity or similarity to LpTFL1.

Suppression of endogenous LpTFL1 expression can also be achieved using a ribozyme. Ribozymes are synthetic RNA molecules that possess highly specific endoribonuclease activity. The production and use of ribozymes are disclosed in U.S. Pat. No. 4,987,071 to Cech and U.S. Pat. No. 5,543,508 to Haseloff. The inclusion of ribozyme sequences within antisense RNAs may be used to confer RNA cleaving activity on the antisense RNA, such that endogenous mRNA molecules that bind to the antisense RNA are cleaved, which in turn leads to an enhanced antisense inhibition of endogenous gene expression.

Vectors in which RNA encoded by the LpTFL1 cDNA (or variants thereof) is over-expressed may also be used to obtain co-suppression of the endogenous LpTFL1 gene in the manner described in U.S. Pat. No. 5,231,020 to Jorgensen. Such co-suppression (also termed sense suppression) does not require that the entire LpTFL1 cDNA be introduced into the plant cells, nor does it require that the introduced sequence be exactly identical to the endogenous LpTFL1 gene. However, as with antisense suppression, the suppressive efficiency will be enhanced as (1) the introduced sequence is lengthened and (2) the sequence similarity between the introduced sequence and the endogenous LpTFL1 gene is increased.

Vectors expressing an untranslatable form of the LpTFL1 mRNA may also be used to suppress the expression of endogenous LpTFL1 activity to induce flowering. Methods for producing such constructs are described in U.S. Pat. No. 5,583,021 to Dougherty et al. Preferably, such constructs are made by introducing a premature stop codon into the LpTFL1 gene.

Alternatively, induction of flowering may be obtained by gene silencing using double-strand RNA (Sharp, 1999). This approach, whereby a vector is prepared in which a cDNA or gene is arranged in duplicated fashion and is capable of generating upon expression a double stranded RNA molecule with a hairpin structure. This procedure has been used to modify gene activity in plants (Chuang and Meyerowitz, 2000).

Another method for abolishing the expression of LpTFL1 is by insertion mutagenesis using the T-DNA of *Agrobacterium tumefaciens*. After generating the insertion mutants, the mutants can be screened to identify those containing the insertion in the LpTFL1 gene. Mutants containing a single mutation event at the LpTFL1 gene may be crossed to generate homozygous plants for the mutation (Koncz et al. (1992) Methods in *Arabidopsis* Research. World Scientific).

Flowering in a plant may also be controlled by recombinant systems such as the cre-lox system (for example, as described in U.S. Pat. No. 5,658,772). A plant genome may be modified to include first and second lox sites that are then contacted with a Cre recombinase. If the lox sites are in the same orientation, the intervening DNA sequence between the two sites is excised. If the lox sites are in the opposite orientation, the intervening sequence is inverted.

The polynucleotides and polypeptides of this invention may also be expressed in a plant in the absence of an expression cassette by manipulating the activity or expression level of the endogenous gene by other means. For example, by ectopically expressing a gene by T-DNA activation tagging (Ichikawa et al., (1997) Nature 390 698-701, Kakimoto et al., (1996) Science 274: 982-985). This method entails transforming a plant with a gene tag containing multiple transcriptional enhancers and once the tag has inserted into the genome, expression of a flanking gene coding sequence becomes deregulated. In another example, the transcriptional machinery in a plant may be modified so as to increase transcription levels of a polynucleotide of the invention (See PCT Publications WO9606166 and WO 9853057 which describe the modification of the DNA binding specificity of zinc finger proteins by changing particular amino acids in the DNA binding motif.

The transgenic plant may also comprise the machinery necessary for expressing or altering the activity of a polypeptide encoded by an endogenous gene, for example by altering the phosphorylation state of the polypeptide to maintain it in an activated state.

Therefore, a further aspect of the present invention provides transgenic perennial or biennial plants wherein the flowering repressor activity attributable to LpTFL1 in the cells of the plants has been significantly reduced or substantially prevented. The plants may, for example, be monocots or dicots.

Transcriptional initiation sequences are commonly located upstream from the transcriptional initiation site and which contains all the regulatory regions required for transcription. Examples of such transcriptional initiation sequences (also known as promoters) are hereinbefore described.

It will be appreciated that the promoter employed should give rise to the transcription of a sufficient amount of the antisense RNA molecule at a rate sufficient to cause an inhibition of LpTFL1 activity in plant cells. The required amount of antisense RNA to be transcribed may vary from plant to plant.

DNA constructs and nucleotide sequences of the invention may be used to transform cells of both monocotyledonous and dicotyledonous plants in various ways known in the art. For example, particle bombardment of embryogenic callus is the method of choice for production of transgenic monocotyledonous plants [Vasil (1994) Plant Mol. Biol. 25, 925-937]. In many cases transformed plant cells may be cultured to regenerate whole plants which can subsequently reproduce to give successive generations of genetically modified plants.

The invention also provides a biological vector comprising a DNA construct according to the present invention. The biological vector may be a virus or bacterium, such as *Agrobacterium tumefaciens*, for example, and the construct advantageously further encodes a marker protein, such as one having herbicide resistance, or anti-bacterial properties.

A further aspect of the invention is a recombinant biological vector comprising the said construct wherein said vector is capable of transforming a host cell. Also comprised is a host cell stably transformed with the said vector wherein said host cell is preferably a cell selected from the group consisting of a bacterial cell, a yeast cell, and an insect cell and is further capable of expressing the polypeptide from the polynucleotide of the present invention.

The invention still further provides eukaryotic cells, such as plant cells (including protoplasts) for example, containing the said nucleotide sequence, DNA construct or vector.

The invention still further provides plant cell with gene "knockouts" wherein the gene encoding LpTFL1 or a functional fragment or derivative or homologue thereof has been mutated or removed to eliminate expression. Without wishing to be bound by theory, it is thought that this will result in early flowering by a plant.

The invention still further provides transgenic plants comprising such plant cells, the progeny of such plants which contain the sequence stably incorporated and heritable in a Mendelian manner, and/or the seeds of such plants or such progeny. Progeny of transgenic plants may be obtained by traditional vegetative propagation or by micropropagation.

The invention still further provides the use of the sequence according to the invention, whether "naked" or present in a DNA construct or biological vector, in the production of eukaryotic cells, particularly plant cells having a modified LpTFL1 activity.

Other plant LpTFL1 related coding sequences may be isolated according to well known techniques based on their sequence homology to the sequence as shown in FIG. 2 (SEQ ID NO: 2), or fragment, or homologue thereof. In these techniques all or part of the known LpTFL1 coding sequence may be used as a probe which selectively hybridises to other LpTFL1 coding sequences present in a population of cloned genomic DNA fragments or cDNA fragments (i.e. genomic or cDNA libraries) from a chosen organism. Such techniques include hybridisation screening of plated DNA libraries (either plaques or colonies; see, e.g. Sambrook et al., "Molecular Cloning", eds., Cold Spring Harbor Laboratory Press. (1989)) and amplification by PCR using oligonucleotide primers, for example corresponding to sequence domains identified from the LpTFL1 gene sequence.

Therefore, a further embodiment of the invention is a method of isolating a polynucleotide fragment, said polynucleotide fragment comprising a sequence having at least 65% identity with the sequence disclosed herein, such as 68%, 70%, 75%, 80%, 83%, 86%, 88%, 90%, 92%, 95%, 97% or 99% identity, said method comprising (a) preparing a nucleotide probe capable of specifically hybridising to a plant LpTFL1 related gene or mRNA, wherein said probe comprises a contiguous portion of the coding sequence for LpTFL1 from ryegrass of at least 10 nucleotides in length;

(b) probing for other LpTFL1 related coding sequences in populations of genomic DNA fragments or cDNA fragments from a chosen plant using the nucleotide probe prepared according to step (a); and (c) isolating a polynucleotide fragment comprising a portion encoding a protein having LpTFL-like activity.

The isolated plant LpTFL1 and LpTFL1-related sequences taught by the present invention may be manipulated according to standard genetic engineering techniques to suit any desired purpose. For example, the entire LpTFL1 coding sequence or portions thereof may be used as probes capable of specifically hybridising to coding sequences and messenger RNAs. To achieve specific hybridisation under a variety of conditions, such probes include sequences that are unique among LpTFL1 coding sequences and are at least 10 nucleotides in length, preferably at least 20 nucleotides in length, and most preferably at least 50 nucleotides in length. Such probes may be used to amplify and/or analyse LpTFL1 coding sequences from a chosen organism via the well known process of polymerase chain reaction (PCR). This technique may be useful to isolate additional LpTFL1 related coding sequences from other plant species as hereinbefore described or as a screening assay to determine the presence of LpTFL1-related coding sequences in a plant. Hybridisation probes may also be used to quantitate levels of LpTFL1 mRNA in a plant using standard techniques such as Northern blot analysis.

LpTFL1-specific hybridisation probes may also be used, for example, to map the location of the native LpTFL1 related gene(s) in the genome of ryegrass using standard techniques based on the selective hybridisation of the probe to genomic LpTFL1 sequences. These techniques include, but are not limited to, identification of DNA polymorphisms identified or contained within the LpTFL1 probe sequence, and use of such polymorphisms to follow segregation of the LpTFL1 gene relative to other markers of known map position in a mapping population derived from self fertilization of a hybrid of two polymorphic parental lines (see e.g. Helentjaris et al., Plant Mol. Biol. 5: 109 (1985); Sommer et al. Biotechniques 12:82 (1992); D'Ovidio et al., Plant Mol. Biol. 15: 169 (1990)). Mapping of the LpTFL1 gene in this manner is contemplated to be particularly useful for breeding purposes. For instance, by knowing the genetic map position of a mutant LpTFL1 related gene which could affect flowering, flanking DNA markers can be identified from a reference genetic map (see, e.g., Helentjaris, Trends Genet. 3: 217 (1987)). During introgression of the mutant LpTFL1 related gene trait into a new breeding line, these markers can then be used to monitor the extent of LpTFL1 related flanking chromosomal DNA still present in the recurrent parent after each round of backcrossing.

For recombinant production of the flowering repressor protein in a host organism, the LpTFL1 DNA coding sequence may be inserted into an expression cassette to form a DNA construct designed for a chosen host and introduced into the host where it is recombinantly produced. The choice of specific regulatory sequences such as promoter, signal sequence, 5' and 3' untranslated sequences, enhancer and terminator appropriate for the chosen host is within the level of skill of the routine worker in the art. The resultant molecule, containing the individual elements linked in proper reading frame, may be introduced into the chosen cell, using techniques well known to those in the art, such as electroporation, biolistic introduction, Ti plasmid introduction etc. Suitable expression cassettes and vectors and methods for recombinant production of proteins are well known for host organisms such as *E. coli* (see, e.g. Studier and Moffatt, J. Mol. Biol. 189: 113 (1986); Brosius, DNA 8: 759 (1989)), yeast (see, e.g., Schneider and Guarente, Meth, Enzymol. 194: 373 (1991)) and insect cells (see, e.g., Luckow and Summers, Bio/Technol. 6: 47 (1988).

Examples of promoters suitable for use in DNA constructs of the present invention include viral, fungal, bacterial, animal and plant derived promoters capable of functioning in plant cells. The promoter may be selected from so-called constitutive promoters or inducible promoters.

Examples of suitable inducible or developmentally regulated promoters and constitutive promoters include the glutocorticoid-inducible transcription system, napin storage protein gene (induced during seed development), the malate synthase gene (induced during seedling germination), the small subunit RUBISCO gene (induced in photosynthetic tissue in response to light), the patatin gene highly expressed in potato tubers, monocot and dicot actin and ubiquitin promoters, monocot and dicot glyceraldehyde dehyrogenase (GAPDH) promoters, the cauliflower mosaic virus 35S (CaMV 35S) and 19S (CaMV 19S) promoters, the 35S CaMV promoter containing the translational enhancer (TMV omega element), the nopaline synthase (NOS) promoter, octopine synthase (OCS) promoter, heat shock 80 (hsp 80) promoter, the maize Ubiqinine promoter, and the like. In addition, the inventors have identified a 3.6kb LpTFL1 promoter (bases 1-3600 of SEQ ID NO:2) fragment upstream of the LpTFL1 DNA coding sequence, and this may be used as a promoter in an expression cassette. Therefore, in plants and plant cells of the invention, constitutive, inducible or developmentally regulated promoters are encompassed.

A terminator is contemplated as a DNA sequence at the end of a transcriptional unit which signals termination of transcription. These elements are 3'-non-translated sequences containing polyadenylation signals which act to cause the addition of polyadenylate sequences to the 3' end of primary transcripts. Sequences mentioned above may be isolated for example from fungi, bacteria, animals or plants.

Examples of terminators particularly suitable for use in the nucleotide sequence and DNA constructs of the invention include the nopaline synthase polyadenylation signal of *Agrobacterium tumefaciens*, the 35S polyadenylation signal of CaMV, octopine synthase polyadenylation signal, the zein polyadenylation signal from *Zea mays*, and those found in plasmids such as pBluescript (Stratagene, La Jolla, Calif.), pFLAG (International Biotechnologies, Inc., New Haven, Conn.), pTricHis (Invitrogen, La Jolla, Calif.), and baculovirus expression vectors, e.g., those derived from the genome of *Autographica californica* nuclear polyhedrosis virus (AcMNPV). An example baculovirus/insect system is pVI11392/Sf21 cells (Invitrogen, La Jolla, Calif.).

Therefore, the invention further provides an expression cassette comprising a promoter operably linked to a DNA coding sequence encoding LpTFL1, or a functionally active variant thereof and a terminator.

Recombinantly produced plant LpTFL1 protein or functionally active fragment can be isolated and purified using a variety of standard techniques. The actual techniques which may be used will vary depending upon the host organism used, whether the LpTFL1 protein or functionally active fragment is designed for secretion, and other such factors familiar to the skilled artisan (see, e.g. chapter 16 of Ausubel, F. et al., "Current Protocols in Molecular Biology", pub. By John Wiley & Sons, Inc. (1994).

Therefore, the present invention further provides the recombinant production of LpTFL1, or a functionally active fragment thereof. In particular, the invention relates to a method of producing a protein having LpTFL1 activity in a host organism comprising (a) inserting a DNA sequence encoding a protein having LpTFL1 activity into a host cell;

(b) growing the said transformed host cell in a suitable culture medium;

(c) expressing said DNA sequence to produce said protein; and (d) isolating the protein product either from the transformed host cell or the culture medium or both and purifying it.

The cloning and expression of a recombinant LpTFL1 polypeptide fragment or functionally active fragment also facilitates in producing anti-LpTFL1 antibodies and fragments thereof (particularly monoclonal antibodies) and evaluation of in vitro and in vivo biological activity of recombinant a LpTFL1 polypeptide or functionally active fragment. The antibodies may be employed in diagnostic tests for a native LpTFL1 polypeptide.

Further aspects of the invention relate to methods and materials for reducing or preventing flowering in monocotyledonous plants. Thus, in one aspect, the present invention provides a method of significantly reducing or substantially preventing flowering in a monocotyledonous plant, the method comprising expressing a polypeptide from an isolated polynucleotide fragment comprising a nucleotide sequence as shown in FIG. 2 (SEQ ID NO:1), or a fragment, derivative, or homologue thereof, in a monocotyledonous plant.

In a further aspect, the present invention provides a method of significantly reducing or substantially preventing flowering in a monocotyledonous plant, the method comprising expressing an isolated polypeptide having an amino acid sequence as shown in FIG. 4 (SEQ ID NO:3), or a functionally active fragment, derivative or homologue thereof. The present invention also provides a method of significantly reducing or substantially preventing flowering in a monocotyledonous plant, the method comprising expressing a polypeptide from an isolated polynucleotide fragment comprising a similar nucleotide sequence, or fragments thereof, from other plants which are complementary to the one which hybridises under stringent or moderately stringent conditions with the nucleotide sequences of the isolated polynucleotide fragments, or fragments thereof, disclosed herein. The invention still further provides a method of significantly reducing or substantially preventing flowering in a monocotyledonous plant, the method comprising expressing a polypeptide from an isolated polynucleotide fragment comprising a similar nucleotide sequence which is synthetic or artificial and is complementary to one which hybridises under stringent or moderately stringent conditions with the above disclosed nucleotide sequences, or fragments thereof. In addition, the present invention provides a method of reducing or substantially preventing flowering in a monocotyledonous plant, the method comprising expressing a polypeptide from an isolated polynucleotide fragment comprising the nucleotide sequence of bases selected from the group consisting of bases 1 to 912, bases 1 to 1624, bases −78 to 912, bases −78 to 1242, and bases −78 to 1624, all of FIGS. 3A and 3B, corresponding to bases 3600 to 4512, bases 3600 to 5224, bases 3522 to 4512, bases 3522 to 4842, and bases 3522 to 5224 of SEQ ID NO:2, respectively.

In another aspect, the present invention provides an isolated polynucleotide fragment having a nucleotide sequence of bases −3600 to −1 as shown in FIGS. 3A and 3B (bases 1-3600 of SEQ ID NO:2), or a fragment or derivative thereof, for up-regulating gene expression in the apex and leaves of a monocotyledonous plant during conditions that lead to flowering The present invention further provides a method of significantly reducing or substantially preventing flowering in a monocotyledonous plant, the method comprising inserting an expression cassette into a plant host cell, the expression cassette comprising a promoter and a nucleotide sequence as shown in FIG. 2 (SEQ ID NO: 1), or a fragment or derivative thereof, growing the said transformed host cell in a suitable culture medium and expressing said DNA sequence to produce said protein, and wherein said expressed protein substantially reduces and/or prevents flowering in said plant.

In various further aspects, the present invention relates to materials and methods for reducing or preventing flowering in a plant. Thus, in one aspect, the present invention provides a method of significantly reducing or substantially preventing flowering in a plant, the method comprising expressing a polypeptide from an isolated polynucleotide fragment comprising a nucleotide sequence as shown in FIG. 2 (SEQ ID NO: 1), or a fragment, derivative, or homologue thereof, in a plant. The nucleotide sequence represents a gene sequence isolated from the ryegrass *Lolium perenne* which is hereinafter referred to as "LpTFL1".

In a further aspect, the present invention provides a method of significantly reducing or substantially preventing flowering in a plant, the method comprising expressing an isolated polypeptide having an amino acid sequence as shown in FIG. 4 (SEQ ID NO:3), or a functionally active fragment, derivative or homologue thereof. The isolated polypeptide is encoded by the isolated polynucleotide fragment as shown in FIG. 2 (SEQ ID NO:1), or a fragment, derivative, or homologue thereof.

The present invention also provides a method of significantly reducing or substantially preventing flowering in a plant, the method comprising expressing a polypeptide from an isolated polynucleotide fragment comprising a similar nucleotide sequence, or fragments thereof, from other plants which are complementary to the one which hybridises under stringent or moderately stringent conditions with the nucleotide sequences of the isolated polynucleotide fragments, or fragments thereof, disclosed herein. The isolated polynucleotide fragments comprising a similar nucleotide sequence employed in the present invention may be isolated from any plant including monocots and dicots and in particular agriculturally important plant species, including but not limited to, crops such as those belonging to the grass family of Poaceae, and also soybean, potato, oilseed rape, sunflower, alfalfa, sugar cane and cotton; or herbs such as anise, basil, bay laurel, caper, caraway, cayenne pepper, celery, chervil, chives, coriander, cumin, dill, fennel, garlic, horseradish, leeks, lemon balm, liquorice, marjoram, mint, oregano, parsley, rosemary, sesame, tarragon and thyme; or fruits and vegetables, such as banana, blackberry, blueberry, strawberry, and raspberry, cantaloupe, carrot, cauliflower, coffee, cucumber, eggplant, grapes, honeydew, lettuce, mango, melon, onion, papaya, peas, peppers, pineapple, spinach, squash, sweet corn, tobacco, tomato, watermelon, rosaceous fruits (such as apple, peach, pear, cherry and plum) and vegetable *brassicas* (such as broccoli, cabbage, cauliflower, brussel sprouts, beet and kohlrabi). The homologues may also be derived from woody species, such as eucalyptus, oak, pine and poplar. The plant may further be an annual, a biennial or a perennial.

The invention also provides a method of significantly reducing or substantially preventing flowering in a plant, the method comprising expressing a polypeptide from an isolated polynucleotide fragment comprising a similar nucleotide sequence which is synthetic or artificial and is complementary to one which hybridises under stringent or moderately stringent conditions with the above disclosed nucleotide sequences, or fragments thereof.

In addition, the present invention provides a method of reducing or substantially preventing flowering in a plant, the method comprising expressing a polypeptide from an isolated polynucleotide fragment comprising the nucleotide sequence of bases selected from the group consisting of bases 1 to 912, bases 1 to 1624, bases −78 to 912, bases −78 to 1242, and bases −78 to 1624, all of FIGS. 3A and 3B, corresponding to bases 3600 to 4512, bases 3600 to 5224, bases 3522 to 4512, bases 3522 to 4842 and bases 3522 to 5224 of SEQ ID NO: 2, respectively.

In another aspect, the present invention provides an isolated polynucleotide fragment having a nucleotide sequence of bases −3600 to −1 as shown in FIGS. 3A and 3B (bases 1 to 3600 of SEQ ID NO:2 ) , or a fragment or derivative thereof, for up-regulating gene expression in the apex and leaves of a plant during conditions that lead to flowering.

The present invention further provides a method of significantly reducing or substantially preventing flowering in a plant, the method comprising inserting an expression cassette into a plant host cell, the expression cassette comprising a promoter and a nucleotide sequence as shown in FIG. 2 (SEQ ID NO:1), or a fragment or derivative thereof, growing the said transformed host cell in a suitable culture medium and expressing said DNA sequence to produce said protein, and wherein said expressed protein substantially reduces and/or prevents flowering in said plant. The promoter may be, for example, the monocot and dicot actin and ubiquitin promoters, monocot and dicot glyceraldehyde dehyrogenase (GAPDH) promoters, the cauliflower mosaic virus 35S (CaMV 35S) and 19S (CaMV 19S) promoters, the 35S CaMV promoter containing the translational enhancer (TMV omega element), the nopaline synthase (NOS) promoter, octopine synthase (OCS) promoter.

Expression of the flowering repressor protein may only be desirable for a limited period of time, for example, a limited number of seasons. Therefore, the polynucleotide of the present invention may be included in a controllable expression cassette wherein expression of the associated polynucleotide can be induced or reduced by an administered signal. In doing so, flowering will either become repressed or no longer be repressed and the plant will then proceed to flower.

A further aspect of the present invention provides transgenic plants wherein the flowering repressor activity attributable to LpTFL1 in the cells of the plants has been significantly reduced or substantially prevented. The plants may, for example, be monocots or dicots, and may further be annuals, biennials or perennials.

DNA constructs and nucleotide sequences of the invention may be used to transform cells of both monocotyledonous and dicotyledonous plants in various ways known in the art. For example, particle bombardment and Agro-mediated transformation of embryogenic callus is the method of choice for production of transgenic monocotyledonous plants [Vasil (1994); Tingay et al. (1997); Hiei et al. (1994)]. In many cases transformed plant cells may be cultured to regenerate whole plants which can subsequently reproduce to give successive generations of genetically modified plants.

DETAILED DESCRIPTION OF THE INVENTION

These and other aspects of the present invention will now be described by way of example only, in conjunction with the accompanying Figures, in which:

FIG. 1 illustrates the comparative morphology of perennial ryegrass and *Arabidopsis*. (A) The ryegrass vegetative apex is very compact with the SAM and the semicircular ridges that later will give rise to leaves and tillers. It is positioned on the basal crown and surrounded by developing leaves. Bar=1.0 mm. (B) The ryegrass inflorescence consists of spikelets alternately attached to the main axis (rachis). Each spikelet consists of three to 10 flowers. Bar=1.0 mm. (C) Schematic diagrams of ryegrass and *Arabidopsis*. During vegetative growth the SAM-of ryegrass and *Arabidopsis* produce very closely spaced leaves in a rosette. After the floral transition the SAM of both species elongate (bolt) and floral organs (circles) are produced along the main axis. In both plants secondary shoots arise from the axils of subtending leaves. In *Arabidopsis* wild type, flowers mature in an acropetal order and the SAM grows indefinitely (arrowheads), whereas in the tfl1 mutant the SAM and the secondary shoots terminate in a flower. Like the tfl1 mutant, the ryegrass SAM and secondary shoots also terminate in a flower. Maturation of flowers in the ryegrass inflorescence is basipetal, and all the secondary shoots formed below the apex also develop into arrays of flowers in a cymose pattern. The collar is a special meristematic region on the leaf blade in the junction between the leaf blade and the stem (black circles). An enlargement of a floret is shown (redrawn from K. Esau, Anatomy of Seed Plants, Ed 2. Wiley and Sons, New York, 1977). Each floret consists of four whorls of organs. The outermost whorl consists of the palea and the lemma surrounding the lodicules (whorl 2), the three stamens (whorl 3), and the ovary (whorl 4), which is interpreted as syncarpous, consisting of two or three carpels forming the ovary (C);

FIG. 2 (SEQ ID NO: 1) illustrates the cDNA sequence of the LpTFL1 gene;

FIGS. 3A and 3B (SEQ ID NO: 2) illustrates the genomic sequence of the LpTFL1 gene (bases -78 to 1624) and the upstream promoter region (bases -3600 to -1), corresponding to bases 3522 to 5224 of SEQ ID NO: 2 and 1 to 3600 of SEQ ID NO: 2, respectively;

FIG. 4 is the polypeptide sequence (SEQ ID NO: 3) derived from the polynucleotide sequence of FIG. 2 (SEQ ID NO: 1)

FIG. 5 illustrates the genomic organisation of LpTFL1 and similarity of the deduced protein with other plant PEBPs. (A) The upper bar shows the genomic organisation of the gene, including the untranslated (black boxes) and the translated (white boxes) regions. A 180bp DNA fragment was isolated from ryegrass by RT-PCR. (B) Comparison of the deduced protein sequence for the LpTFL1 gene (accession no. AF316419) with those of TFL1(Bradley et al., 1997; Ohshima et al., 1997), CEN (Bradley et al., 1996), SP (Pnueli et al., 1998), BNTFL1-1 and BNTFL1-3 (Mimida et al., 1999), CET1, CET2, and CET4 (Amaya et al., 1999), FDR1 and FDR2 (accession nos. AAD42896 and AAD42895, respectively), and FT(Kardailsky et al., 1999; Kobayashi et al., 1999). In figure 5(b) the sequences correspond to the sequence listing as follows: TFL1 is SEQ ID NO: 4, BNTFL1-1 is SEQ ID NO: 5, BNTFL1-3is SEQ ID NO: 6, CEN is SEQ ID NO: 7, CET2 is SEQ ID NO: 8, CET4 is SEQ ID NO: 9, SP is SEQ ID NO: 10, CET1 is SEQ ID NO: 11, LpTFL1 is SEQ ID NO: 3, FDR2 is SEQ ID NO: 12, FDR1 is SEQ ID NO: 13, FT is SEQ IDNO: 14.

Figure 6:
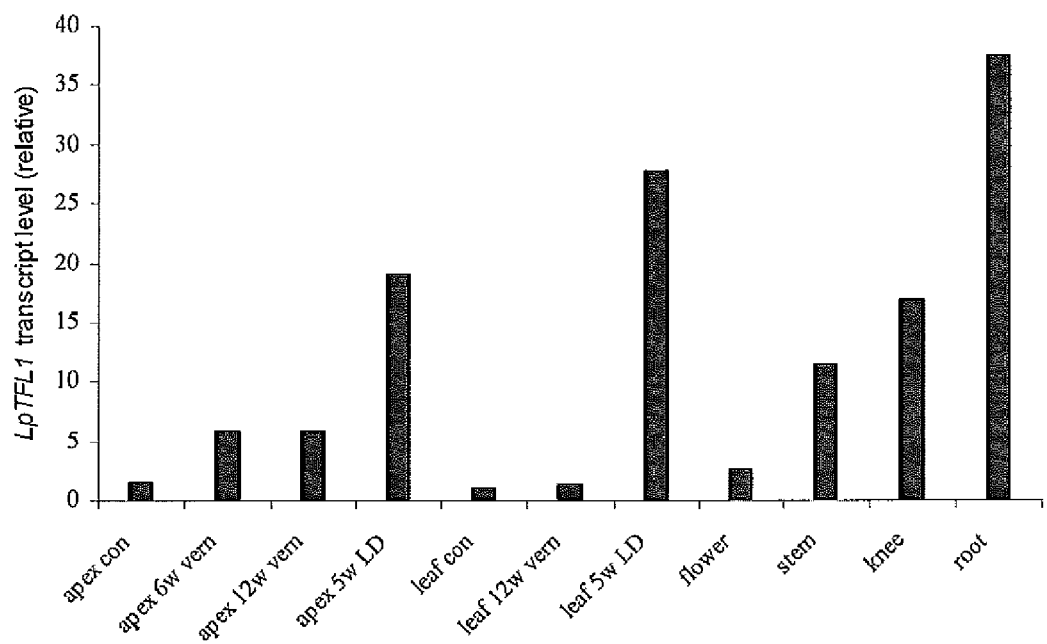

CLUSTAL W program was used to make the alignment and the deduced distance tree. Identical residues are in black. Dashed lines indicate gaps introduced by the program to achieve maximum alignment. Identical intron positions among all species are marked with black arrowheads. White arrowheads indicate amino acids Identified to be at the ligand-binding sites by crystallography (Banfleld and Brady, 2000) and asterisks indicate amino acids in which point mutations were described for *Arabidopsis* (Bradley et al., 1997; Ohshima et al., 1997) and tomato (Pnueli et al., 1998). (C) Distance tree of different plant PEBPs. The lengths of the horizontal lines are proportional to the similarity between the predicted protein sequences;

FIG. 6 illustrates the LpTFL1 mRNA levels in various tissues detected by Real-time quantitative RT-PCR Five micrograms of RNA from each of eleven different tissue samples which included flowers, stems, roots, leaves from non-induced (control), 12 weeks vernalized and five weeks long day (LD) induced plants and apices from control, 6 and 12 weeks vernalized and 5 weeks LD induced plants was used for the analysis. Levels of the constitutively expressed GAPDH mRNA were measured simultaneously, and the amount of LpTFL1 mRNA in each sample was normalised to the amount of GAPDH.

Figure 7:
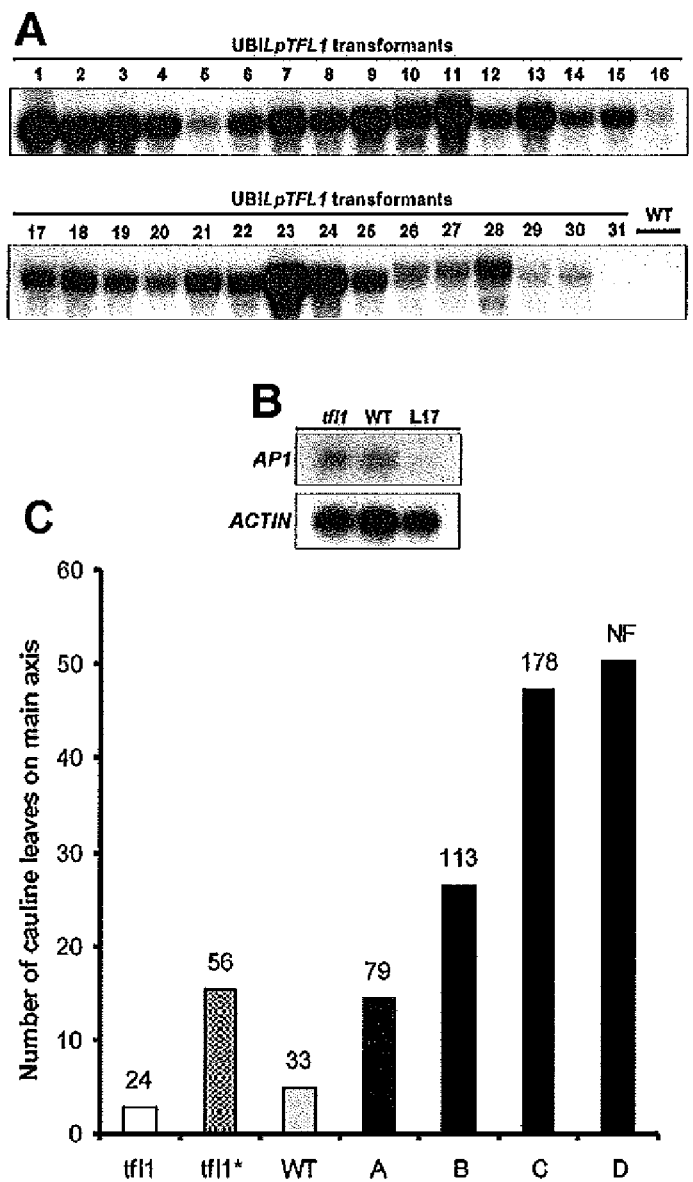

FIG. 7 illustrates that UBI-LpTFL1 dramatically alters the duration of the vegetative phase of *Arabidopsis*. (A) RNA gel-blot analysis of primary transformants (lines 1-30) and wild-type plants (WT). Fifteen micrograms of RNA from rosette leaves was blotted and probed with a LpTFL1 cDNA probe. Transgenic lines 5, 16, 29, and 30 have single-copy insertions as detected by DNA-blot analysis (not shown). Lines 2, 7, 9, 11, and 13 were non-flowering. (B) Expression of AP1 and ACTIN in a tfl1-14 mutant line, wild type, and in a UBI::LpTFL1 plant (line 17) as detected by RT-PCR on 5 µg of RNA from each plant. C, Number of cauline leaves produced on the main stem in tfl1 mutant, the complemented mutant (tfl1*), wild type (WT), and UBI-LpTFL1 primary transformants (groups A-D). Each bar represents the mean value of the plants within the specific group. Numbers above the bar indicates the total number of days from germination till the onset of the first flower. The plants were grouped according to the time to flowering: (A≧75 d; B≧100 d; C≧150 d; D non-flowering [NF]) The number of plants in each group is tfl1, 6; tfl1*, 6; WT, 6; A, 6; B, 13; C, 5; and D, 5.

Figure 8:
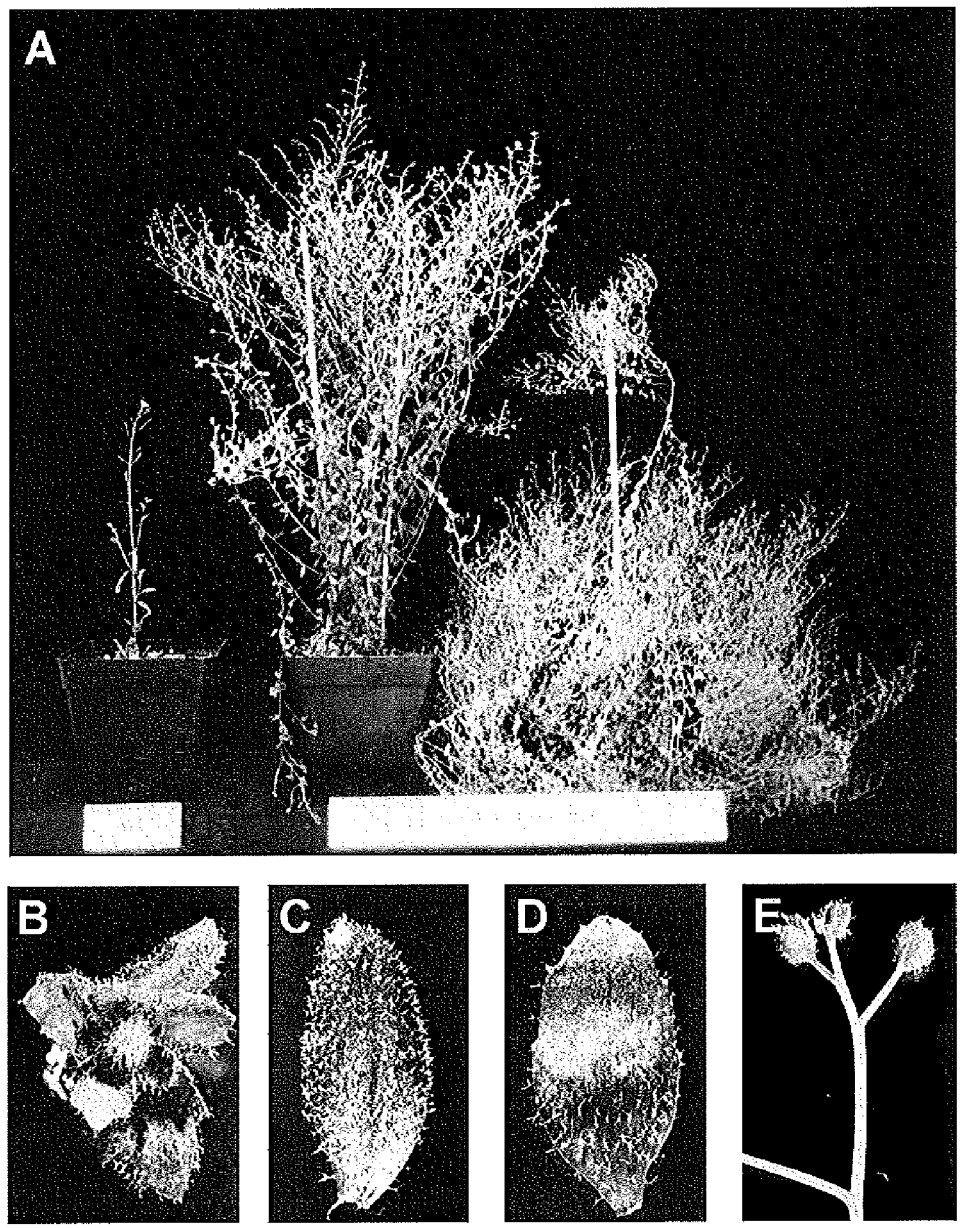

FIG. 8 illustrates the effect of UBI-LpTFL1 on the morphology of *Arabidopsis*. (A) The UBI::LpTFL1 *Arabidopsis* primary transformants, line 1 and 2 (right-hand side), showing extensive vegetative growth and up to fourth-order branching 4 months after germination compared with a 1-month-old flowering wild-type plant (left side). Line 2 (middle) was non-flowering after 7 months of growth. (B) The SAM of most UBI::LpTFL1 *Arabidopsis* lines is compact, filled with leaf primordia, and covered with trichomes. (C) and (D) Trichome distribution on the adaxial surface of the uppermost cauline leaves on the main stem of UBI:: LpTFL1 (C) compared with wild-type cauline leaves at same age (D). (E) In the UBI::LpTFL1 plants leafy shoots filled with trichomes are produced in place of normal flowers on the upper coflorescences.

Figure 9:
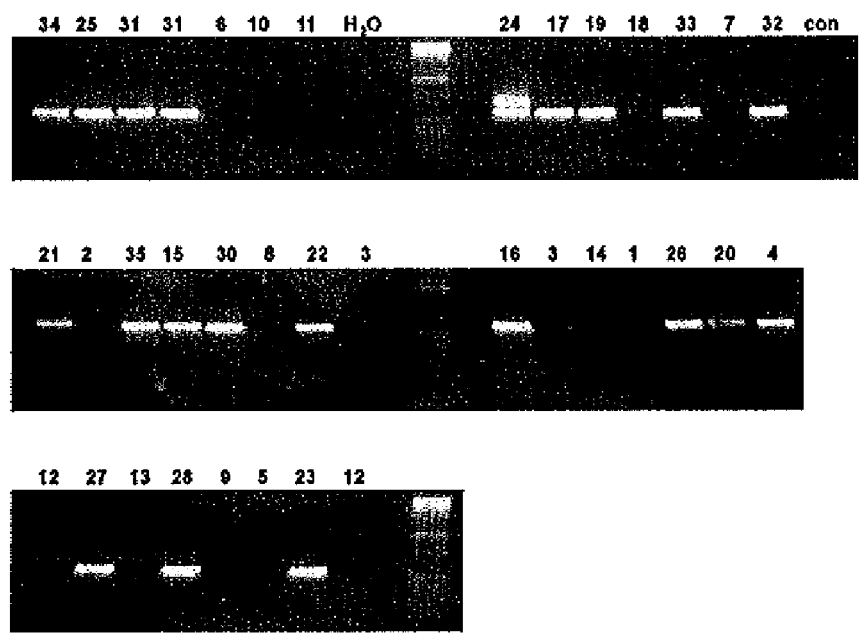

FIG. 9 illustrates the integration of LpTFL1 transgene by PCR analysis of genomic DNA from non-transformed (CON) and basta-resistent ryegrass lines (numbers). Primer LP0 was used in combination with primer MS8 to amplify a 560-bp fragment. Approximately 0.3 pg of genomic DNA was used per reaction.

Figure 10:
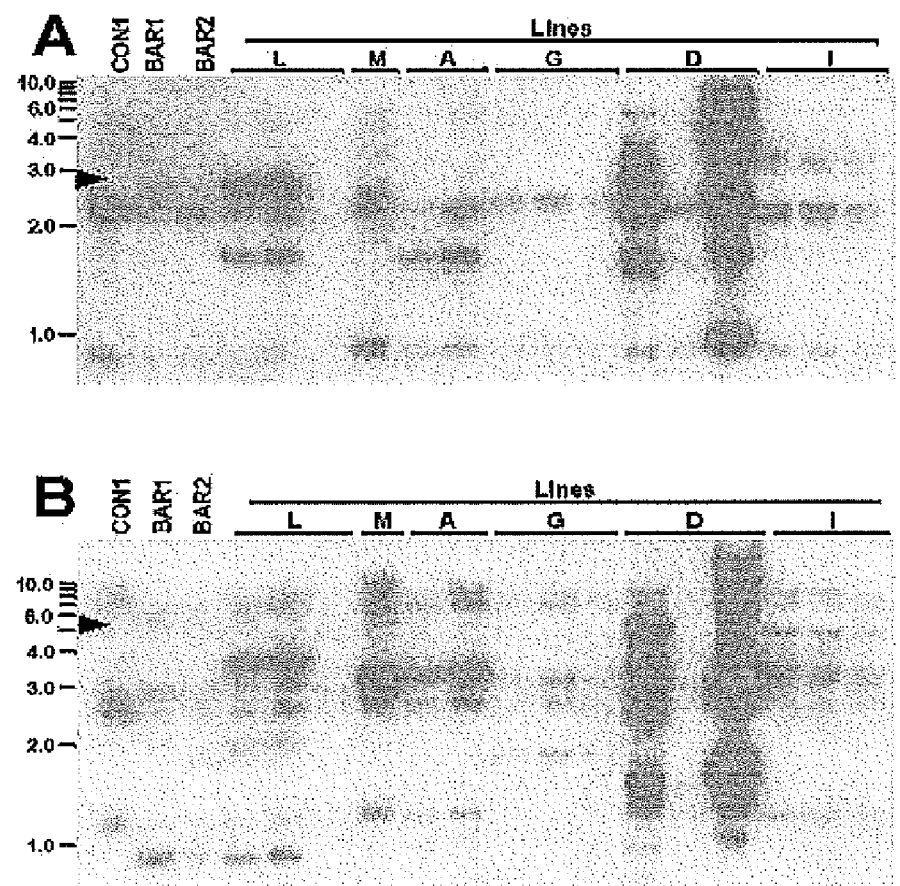
Figure 11:
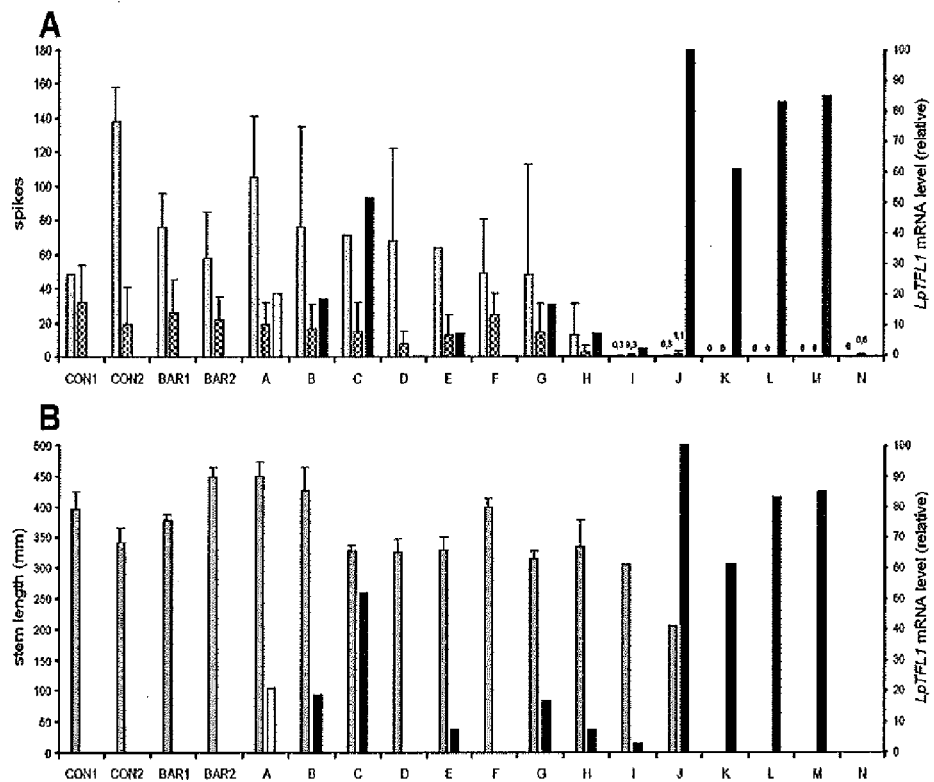

FIG. 10 illustrates the DNA blot hybridisation analyses of genomic DNA from non-transformed (CON 1) and transgenic red fescue. DNA samples of 10-30 µg were restricted with HinDIII (A) or EcoRI (B) and probed with a 0.4-kb fragment containing the 3'-end of the ubiquitin intron and the 5'-end of the LpTFL1 coding region (MS56-LP4REV, see Table 1). HinDIII release from pLPTFL1 a 2.8-kb fragment containing the entire LpTFL1 cassette (arrowhead). EcoR1 has a single restriction site on pLPTFL1, which is a 5.5-kb plasmid (arrowhead);

FIG. 11 illustrates the transgene levels and phenotypes of the transgenic UBI::LpTFL1 fescue lines. A. Average number of spikes produced per clone during the first (grey bars) and the second (checked bars) season by the lines (A-N), the non-transformed (CON), and the transformation controls (BAR), compared with the relative levels of LpTFL1 mRNA (black bars, second Y-axis). The white bar represents the level of a transcript corresponding to a truncated LpTFL1 mRNA. B. The average stem length of each line measured during the first season (grey bars) and compared with LpTFL1 mRNA levels (black bars, second Y-axis). Error-bars show the standard deviation from the average value within each line. All LpTFL1 mRNA levels are relative to the level of LpACTIN, and the highest detected value was set to 100 (line J).

Figure 12:
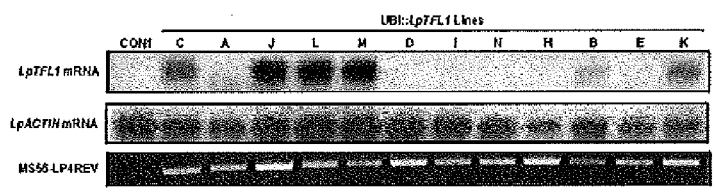
Figure 13:
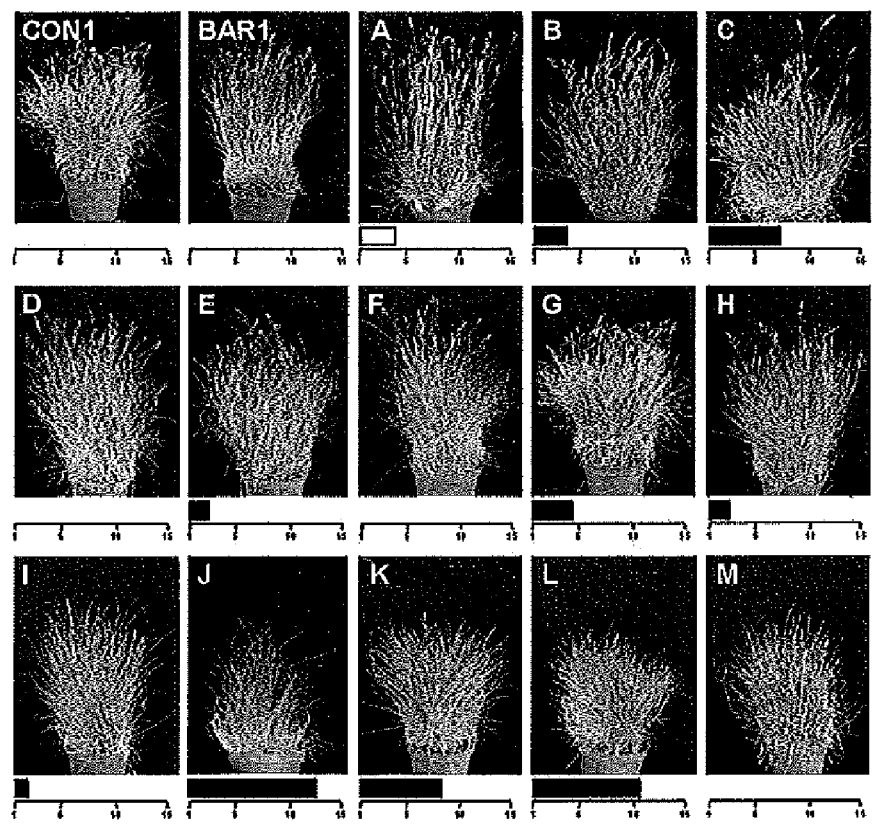
Figure 14:
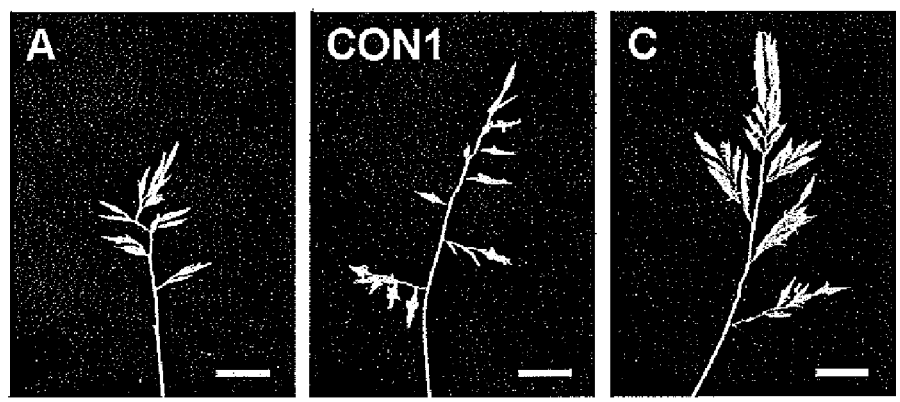

FIG. 12 illustrates an RNA gel blot analysis of primary transformants from different UBI::LpTFL1 lines. 2.5 µg of poly-A+mRNA each line were blotted and probed with a 200 bp LpTFL1 or a 450 bp LpACTIN cDNA probe. All the lines included were positive for the transgene as was verified by PCR (lower panel) using the primers MS56 and Lp4REV which amplifies a 425 bp fragment corresponding to the last 75 bases in the ubiquitin 3' end and 350 bases of the LpTFL1 cDNA;

FIG. 13 illustrates the flowering and non-flowering plants of 400 days old fescue wild-type (CON), transgenic controls (BAR) and UBI::LpTFL1 lines (A-M). Each line represents a single transformation event. Black bars below each picture shows to the LpTFL1 transcript level relative to the level in the non-transformed control plants, which was set to 1.0. The white bar indicates that the level corresponds to level of an overexpressed truncated LpTFL1 transcript; and FIG. 14 illustrates the Panicle phenotypes of red fescue wild-type (CON1) and of the UBI::LpTFL1 transgenic lines A and C, which overexpress a truncated and a correct LpTFL1 transcript, respectively. Bar=1 cm.

FIG. 15 is a table showing the transformation efficiency and the floral activity for a number of transgenic ryegrass lines transformed with LpTFL1.

FIG. 16 shows analysis of transgene integration by PCR in UBI::LpTFL1 transgenic red fescue lines.

EXAMPLES SECTION

1. Expression of LpTFL1 in *Arabidopsis*

Materials and Methods

Plant Growth Conditions

Ryegrass *Lolium perenne*) plants (clone F6, DLF-TRIFOLIUM) were grown in soil in a greenhouse with daylight at 21 and 18° C., day and night temperature, respectively. For the primary induction (vernalization) plants were grown in a growth chamber at or below 5° C. for at least 12 weeks. During vernalization, the light period was decreased to 8 h per day. Following vernalization, plants were grown under 16 h of light at 22° C. and 18° C., day and night temperature, respectively, for secondary induction. For RNA analysis wild-type plants were harvested before vernalization, after 6 weeks of vernalization, and after 14 and 28 d of secondary induction and meristems were excised. Samples from other tissues like leaves, stems, seeds, and roots were also harvested for expression analysis.

*Arabidopsis* seeds were stratified for 2 to 3 d at 4° C. and then grown in soil in growth chambers at 22° C. and 18° C., day and night temperature, respectively. During the first 2 weeks plants were grown at SD conditions (8 h of light per day) and then moved to LD conditions (16 h of light per day). In the *Arabidopsis* time-course experiment rosette leaves were counted when plants started to bolt and the number of leaf nodes were counted from the most basal cauline leaf to the uppermost leaf proximal to the inflorescence. The number of days from germination to the production of the first flower-like structure was also scored.

Screening of cDNA and Genomic Library

To isolate plant PEBP genes from ryegrass, a set of primers partially homologous to TFL1 of *Arabidopsis*, CEN of *Antirrhinum*, and a rice EST (RICR2918A; accession no. 428842) were designed. Primer RY2 N (5'-GGTTATGACAGAC-CCAGATGTG-3') (SEQ ID NO: 15) was used in combination with primer RY4V (5'-CGAACCTGTGGATAC-CAATG-3') (SEQ ID NO: 16) to amplify a 180-bp fragment by RT-PCR. Preparation of RNA for the RT-PCR used the primer RY4V (5'-CGMCCTGTGGATACCMTG-3') to amplify a 180-bp fragment by RT-PCR. Preparation of RNA for the RT-PCR used the FastRNA, GREEN Kit RNA isolation system (Biol 01, Carlsbad, Calif.). The 180-bp fragment was used to screen a cDNA library (Stratagene, La Jolla, Calif.) made of ryegrass inflorescences for full-length cDNAs. Approximately 800,000 recombinants were screened at moderate stringency of 60° C., with washes at 60° C. in 2×SSC (0.3M NaCl and 0.1M sodium citrate, pH 7.4) and 0.1% (w/v) SDS. Three positive clones were isolated, and plasmids were isolated from single plaques by in vivo excision. All cDNA clones were sequenced and contained identical sequences with similarity to TFL1 and CEN and were named ryegrass TFL1-like, LpTFL1 (GenBank accession no. AF316419).

A λEMBL3 SP6/T7 genomic library (CLONTECH, Palo Alto, Calif.) made from a partial Sau3A digest of ryegrass DNA was screened for TFL1-like genes. Approximately 1,000,000 recombinants were screened at moderate stringency (as described above) with the full-length LpTFL1 cDNA clone. Nine positive clones were isolated and digestion of the λ DNA clones with BamH1, SalI, XbaI, and SacI revealed three unique clones. These clones were partially sequenced and all three had identical sequence from 4.0 kb upstream and 2.0 kb downstream of the LpTFL1 sequence. The sequence of the exons of the genomic clones, as well as the 5' and 3' untranslated region were identical to LpTFL1. DNA sequencing was performed using the ABI Prism system (Perkin-Elmer, Foster City, Calif.), and sequence analysis and alignments were produced using Gene Codes Sequencer software, version 4.02.

RNA/DNA Analysis

For detection of LpTFL1 mRNA level in different organs of ryegrass at different stages poly-(A)+ mRNA was isolated from 5 µg of total RNA from each tissue sample and all mRNA was used in the reverse transcription. Two internal primers, INS5 (5'-CACATTGGTTATGACGGACC-3') (SEQ ID NO: 17) and INS3 (5'-CTCCCCCCCAAATGAAGC-3')

(SEQ ID NO: 18), were used in the subsequent Real-time quantitative PCR reaction to amplify a 200-bp LpTFL1 fragment from the first strand cDNA templates. Amplification of PCR products were performed and monitored by the Light-Cycler™ system in which inclusion of the fluorescent dye SYBR green I Dye into the reaction mixture facilitates direct measurement of double stranded DNA after each PCR cycle. In this experiment, the LpTFL1 expression level was analyzed in eleven different tissue sample which included flowers, stems, knees, roots, leaves from non-induced (control), 12 wk vernalized and 5 wk long day (LD) induced plants and apices from control, 6 and 12 wk vernalized and 5 wk LD induced plants. One microliters of each RT-reaction were used as template in the PCR reaction together with dilutions of plasmids containing LpTFL1 and LpGAPDH (100, 10, 1 and 0.1 pg). In order to normalize the PCR results relative to the initial template amount in each sample, a PCR was run in parallel on similar samples with the primers GAP5 (5'-CAAGGACTGGAGAGGTGG-3') (SEQ ID NO: 19) and GAP3 (5'-TTGACTCGTTGTCGTACC-3') (SEQ ID NO: 20) to amplify a 380 bp LpGAPDH fragment. Detection of LpTFL1 RNA levels in transformed *Arabidopsis* was performed by standard RNA gel-blot analysis.

Construction of UBI::LpTFL1 and the Transformation of *Arabidopsis* Wild Type and tfl1 Mutants The coding region of LpTFL1 cDNA was amplified using primers B0 (5'-GGATCCCCATGTCTAGGTCTGTGGAG-3') (SEQ ID NO: 21) and B550 (5'-GGGATCCCA-CAACTGGGATAG-CCA-3') (SEQ ID NO: 22) and recombinant pfu polymerase. The fragment was blunt ligated into vector pAHC27 (Christensen and Quail, 1996) containing the maize Ubiquitin promoter, an exon:intron region, and the NOS terminator. The entire cassette (UBI::EXintron::LpTFL1::NOS) was excised from the plasmid by digestion with HindII and EcoRI and was ligated into the EcoRI-HindII site of the binary vector pCAMBIA3300 (Jefferson, Australia), which confers BASTA resistance, to give pCAM-LPTFL1. *Arabidopsis* plants (Columbia and tfl1-14 mutants) were transformed with *Agrobacterium tumefaciens* strain GV3101 (Koncz and Schell, 1986) harbouring the pCAM-LPTFL1 (for LpTFL1 overexpression) using the floral dip method described by Clough and Bent (1998).

Results

Isolation of a Plant PEBP Gene from Ryegrass

LpTFL1 was amplified from ryegrass inflorescence mRNA by reverse transcriptase (RT) PCR using primers designed on the basis of an alignment of *Arabidopsis* TFL1, *Antirrhinum* CEN, tomato SP, and a related rice expressed sequence tag (EST; FIG. 5A). This fragment was used to screen a ryegrass flower cDNA library at moderate stringency for plant PEBP genes (LpTFL1 genes). One full-length cDNA was identified. The coding region of this cDNA shows 87% and 85% DNA sequence identity to two rice genes, FDR2 and FDR1, and 67% and 64% identity with TFL1 and CEN, respectively. The region in the rice EST used to design the LpTFL1-specific primers is 86% identical to LpTFL1. On the protein level LpTFL1 shows 91% and 86% identity to the corresponding proteins, FDR2 and FDR1, respectively, and 71% and 68% identity to TFL1 and CEN (FIG. 5B). The LpTFL1 cDNA-coding region shows 60% identity with the FT sequence, and the protein identity is 56%. Comparison of LpTFL1 sequence with other plant PEBP sequences found in the database revealed that LpTFL1 groups together with the two rice proteins and also CET1 from tobacco (FIG. 5C). Banfield and Brady (2000) have recently determined the three-dimensional structure of the CEN protein and identified the amino acids essential for a functional ligand-binding site. Other amino acids important for a functional protein have been identified by mutation (Bradley et al., 1997; Ohshima et al., 1997; Pnueli et al., 1998) (FIG. 5B). Of these 11 functionally important amino acids, LpTFL1 differs from CEN at only one position (110), having a Ser instead of a Met.

A DNA-blot analysis at moderate stringency using a full-length LpTFL1 cDNA fragment as probe was performed to assess the number of Plant PEBP genes in ryegrass. The results indicate that two Plant PEBP genes are present in ryegrass (data not shown). To gain more information on the LpTFL1 gene we screened a ryegrass genomic library with the full-length LpTFL1 cDNA clone. Three independent genomic clones were retrieved and sequenced. All had an identical DNA sequence predicting the same open reading frames, which exactly matched the LpTFL1 cDNA. The LpTFL1 genomic sequence contains three introns of 100, 208, and 82 bp, respectively. In the approximately 3.6kb region upstream of the transcription start (bases 1-3600 of SEQ ID NO:2), no likely gene encoding open reading frames were found; this is the LpTFL1 promoter.

The LpTFL1 Gene in Ryegrass Shows an Expression Pattern Different from TFL1 in *Arabidopsis*

To determine the expression pattern of LpTFL1 message in ryegrass we examined the mRNA levels in different tissues by the LightCycler™ real time quantitative PCR. In order to compare the different samples in the PCR, the calculated LpTFL1 template concentrations had to be normalized to the levels of LpGAPDH template concentration (Table 1). We assumed that LpGAPDH is constitutively expressed in all cells at different time points.

LpTFL1 message was detectable in all types of tissue tested (FIG. 6). In the vegetative ryegrass, LpTFL1 mRNA was expressed at very low levels both in the apex as well as in the leaves. During vernalization the expression of LpTFL1 mRNA was slightly upregulated in the apex but remains low in the leaves. However during the subsequent LD treatment the level of LpTFL1 mRNA expression was significantly increased both in the apex (12.6 fold) and even more in the leaves (27.8 fold). Highest expression was observed in roots. The LD induced upregulation of LpTFL1 expression in ryegrass has not been reported for any other plant PEBP so far identified, and expression of plant PEBPs outside the meristematic regions have only been detected in tobacco and tobacco by RT-PCR (Bradley et al., 1996; Amaya et al., 1999).

LpTFL1 Delays or Prevents Flowering in *Arabidopsis*

LpTFL1, one of the two Plant PEBP genes in ryegrass, has a function similar but noticeably stronger than the *Arabidopsis* TFL1. We used the maize ubiquitin promoter (Christensen and Quail, 1996) to drive overexpression of the LpTFL1-coding region in *Arabidopsis*. Following transformation with UBI::LpTFL1, 33 BASTA-resistant *Arabidopsis* plants were obtained. All the transformants showed remarkable vegetative characteristics and were much delayed in flowering compared with the wild type (FIGS. 4 and 5). Whereas wild-type plants bolted 10 d after they were moved from SD (short day) to LD photoperiod, even the earliest flowering UBI::LpTFL1 plants required another month in LD before they bolted. After 3 months, more than one-half of the plants had not produced a single flower (FIG. 7C). Overexpression of LpTFL1 affected the vegetative and the early inflorescence stage of *Arabidopsis*, as observed by the increased number of nodes produced before and after bolting. During the vegetative phase, wild-type *Arabidopsis* plants produced 16±1.9 rosette leaves, whereas the UBI::LpTFL1 plants grown under the same conditions produced 33.9±8.9 rosette leaves (not shown). After the plants had bolted, the UBI::LpTFL1 plants produced 26±14.3 cauline leaves on the main stem before flowering, in contrast to the wild type, which produced only 4.8±0.4 cauline leaves (FIG. 7C). Thus, in terms of time and the number of nodes produced before flowering, the majority of the UBI::LpTFL1 plants appeared to be arrested in the early inflorescence phase. Overexpression of TFL1 in *Arabidopsis* driven by the 35S cauliflower mosaic virus (CaMV) promoter has also been described (Ratcliffe et al., 1998). However, the 35S::TFL1 plants produced only two-thirds of the number of rosette leaves and one-half of the number of cauline leaves compared with the UBI::LpTFL1 plants, when grown under continuous light (Ratcliffe et al., 1998). Five UBI::LpTFL1 plants (lines 2, 7, 9, 11, and 13) remained in the early inflorescence stage throughout their life cycle and failed to produce flowers before they senescenced and died (after 7 months). This is an extraordinary observation since non-flowering individuals has not been observed in 35S::TFL1 *Arabidopsis* grown under LD inductive conditions. Only when 35S::TFL1 *Arabidopsis* plants were grown under SD non-inductive conditions a few lines remained without flowers (Ratcliffe et al., 1998).

In addition to the main SAM, *Arabidopsis* plants transformed with UBI::LpTFL1 also exhibit abnormal axillary meristem development. The development of coflorescences with developing flowers in the axils of the cauline leaves normally observed in wild-type *Arabidopsis* was rarely seen in the UBI::LpTFL1 plants. However, in the place of floral organ formation, a "leafy" branch was produced, resulting in a highly branched, bushy, and dramatic phenotype (FIG. 8A). Third-order branching was a common trait among the UBI::LpTFL1 plants, and fourth-order branching was observed in a single plant (FIG. 8A, right-hand plant). A reiterative series of leaves was continuously produced from the SAM of the UBI::LpTFL1 plants, most of them with a high density of trichomes (FIG. 8B). The trichome distribution on the surface of the cauline leaves was in general much more dense than in the wild type (FIGS. 8C and 8D). Increased trichome production in relation to TFL1 overexpression in *Arabidopsis* has not previously been reported. The disappearance of adaxial trichomes is a marker for loss of juvenility (Chien and Sussex, 1996; Telfer et al., 1997) and the continuation of trichome production therefore must reflect the vegetative nature of the UBI::LpTFL1 plants. Compared with the wild type, most of the UBI::LpTFL1 plants produced remarkably more and longer internodes on the main stem, and also on the coflorescences. In contrast to the wild-type plants, the uppermost coflorescences without the subtending cauline leaf of the UBI::LpTFL1 plants did not consist of normal solitary flowers, but instead a leaf-like shoot (FIG. 8E).

Based on the time to flowering, the transformants could be grouped into four classes (A-D) displaying a phenotype from late flowering (FIG. 7C, group A) to -never flowering (FIG. 7C, group D). RNA gel-blot analysis revealed that most of the UBI::LpTFL1 plants showed strong expression of LpTFL1 (FIG. 7A, lines 1-31). Overall, the severity of the UBI::LpTFL1 plant phenotypes was positively correlated with the level of LpTFL1 expression in the corresponding plants, and the levels of LpTFL1 expression in the non-flowering lines 2, 7, 9, 11 and 13 were among the highest of all lines tested, The expression level of LpTFL1, in turn, was positively correlated with the total number of gene copies inserted in the genome, as determined by DNA gel-blot analysis (data not shown). In plants with a single-copy insertion (FIG. 7A, lines 5, 16, and 29-30), the LpTFL1 RNA levels were reduced compared with other lines and consequently the phenotype was less severe, but the time to flowering was still significantly longer than in the wild type (FIG. 7C, group A). Three BASTA-resistant plants in which LpTFL1 expression was not detected by gel-blot analysis looked similar to wild-type plants with respect to their morphology, but flowered 10 d later than the wild type (not shown).

LpTFL1 Overexpression in a tfl1-14 Mutant Background

To further address the functional properties of LpTFL1 we asked if LpTFL1 is able to complement the *Arabidopsis* tfl1-14 strong mutant allele. In this mutant a C to T mutation leads to a Thr to iso-Leu substitution at position 69 (FIG. 5B). The tfl1-14 mutant has a short vegetative phase and exhibits reduced plant height with few nodes, increased number of inflorescence arising from the rosette axillary meristems, and a determinate growth pattern (Bradley et al., 1997; Ohshima et al., 1997). The construct used for transformation of the *Arabidopsis* wild type was also used for transformation of the tfl1-14 mutant. More than 100 independent UBI::LpTFL1-tfl1-14 primary transformants were obtained from each mutant line after selection for the binary plasmid. All the plants displayed a variety of phenotypes from wild type to the same extended vegetative phenotype seen in the UBI::LpTFL1 wild-type background. On average (taken only from the first six plants flowering) the UBI::LpTFL1-tfl1-14 plants produced 15.2±3.5 cauline leaves on the main stem and flowered 33 d later than the tfl1-14 mutant and 23 d later than the wild type (FIG. 7C). All the UBI::LpTFL1-tfl1-14 plants grew indefinitely and the production of terminal flowers and rosette inflorescence, which is always seen in the tfl1-14 mutants, was never observed in the transformants. Thus, the LpTFL1 rescued the *Arabidopsis* tfl1-14 mutant in terms of morphology, and further extended the vegetative appearance.

Discussion

Perennial ryegrass is a forage grass with a high agronomic value, since it is a low-cost crop, it is perennial, and it is widely used for feeding cattle. One of the major goals in crop improvement is the control of reproductive growth and flower development. Molecular information on these events is very limited in this species. We have isolated a Plant PEBP gene from perennial ryegrass, which is shown to be a repressor of flowering and involved in control of axillary meristem identity.

*Lolium* LpTFL1 Is a New Member of the Plant PEBP Family

The ryegrass Plant PEBP gene, LpTFL1, encodes a protein with high homology to a group of plant proteins that share structural similarities to mammalian PEBPs. Based on these similarities the plant PEBPs are predicted to play a role in the regulation of signalling cascades as has been shown for the mammalian PEBPs (Yeung et al., 1999; Banfield and Brady, 2000). The two proteins most similar to LpTFL1 are the rice FDR2 and FDR1 with 91% and 86% identity, respectively. In a multiple comparison including Plant PEBP proteins from different species, as well as FT from *Arabidopsis*, LpTFL1 is grouped together with the two rice proteins and a tobacco CEN-like protein, CET1. No data on FDR2/FDR1 expression patterns and functions in rice has been reported, and for CET1, expression has been reported to be detectable in vegetative and inflorescence shoots, but only by RT-PCR (Amaya et al., 1999). Compared with the *Arabidopsis* PEBP sequences, LpTFL1 shows 71% identity to TFL1 and 56% identity to FT. FT, which is 56% identical to the TFL1 protein, also belongs to the family of plant PEBPs, however, in contrast to TFL1, FT has been shown to mediate flowering-inducing signals in *Arabidopsis* (Kardailsky et al., 1999;

Kobayashi et al., 1999). In this process FT acts in parallel with and under the influence of the CONSTANS (CO) gene, which is a mediator of the LD-induction pathway (Samach et al., 2000). LpTFL1 shows 50% identity to a partial FT-like region on a rice clone (nbxb0035E07r), but although the DNA-blot analysis indicates the existence of another LpTFL1-like gene, no ryegrass FT-like cDNA with a higher homology to this partial rice FT-like sequence has yet been identified. Overexpression of LpTFL1 in *Arabidopsis* results in significantly delayed flowering in combination with a dramatic large and bushy phenotype, suggesting that LpTFL1 is more TFL1-like than FT-like.

In spite of the high degree of homology between the plant PEBPs, constitutive expression of these proteins in different plants leads to different phenotypes. The dramatic impact of LpTFL1 overexpression on floral transition and plant architecture in *Arabidopsis* is more extreme than that previously reported by overexpressing TFL1 in *Arabidopsis* (Ratcliffe et al., 1998). It could be speculated that the more severe phenotype observed in our study may be that the activity of the maize ubiquitin promoter is stronger than the 35S CaMV promoter in *Arabidopsis*. However, this would require the monocot ubiquitin promoter having a remarkably strong activity not previously reported in a dicot plant. We suggest that our observation may be due to differences in the protein sequence and conformation of LpTFL1 compared with TFL1. Overexpression of CEN in tobacco has also been reported to significantly delay the floral transition, as well as to change the plant architecture (Amaya et al., 1999). In contrast, there was no effect of overexpressing TFL1 in tobacco (Amaya et al., 1999). These results, together with our results, indicate that differences in the protein sequences among the plant PEBPs are likely to account for the differences observed in the overexpressing plants.

Eleven amino acid residues in the plant PEBP sequences have so far been identified as essential for a functional protein (FIG. 5B) by crystallography (Banfield and Brady, 2000) or by mutations (Bradley et al., 1997; Ohshima et al., 1997; Pnueli et al., 1998). At these residues, LpTFL1 differs from the consensus at one position (110), which is also the position with the highest degree of amino acid variation between species. It is interesting that the variation in amino acid residues at position 110 exactly matches the grouping of plant PEBP by the clustalW alignment (except for FT). One group comprising TFL1, BNTFL1-1, and BNTFL1-3 has a Leu at this position, and another group comprising CEN, CET2, CET4, and SP has a Met, and a third group, which includes LpTFL1, FDR2, FDR1, and CET1, has a Ser at this position. The immediate assumption that the amino acid differences at this position can be linked to the variance in phenotype severity of plants overexpressing different Plant PEBP genes would suggest that overexpression of BNTFL1-1/BNTFL1-3, like TFL1, also has no effect in species like tobacco, and that over-expression of CET1, FDR2/FDR1, like LpTFL1, might have a significant effect on plant architecture and flowering time in species like *Arabidopsis*. Future results on overexpression of Plant PEBP genes in different species would contribute to clarify the correlation between protein sequence and the effect on morphology. In any case, our results show that the effects of different PEBPs cannot solely be explained by genetic diversity, since ryegrass is more distantly related to any of the dicot species, and yet LpTFL1 has a strong and unequivocal effect on the *Arabidopsis*.

Control of Floral Transition

The dramatic phenotype of *Arabidopsis* plants overexpressing LpTFL1 suggests that in ryegrass, LpTFL1 may play a role in controlling meristem identity and in the transition from vegetative to reproductive growth. In ryegrass, LpTFL1 message is detected at all stages from germination to maturity. It is found at the apex, in the inflorescence, and also in leaves, stems, roots, and mature flowers. However, expression of LpTFL1 in the ryegrass apex is not constitutive. Levels of LpTFL1 message changed during flower induction with a slight induction in the SAM after 12 weeks of vernalization, followed by a strong up-regulation during long day (LD) induction until the structures of the spikelets were visible. Unexpectedly, the upregulation of LpTFL1 mRNA during LD induction was even higher in the leaves (more than 25 fold). An increased upregulation of plant PEBPs in the leaves during LD induction has not previously been reported and it strongly suggests that LpTFL1 may play an additional role outside of the SAM. Some of the *Arabidopsis* plants overexpressing LpTFL1 never flowered before senescence. Vegetative non-flowering *Arabidopsis* plants have also been obtained by combining mutations in AP1, CAULIFLOWER (CAL), and FRUITFULL (FUL), all three MADS-box genes (Ferrandiz et al., 2000). The SAM of the ap1, cal, ful triple mutant is arrested in the vegetative to 11 phase, producing only cauline leaves with axillary meristems that in turn repeat this pattern forming "leafy" cauliflower along the main inflorescence (Ferrandiz et al., 2000). Similar cauliflower-like structures were not observed in our UBI::LpTFL1 plants because the repeated formation of meristems was slower. However, an additional morphological characteristic of the UBI::LpTFL1 plants was the high density of trichomes that covered the leaves and the SAM (FIG. 8). In *Arabidopsis*, disappearance of the trichomes from the adaxial surface of cautine leaves has been shown to be tightly linked to floral induction and in support for this observation, it was shown that tfl1 leads to accelerated loss of adaxial trichomes in *Arabidopsis* (Telfer et al., 1997). In agreement with this observation we find that the expression of a Plant PEBP gene in *Arabidopsis* prevents the loss of adaxial trichomes. By this criterion the UBI::LpTFL1 plants were less competent to flower compared with the triple mutant. The UBI::LpTFL1 plants which flowered after an extended vegetative phase produced normal flowers This observation suggests that a delayed, but otherwise normal expression of the floral organ identity genes has occurred. Therefore, the level of LpTFL1 activity can be decreased over time or additional factors override LpTFL1 function and ensure the proper transcription of meristem and organ identity genes. One possible factor is FT, which is able to up-regulate floral meristem identity gene like AP1 and LFY (Kobayashi et al., 1999; Samach et al., 2000).

A Potential Molecular Mechanism for Determinate Plant Architecture in Perennial Ryegrass Perennial ryegrass and *Arabidopsis* represent two different forms of plant architecture: determinate and indeterminate, respectively. A molecular basis for indeterminate growth has been proposed for *Arabidopsis* (Bradley et al., 1996, 1997; Ratcliffe et al., 1998, 1999;) in which indeterminate plant architecture is correlated with expression of TFL1 in the centre of the SAM. In this central region as well as in the uppermost layers of the SAM, TFL1 activity is capable of excluding the expression of AP1 and LFY, and therefore the formation of a terminal flower. In ryegrass, LpTFL1 message is present in the apex at the vegetative stage. Upon LD induction the expression of LpTFL1 is significant upregulation, which is similar to the up-regulation of TFL1 observed in *Arabidopsis* when the plants enter the $I_1$ phase (Ratcliffe et al., 1999). However in addition to what has previously been reported for plant PEBPs, LpTFL1 is strongly upregulated in the leaves during LD induction. Cellular localisation of LpTFL1 expression in the ryegrass apex awaits characterisation, but the present results suggest that ryegrass architecture may be the result of a restriction of LpTFL1 expression in the centre of the SAM to the meristematic ridges of the ryegrass apex (the axillary meristems) and the leaves. Analysis of transgenic ryegrass overexpressing LpTFL1 is in progress, and based on the data presented here we can speculate the following scenario for LpTFL-mediated control of floral transition and plant architecture: Shortly after germination, LpTFL1 expression is established in the meristematic ridges of the apex to maintain the production of vegetative organs such as leaves and tillers. During vegetative growth, a basal level of LpTFL1 and other flowering repressors, perhaps similar to FLC (Michaels and Amasino, 1999), are maintained to avoid precocious flowering before the winter season. During the winter vernalization period, levels of LpTFL1 slightly increase in the apex reflecting an increasing floral competence. As the temperature increases and the photoperiods lengthen in spring, LpTFL1 expression is up-regulated in the apex to promote lateral branching of the main axis. In this way, a maximum number of spikelets are produced. Expression of LpTFL1 subsequently becomes progressively more restricted to vegetative tissues such as leaves, stem and root, and the ryegrass plant finishes its life cycle by the production of the last uppermost seed in the top spike.

2. Overexpression of LpTFL1 in Perennial Ryegrass

Materials and Methods

Ryegrass plant growth conditions, genomic screening, and RNA/DNA analysis were all performed as for example 1 above, with the exception that leaf samples from transgenic ryegrass lines were harvested after 28 ds of secondary induction.

Plant Transformation

The vector for overexpressing LpTFL1 was constructed in the following way: Vector pUC19 was digested with PstI and EcoRI and re-ligated. The cassette of pAHC27 (Christensen and Quail) containing the maize Ubiquitin promoter, its first intron (Ubi1I), the UidA gene, and the NOS terminator, was then ligated into the HindIII site of the modified pUC19. The UL4 gene was removed from the cassette by digestion with SmaI and SstI and following pfu-polishing of the SstI protruding ends, the vector was re-ligated. Finally, the coding region of LpTFL1 cDNA (Jensen et al., 2001) was ligated into the BamHI site of the vector to give pLPTFL1.

pLPTFL1 plasmid was introduced into Lolium perenne together with pAHC20 (Christensen and Quail, 1996) harbouring the Bar gene, which confers resistance to the herbicide BASTA®. For particle bombardment highly embryogenic callus induced from meristems or mature embryos was used. Two different ryegrass cultivars (ACTION and TELSTAR) and one propagated clone (F6). were used as source for the callus production. Isolated embryos and meristems were cultured on a MS-based ((Murashige and Skoog, 1962) callus induction medium (CM) containing 3 % sucrose, 4 mg/l 2,4-dichlorophenoxyacetic acid (2,4-D), 100 mg/l casein hydrolysate and 0.3 % (w/v) gelrite (Kelco) for 12–26 weeks in the dark at 23° C. Calli were maintained by subculturing every third week on fresh CM-medium. Prior to bombardment, an osmotic pre-treatment for 4 hours were given by transferring small calli (2-4 mm) to a solid MS-based medium supplemented with 3 % sucrose, 3 mg/l 2,4-D, 0.25 M sorbitol, 0.25 M mannitol and 0.3% w/v Gelrite. Bombardment was performed with a particle inflow gun (Finer et al., 1992) according to the optimised protocol described by Spangenberg et al. (1995) with a few modifications: bombardment pressure was 8 bar and 300 µg gold particles 0.6 µm (Biorad) were coated with 0.6 µg plasmid DNA (pLPTFL and pAHC20 at a molar ratio of 2:1) according to Vain et al. (1993). The following day, calli were transferred to CM-medium supplemented with 2 mg/l bialaphos (Meiji Seika Kaisha, LTD, Tokyo) and grown at 23° C. under 16 hrs light. Selection at three weeks interval was performed until vigorously growing callus was obtained. Putative transgenic plants were regenerated by transferring calli to hormone free medium RM (MS-medium containing 3% sucrose and 2 mg/l bialaphos). Rooted plantlets were transferred to soil and grown to maturity under greenhouse conditions.

Screening for Stable Transformation

Putative transgenic plants were sprayed twice (two successive days) with a 0.5 % solution of BASTA (Hoechst Schering AgrEvo A/S, Germany) supplemented with 0.1 % Tween 20. The number of herbicide tolerant plants was scored after one week.

PCR Analysis

Genomic DNA was isolated from leaves of primary transformants (T0 generation) by the DNeasy 96 Plant kit (Qiagen), and the presence of the LpTFL1 transgene was determined by PCR using primer LP0 (5'-ATGTCTAG-GTCTGTGGAGCCTC-3') (SEQ ID NO:23)in combination with primer MS8 (5'-ACCGGCAACAGGATTCAATCT-3') (SEQ ID NO:24)to give a 560-bp fragment. Approximately 0.3 µg of genomic DNA was used in each reaction.

Real-Time RT-PCR Analysis

For the detection of LpTFL1 mRNA level in the transgenic ryegrass lines poly-(A)$^+$ mRNA was isolated from crude lysate of approximately 100 mg leaf tissue from one individual per line. Leaf material was harvested prior to the vernalization treatment. Twenty microliter of dynabeads (DYNAL) were used for each mRNA isolation and all the mRNA was used in the reverse transcription. One LpTFL1 primer, INS5' was used in combination with a NOS terminator primer, MS8 in the subsequent Real-time quantitative PCR reaction to amplify a 320 bp LpTFL1 fragment from the first strand cDNA templates. Amplification of PCR products were performed and monitored by the Rotor-Gene (Corbett Research) system in which inclusion of the fluorescent dye SYBR green I dye (Sigma Chemicals) into the reaction mixture facilitates direct measurement of double stranded DNA after each PCR cycle. One microliter of each RT-reaction were used as template in the PCR reaction together with dilutions of plasmids containing LpTFL1 and LpGAPDH (100, 10, 1 and 0.1 pg). In order to normalise the PCR results relative to the initial template amount in each sample, a PCR was run in parallel on similar samples with the primers GAP5 (5'-CAAGGACTGGAGAGGTGG-3') (SEQ ID NO: 19) and GAP3 (5'-TTGACTCGTTGTCGTACC-3') (SEQ ID NO: 20) to amplify a 380 bp LpGAPDH fragment.

Results

Overexpression of LpTFL1 Represses Flowering in Ryegrass.

Thirty six transgenic ryegrass lines were obtained by microprojectile bombardment. All lines were resistant to BASTA®. Plants regenerated from a single transgenic callus (generation $T_0$) were designated as a "transgenic line". Thus, each transgenic line traced back to a different tissue culture and represented an independent transformation event. PCR analyses of transgenic ryegrass leaf DNA using the primers LP0 and MS8 (FIG. 9) showed that the entire LpTFL1 coding region in connection with the NOS terminator was present in 22 lines, giving a 61% co-transformation efficiency. In one line (24), an additional product of 750 bp was amplified by the PCR reaction. Such a product may be amplified by each of the single primers if the transgene had integrated into the genome in a tail-to tail manner. Alternatively, it indicates, that fragmented transgene DNA has been dispersed in the ryegrass genome.

Following three months of vernalization, all transgenic lines (inclusive all the lines which were tested negative for presence of the LpTFL1 transgene and the non-transformed control) were transferred to LD conditions for floral induction. The number of inflorescences varied among the transformed lines with the biggest variation observed between the cultivars. This variance was also observed in the co-transformation efficiency (FIG. 15) and reflects how different the cultivars responded to the transformation event. 'F6' gave the highest co-transformation efficiency (78%) followed by 'ACTION' (76%) and 'TELSTAR' (54%). Among the plants, which were tested negative for the LpTFL1 transgene, 'F6' also produced more flowers (12.3±5.1) than the two other cultivars ('TELSTAR'; 6.0±4.2) and ('ACTION'; 1.4±1.2). 'TELSTAR' and 'F6' in general looked more vigorous than did the cultivar 'ACTION'.

Despite the differences in the number of inflorescences, all the flowering lines headed almost simultaneously with the control after five weeks in LD (not shown). Several lines, however did not flower at all. Of the 22 transgenic lines, which were tested PCR positive for the LpTFL1 transgene, ten remained non-flowering during the flowering season (six months), whereas only two of the 14 PCR negative lines remained non-flowering.

Using real-time RT-PCR we tested, whether the reduction in inflorescence production was correlated with the level of expression of LpTFL1 from the UBI::LpTFL1 transgene. We could detect LpTFL1 transgene expression in 16 of the 22 PCR positive lines. In order to distinguish between the transgene and the endogenous LpTFL1 a NOS terminator primer was used in combination with and internal LpTFL1 primer in the real-time RT-PCR. Subsequent analysis showed that the endogenous LpTFL1 mRNA level in the leaves was 100-fold less than the lowest detected LpTFL1 transgene mRNA level at the point of harvest (not shown). A very high transgene expression level was detected in several lines, and we observed a clear and very dramatic effect of the UBI::LpTFL1 transgene when LpTFL1 was expressed at high levels. Five of the six lines (31, 32, 34, 35, 36) in which we detected the highest LpTFL1 expression did not flower, and nine lines (23, 26, 27, 29, 31, 32, 34, 35, 36) of the 16 LpTFL1 overexpressing lines remained non-flowering throughout the season. Overexpression of LpTFL1 did not cause any other morphological changes when compared to the wild-type.

Discussion

In ryegrass, LpTFL1 message is detected at all stages from germination to maturity. It is found at the apex, in the inflorescence, and also in leaves, stems, roots, and mature flowers. However, expression of LpTFL1 in the ryegrass apex is not constitutive. Levels of LpTFL1 message changed during flower induction with a slight induction in the SAM after 12 weeks of vernalization, followed by a strong up-regulation during long day (LD) induction until the structures of the spikelets were visible. Unexpectedly, the upregulation of LpTFL1 mRNA during LD induction was even higher in the leaves (more than 25 fold). An increased upregulation of plant PEBPs in the leaves during LD induction has not previously been reported and it strongly suggests that LpTFL1 may play an additional role outside of the SAM.

The control of floral transition (ie. the transition from vegetative to reproductive growth) has been studied extensively, especially in Arabidopsis, and a number of key regulators have been identified (for a recent review, see Simpson et al. (1999)). Knowledge of the biological function of these regulators is derived either from mutant studies or from experiments in which these genes were constitutively expressed in annual plants such as Arabidopsis, Antirrhinum, or tobacco. Previous results showed that LpTFL1 is a strong repressor of flowering in annual plants, such as Arabidopsis (Jensen et al., 2001). By introducing LpTFL1 into ryegrass under the control of the maize ubiquitin promoter, we tested whether constitutive expression of LpTFL1 was capable of preventing or inhibiting flowering in a perennial plant. Thirty six transgenic lines were produced of which 22 were tested positive for the LpTFL1 transgene. Flowering was markedly reduced among the PCR positive plants, and ten lines (45%) remained non-flowering during the flowering season. In contrast, only two lines out of the 14 PCR negative lines (14%) were non-flowering.

The level of LpTFL1 expression was tightly linked to the control of the vegetative to the reproductive phase. However, there was no linear correlation between the level of transgene expression and the flowering time (heading date) as previously observed in Arabidopsis (Jensen et. al., 2001), and the floral repression was more seen as reduction in inflorescence production as a delay in heading date. We could detect LpTFL1 transgene mRNA in 16 of the 22 PCR positive lines, and nine of these lines (56%) remained non-flowering. Expression of LpTFL1 at high levels comparable to housekeeping genes such as GAPDH, in this case prevented heading in five out of six lines. No meristem proliferation or stem elongation was observed in the non-heading lines, which indicates that the plants were arrested in the vegetative phase.

Possibly, the control of vegetative to reproductive phase shift in the transgenic ryegrass is mediated by an intracellular LpTFL1 threshold level above which the plants will remain vegetative. Below the threshold level, the plants will flower and LpTFL1 will mainly affect stem length and panicle branching and only secondly the heading date. Unlike Arabidopsis, perennial ryegrass does not flower unless provided with a sufficient cold treatment under the right conditions. Therefore, it is conceivable that either the level of floral repressors are higher in perennials such as ryegrass than in annual plants like Arabidopsis.

It has previously been suggested that vernalization could overcome the activity of 35S::TFL1 in Arabidopsis (Simpson et al., 1999). We found that LpTFL1 was both actively transcribed and functional after three months of vernalization in perennial ryegrass.

The effect of LpTFL1 overexpression was independent of genotype. Three different genotypes were used in the experiment and even though they all responded differently to the transformation with respect to co-transformation efficiency (FIG. 15), the percentage of non-flowering LpTFL1 overexpressing lines were equally distributed among them; ACTION, 55%; TELSTAR, 50%; and F6, 60%.

3. Expression of LpTFL1 in Red Fescue

Materials and Methods

Plant Transformation

The pLPTFL1 plasmid was introduced into red fescue together with pAHC20 (Christensen and Quail, 1996) harbouring the Bar gene, which confers resistance to the herbicide BASTA®. Friable, embryogenic calli, ready for particle bombardment were prepared by growing excised embryos on a MS (Murashige and Skoog, 1962)-based callus-induction medium (MS5) for 10-12 weeks at 25° C. in the dark. The MS5 medium was supplemented with 5 mg/l 2,4-dichlorphenoxyacetic acid (2,4-D), 500 mg/l casein hydrolysate and 3% (w/v) sucrose and solidified with 0.3% gelrite. Prior to bombardment, tissue pieces (34 mm) were transferred for osmotic pre-treatment in liquid medium containing 30 g/l sucrose, 3mg/l 2,4-D, 0.25 M sorbital and 0.25 M mannitol for 30 min, and then transferred to the same medium solidified with 0.3% gelrite and incubated overnight in the dark. Gold particles (1.0 µm), coated with 12 µg of a mixture of pLPTFL1 and pAHC20 at a molar ratio of 1:1 were used for particle bombardment with a Bio-Rad PDS-1000 He Biolistic device (Bio-rad, Hercules, Calif.) at 1300 Psi. Following bombardment, calli were placed on MS5 medium supplemented with 2 mg/l bialaphos (Shinyo Sangyo Ltd., Japan) and grown at 25±1° C. under 16 hrs light. After four to five successive rounds of selection at three weeks interval, putative transgenic plants were regenerated from the calli by supplementing the selection medium with 0.2 mg/l kinetin. Each callus tissue gave between one to four explants, which were transferred to soil and grown to maturity under greenhouse conditions.

Screening for Stable Transformation

All plants, including two non-transformed lines and two lines transformed only with the pAHC20, were screened for phosphinothricin acetyl transferase activity both by the Chlorophenol Red (CR) assay, and by their ability to withstand repeated applications of 5000 ppm BASTA® sprayed onto the foliage. For the CR assay, three to four healthy leaf tips from each plant were incubated on half-strength MS containing 8 g/l agar and 25 mg/l chlorophenol red with or without 8 mg/l bialaphos. Leaves from non-transgenic plants were distinguished from the putative transgenic plants by the development of severe necrosis associated with a characteristic red coloration of the medium.

After six months of growth, plants from each line were vernalized either artificially or under natural field conditions (winter 2000-2001, Denmark). For the artificial vernalization, plants were kept in a growth chamber at or below 5° C. for 21 weeks. During vernalization, the light period was decreased to 8 hrs per day. Following vernalization, all plants were transferred to long day (LD) conditions (16 hrs light at 22 and 20° C., day and night temperature, respectively) for floral induction. After seven months, the clones were cut back and submitted to the second round of floral induction, which included vernalization under natural field conditions (winter 2001-2002) and the subsequent growth in summer conditions. The number of culms with seed head from each individual clone was recorded in both flowering seasons and the length of the five longest inflorescences was measured during the first season.

PCR and DNA Gel Blot Analysis

Genomic DNA was isolated from leaves of primary transformants (T0 generation) by the FastDNA® ORANGE kit DNA isolation system (Bio 101), and the presence of the transgene was determined by PCR. Different primer combinations were used to examine the genomic integration and arrangement of the transgenic DNA (FIG. 16).

The forward primers were MS31 (5'-CGTGGCGGAGCG-GCAGAC-3') (SEQ ID NO: 25), MS33 (5'-TAGTACATC-CATTTAGGGTTTAGG-3') (SEQ ID NO: 26), MS56 (5'-TATTTATTTGCTTGGTACTG-3') (SEQ ID NO: 27) and LP0 (5'-ATGTCTAGGTCTGTGGAGCCTC-3') (SEQ ID NO: 23), and the reverse primers were LP4REV (5'-CGAAC-CTGTGGATACCAATG 3') (SEQ ID NO: 28), LP575 (5'-GGGATCCCACAACTGGGATAGCCAAGAACT-3') (SEQ ID NO: 29) and M58 (5'-ACCGGCAACAGGATTCAATCT-3') (SEQ ID NO: 24).

Genomic DNA for the gel blot analysis was isolated from the leaves of one to three individuals of different transgenic lines by the Phytopure®) Genomic DNA isolation system (Nucleon). DNA (10-30 µg) were digested overnight with restriction endonucleases HinDIII and EcoRI (separately) and fractionated on a 0.8% agarose gel and blotted onto Amersham Hybond N membrane in 20% SSC according to the manufacturer's recommendations. Probe DNA generated by PCR using the primer set MS56-LP4REV on plasmid DNA (FIG. 16) was radiolabeled with $\gamma$-$^{32}$P-labelled dCTP (3,000 Ci/mmol) through the random primer method (Megaprime, Amersham). Pre-hybridisation, hybridisation and the subsequent washing steps were performed according to standard protocols.

RNA Gel Blot Analysis

Seventy five micrograms of total RNA were isolated from leaves of one to four clones from each transgenic line according to Sambrook et al. (1989). Purified poly-A$^+$ mRNA (Dynabeads, DYNAL, Norway) from one individual of each line was fractionated under denaturing conditions and transferred onto Hybond N membranes in 20% SSC. The membranes were hybridised to a 180 bp LpTFL1 cDNA fragment and a 450 bp ACTIN cDNA fragment for standardisation. The other individuals from the transgenic lines were analysed in a similar way, using total RNA. Relative LpTFL1 expression levels in the transgenic lines were estimated on the basis of the results from a density scan (Quantity One software, Biorad) of the autoradiograph in which the LpTFL1 expression level in the highest expressing line (J) was set to 100.

Results

Eighteen transgenic fescue lines were obtained by microprojectile bombardment. In addition, two lines (BAR1 and BAR2) were obtained by transformation only with the plasmid pAHC20. All lines were resistant to BASTA® and showed phosphinothricin acetyl transferase activity. Plants regenerated from a single transgenic callus (generation T$_0$) were designated as a "transgenic line". Thus, each transgenic line traced back to a different tissue culture and represented an independent transformation event. PCR analyses of transgenic fescue leaf DNA using the primers MS56 and LP4REV (FIG. 16) indicated that LpTFL1 was present in 14 lines, giving a 77% co-transformation efficiency. These 14 lines (A-N) together with BAR1, BAR2 and two non-transformed lines were selected for further characterisation.

Transgene Integration

The DNA from the transgenic plants was digested with HinDIII, which released a 2.8-kb fragment containing the ubiquitin promoter and the LpTFL1 coding region (FIG. 16). Restriction patterns of transgenic DNA were complex in several lines (FIG. 10). Restriction fragments of the expected size were found in four lines (D, I, J, and L, FIG. 10A and not shown). All lines contained fragments larger or smaller than the expected size, which represented rearrangements of the transgene DNA. There were no rearranged fragments of the same size recurrently observed in different lines (FIG. 10A) except for a 2.1-kb fragment, which was also present in the controls and may correspond to the endogenous F. rubra TFL1-like (FrTFL1) gene. Faint or smeared signals were also detected in restricted DNA from BAR1 and BAR2 (FIG. 10), which may represent the plasmid pAHC20 that carries the same ubiquitin promoter:exon:intron construct to drive Bar expression.

DNA from transgenic plants was also digested with EcoRI which has only one restriction site in the vector at the 3'-end of the NOS terminator and was expected to yield fragments corresponding in size to the repeats in a pALPTFL1 concatamer if plasmid concatenation had occurred. Multiple different-sized EcoRI restriction fragments hybridising to the intron::LpTFL1 probe (FIG. 10A) indicated that concatenation of full-length plasmid copies was not the predominant mode of transgene organisation in the plant genome. Two lines (D and I) contained fragments of the expected size (5.5 kb), however the subsequent attempt to PCR amplify the transgene promoter in these lines failed (see below). It was difficult to determine the exact transgene copy number especially because several lines contained truncated plasmid copies. Nevertheless, we estimated it to vary from two (line G) to twenty (line D).

Long PCR using different primer combinations to amplify parts of the ubiquitin-exon-intron-LpTFL1-nos cassette (see FIG. 16) was performed to examine if the transgenic lines contained intact cassettes or if transgene rearrangement had occurred internally In this region. The 3'-end of the cassette containing the LpTFL1 coding region and the NOS terminator appeared to be intact in all lines except for A and F (FIG. 16). In addition to the fragments of expected size (0.6 kb), a 0.5 kb fragment was detected in three lines D, G and N, when PCR was performed with the primer set MS56 and LP575. When PCR was performed with the primers LP0 and MS8 we detected fragments larger than the expected size in lines D, I and N. Such fragments may be amplified by each of the single primers if the transgene had integrated into the genome in a tail-to-tail manner. Alternatively, fragmented transgene DNA may have been dispersed in the fescue genome. Smaller fragments must reflect DNA deletions, and since these fragments were only detected when using the primers MS56-Lp4REV and not LP0-MS8, the deletion is likely located in the 3'-end of the ubiquitin intron.

The promoter part of the UBI::LpTFL1 cassette was analysed by PCR using two primers (MS33 and MS31) located 500 and 100 bp upstream the TATA box, respectively, in combination with primers matching the LpTFL1 coding region. The results schematically described in FIG. 16, revealed that two lines (J and L) contained the full-length promoter, while 6 lines only contained a short partial ubiquitin promoter (including the MS31 primer site). In line B, C, E, F, I and K the promoter part was either absent or dispersed and/or reoriented from the LpTFL1 coding region, and in line D and N a 1.5-kb DNA fragment had been deleted between MS33 and LP4REV (including MS31 and the TATA box). A 100 bp deletion was also found in the promoter of lines G, and although the exact location was not determined we assume it to be close to the 3'-end of the UBI intron. The intron part was found to be intact in line A, D, G, H, J, L and M but not in line B, C, E, F, I, K and N (MS31-LP4REV). In all, two lines (J and L) were found to contain at least one complete expression cassette (Ubi-ex-intron-LpTFL1 -nos).

LpTFL1 Expression Represses Flowering.

All transgenic T0 plants grew normally and their morphology did not deviate from the wild-type controls during the vegetative stage (not shown). The morphological differences between the wild-type and the transgenics became apparent after plants had been induced to flowering. The wild-type and the BAR1, BAR2 plants flowered approximately two weeks before the UBI::LpTFL1 plants. The only exception was the plants from line A, which flowered simultaneously with the wild-type. There was a clear difference in the flowering response between the plants, which were vernalized artificially and those, which were vernalized under field conditions (winter 2000-2001). While only two of the artificially vernalized UBI::LpTFL1 lines flowered, ten of the naturally vernalized lines flowered (not shown). Notably, except for one plant, all the artificially vernalized control and BAR1, BAR2 plants flowered (not shown). This observation indicates that although the conditions during the artificial vernalization were sufficient to allow the subsequent flowering induction, the UBI::LpTFL1 lines required stronger environmental stimuli, which were only present under field conditions. For the subsequent analysis of the LpTFL1 transgene effect, we decided to base our results only on the data from the naturally vernalized lines.

The number of inflorescences produced by each clone during the first season varied markedly between the lines (from 0 to 138, FIG. 11A). Fewer inflorescences were produced the second year because the clones were divided into smaller units. Stem (culm) length also varied between the lines, and it did not change significantly from the first to the second flowering season (not shown). Four UBI::LpTFL1 lines (K, L, M and N, FIGS. 11A and B) did not flower during the seven months following the first vernalization, and three of these lines (K, L, and M) also remained non-flowering during the second season. Two lines (I and J) produced only a single flower from three individual clones during the first season and only one and three flowers during the second season, respectively.

RNA gel blot analysis was performed to test whether the reduction and delay in inflorescence production was correlated with the expression of LpTFL1 from the UBI::LpTFL1 transgene. The level of LpTFL1 message varied from zero to levels comparable to ACTIN mRNA (FIG. 12). Three of the four lines (K, L, M) in which the highest LpTFL1 expression was detected did not flower, and the fourth line (J) produced only 0.3 inflorescence per clone (FIGS. 11A and 13). Lines with a lower level of LpTFL1 message produced flowers, and there was a trend (although not statistical significant with the present material) towards a reduction in the number of inflorescences per clone with increasing levels of LpTFL1 mRNA (FIG. 11A).

No LpTFL1 message was detected in line D, F and N (FIGS. 11 and 12). This finding correlated well with the observation that the transgenes in these lines either lacked the UBI promoter (line F) or had a partial UBI promoter lacking the TATA box (line D and N, FIG. 16).

The LpTFL1 message in line A was 80–120 bp smaller than expected (FIG. 12). We propose that this fragment represents a truncated LpTFL1 transcript, which is overexpressed in this line. This assumption is strengthened by the fact that, for this line, we were unable to PCR amplify the LP0-MS8 fragment, which contains the LpTFL1 coding region and the NOS terminator (FIG. 16). In addition, we found that plants from line A flowered simultaneously with the wild-type and produced the highest average number of inflorescences among all the UBI::LpTFL1 lines (FIG. 11A). Line A plants were also among the tallest plants included in the investigation (FIG. 11B), and they produced panicles, which were generally reduced in size compared to the control (FIG. 14). Oppositely, the single flowering plant of the high expressing line J, was the shortest of all flowering plants (FIG. 11A). However, with the present data in hand, there is no statistical significance to confirm a correlation between the level of LpTFL1 expression and culm length.

Discussion

Eighteen Basta® resistant red fescue lines were obtained by particle bombardment. Plants from fourteen different lines were tested positive for the gene of Interest by PCR. DNA gel blot analysis of different lines revealed that the transgene had integrated into the fescue genome in a complex fashion and that multiple transgene rearrangements had occurred. Transgene rearrangements included deletions in the promoter regions and in the LpTFL1 gene (FIG. 16). Highest expression of LpTFL1 was detected in plants containing the full UBI::LpTFL1 cassette. Deletion of promoter sequence lead in most instances to a reduction in LpTFL1 expression compared to the high expressing lines (FIG. 16 and FIG. 11). Expectedly, if the deletion included the TATA box, the partial promoter was defect and no LpTFL1 transcripts could be detected in the plants. However, one line (K) expressed LpTFL1 at high levels although we could not PCR amplify any fragments corresponding to the UBI promoter construct in this line. There is no obvious explanation for this observation, but either none of the three PCR reactions worked or, alternatively, parts of the cassette could have integrated into a transcriptionally active region.

Analysis of the transgenic lines showed that LpTFL1 expression in red fescue is tightly linked to the control of vegetative to reproductive phase shift. All lines containing the LpTFL1 transgene, except line A (discussed below), flowered at least two weeks later than the wild-type and the BAR controls. However, there was no linear correlation between the level of transgene expression and flowering time (heading date) as was previously observed in *Arabidopsis* (Jensen et al., 2001). Expression of LpTFL1 at high levels comparable to housekeeping genes such as ACTIN, in this case prevented heading in three out of four lines and in the fourth line only one inflorescence was produced within three clones (FIGS. 11A and 13). At moderate expression levels, LpTFL1 expression caused a general reduction in the number of inflorescences and in the stem length but an increase in panicle branching, although the statistical significance of these observation requires a more thorough investigation of the second generation plants. Similar observations were made by Nakagawa et al. (2002) in the analysis of transgenic rice overexpressing RCN1/2. They found that constitutive expression of RCN1/2 at moderate levels were associated with a three-fold increase of secondary branches and even production of tertiary branches, which is not seen in wild-type rice. Expression of RCN1/2 at high levels led to stem retardation and a 'never-heading' phenotype. However, the 'never-heading' plants still produced a flag leaf and an immature panicle, enclosed by leaves, indicating that the transition from vegetative to reproductive phase finally took place (Nakagawa et al., 2002). These results are in contrast to our observations, which show that the 'never-heading' red fescue plants presented here, are arrested in the vegetative phase, since they do not produce stems or panicles.

Possibly, the control of vegetative to reproductive phase shift in the transgenic red fescue is mediated by an intracellular LpTFL1 threshold level above which the plants will remain vegetative. Below the threshold level, the plants will flower and LpTFL1 will mainly affect stem length and panicle branching and only secondly the heading date. This correlation is in contrast to the results in *Arabidopsis*, where the flowering date was linearly correlated to the level of LpTFL1 expression (Jensen et al., 2001), and it may reflect the difference in vernalization response between the two species. Both *Arabidopsis* and red fescue are sensitive to vernalization. However, unlike *Arabidopsis*, red fescue does not flower unless provided with a sufficient cold treatment under the right conditions. Therefore, it is conceivable that either the level of floral repressors is higher in red fescue than in *Arabidopsis* or, that the non-flowering threshold level is lower. It has previously been suggested that vernalization could overcome the activity of 35S::TFL1 in *Arabidopsis* (Simpson et al., 1999). We found that LpTFL1 was both actively transcribed and functional even after two rounds of natural vernalization in red fescue.

The molecular function of TFL1-like proteins is not known. Although a putative nucleotide-binding region in TFL1 has been described (Ohshima et al., 1997), recent data suggest that TFL1-like proteins more likely may interfere with regulatory kinase cascades (Banfield and Brady, 2000). Future molecular analysis should concentrate on identifying genes, which are either up- or downregulated in the transgenic fescue lines expressing LpTFL1 at high levels.

Despite the fact that no LpTFL1 expression was detected in line N, these plants remained non-flowering during the first season. It is most likely that this deviation from the other results can be ascribed to the carry-over effects from the tissue culture, since this line started to produce flowers during the second season (FIG. 11A).

The phenotype of the transgenic line A was reminiscent of a putative weak *Festuca rubra* tfl1-like (frtfl1) mutant phenotype. In this line, culm and panicle formation was favoured at the expense of decreased leaf production (FIG. 13), and the panicles were more compressed and wrinkled than the wild-type (FIG. 14). Line C plants in contrast, produced panicles, which were generally larger and contained more spikes with more spikelets than the wild-type panicle. Line C plants expressed LpTFL1 at a relatively high level, suggesting that the increased branching is a direct effect of increased levels of LpTFL1. Consistent with this hypothesis Is the assumption that the decreased branching observed in line A is caused by a C-terminal truncation of the LpTFL1 protein. Interestingly, it was recently found that the function of the proteins belonging to the TFL1 family in *Arabidopsis* is dependent on the C-terminal part of the protein. FLOWERING LOCUS T (FT), which is very homologous to TFL1, but acts oppositely (Kardailsky et al., 1999), is mainly determined by the C-terminal part of the protein. By swapping exons between the FT and TFL1 cDNAs, Ahn and Weigel, (2001) found that the last exon distinguishes between FT- and TFL1 -like properties of the chimeric gene.

In line with our interpretation of the data concerning the line A plants, He et al. (2000) recently reported that overexpression of the *Arabidopsis* LFY from the 35S CaMV promoter lead to early heading in rice. However, early flowering was accompanied by a reduction in grain yield, which was ascribable to smaller panicles containing 7–9 fewer seeds. In addition, He et al. (2000) found that transgenic 35S::LFY plants had on average one or two leaves less than wild-type plants. It has previously been shown that 35S::LFY *Arabidopsis* plants are reminiscent of the tfl1-mutants (Mandel and Yanofsky, 1995; Weigel and Nilsson, 1995) and that mutation in TFL1 leads to ectopic expression of LFY and other floral meristem identity genes in the shoot apex (Bowman et al., 1993; Bradley et al., 1997). Based on these results, we find it reasonable to suggest that the transgenic fescue line A plants are phenotypically reminiscent of the rice 35S::LFY plants and thus may represent a fescue tfl1-like mutant. Analysis of the T1 generation for co-segregation of panicle branching with the UBI::LpTFL1 transgene will reveal if the suggestion is true, and the isolation of a LFY-like (or an AP1-like) gene from red fescue will allow us to determine if the expression level of these floral identity genes are increased in the UBI::LpTFL1 line A plants.

Our results show that expression of the heterologous LpTFL1 in red fescue at high levels can prevent flowering (FIGS. 11A and 12). Additionally, it appears that the level of LpTFL1 expression in flowering plants may cause a reduction in culm length (FIG. 11A) and leaf width (not shown), although this needs to be further examined. No other morphological effects of the transgene expression were observed.

Implementation and utilisation of a LpTFL1-mediated non-flowering phenotype into commercial breeding strategies will require a mechanism, by which the LpTFL1-mediated floral repression can be relieved. Such a mechanism could be provided by combining LpTFL1 expression with the expression of a floral activation gene from a promoter, which can be activated at any time by application of the appropriate ligand.

REFERENCES

Ahn J H, Weigel D (2001). A putative external loop domain in the 4th exon determines functional specificity of FT and TFL1. Abstract in The 12th International Conference on *Arabidopsis* Research, University of Wisconsin, Madison Alvarez J, Guli C L, Yu X, Smyth D R (1992) Terminal flower: a gene affecting inflorescence development in *Arabidopsis thaliana*. Plant J 2:103-116 Amaya I, Ratcliffe O J, Bradley D J (1999) Expression of CENTRORADIALIS (CEN) and CEN-like genes in tobacco reveals a conserved mechanism controlling phase change in diverse species. Plant Cell 11: 1405-1417

Aukermann M j, Amasino R M (1996). Molecular genetic analysis of flowering time in *Arabidopsis*. Semin Cell Dev Biol 7: 4 80-487

Banfield M J, Brady R L (2000) The structure of *Antirrhinum Centroradialis* protein (CEN) suggests a role as a kinase regulator. J Mol Biol 297: 1159-1170

Barnard C (1957) Floral histogenesis in the monocotyledons: I. The Granineae. Aust J Bot 5:115-128

Bowman J L, Alvarez J, Weigel D, Meyrowitz E M, Smyth D (1993) Control of flower development in *Arabidopsis thaliana* by APETALA1 and interacting genes. Development 119: 721-743

Bradley D, Carpenter R, Copsey L, Vincent C, Rothstein S, Coen E (1996) Control of inflorescence architecture in *Antirrhinum*. Nature 376: 791-797

Bradley D, Ratcliffe 0, Vincent C, Carpenter R, Coen E (1997) Inflorescence commitment and architecture in *Arabidopsis*. Science 275: 80-83

Chien J C, Sussex I M (1996) Differential regulation of trichome formation on the adaxial and abaxial leaf surfaces by gibberellins and photoperiod in *Arabidopsis thaliana*. Plant Physiol 111: 1321-1328

Christensen A H, Quail P H (1996) Ubiquitin promoter-based vectors for high-level expression of selectable and/or screenable marker genes in monocotyledonous plants. Trans Res 5: 213-218

Chuang C F, Meyerowitz E M (2000): Specific and heritable genetic interference by double-stranded RNA in *Arabidopsis thaliana*. Proc Natl Acad Sci USA. 97(9): 4985-90.

Chung Y-Y, Kim S-R, Finkel D, Yanofsky M F (1994). Early flowering and reduced apical dominance result from ectopic expression of a rice MADS box gene. Plant Mol Biol 26: 657-665

Clough S J, Bent A F (1998) Floral dip: a simplified method for *Agrobacterium*-mediated transformation of *Arabidopsis thaliana*. Plant J 16: 735-743

Deinum B, Dirven J G P (1975). Climate, nitrogen and grass 6. Comparison of yield and chemical composition of some temperate and tropical species grown at different temperatures. Neth J Agric Sci 23: 69-82

Delagarde R, Peyraud J L, Delaby L, Faverdin P (2000). Vertical distribution of biomass, chemical composition and pepsin-cellulase digestibility in a perennial ryegrass sward: interaction with month of year, regrowth age and time of day. Anim Feed Sci Technol 84: 49-68

Ferrandiz C, Gu Q, Martienssen R, Yanofsky M F (2000) Redundant regulation of meristem identity and plant architecture by ERUITEULL, APETALAI, and CAULIFLOWER. Development 127: 725-734

Finer, J. J., Vain, P., Jones, M. W. and M. D. McMullen. 1992. Development of the particle inflow gun for DNA delivery to plant cells. Plant Cell Rep. 11: 323-328.

Gustafson-Brown C, Savidge B, Yanofsky M F (1994) Regulation of the floral homeotic gene APETALA 1. Cell 76: 131-143

He Z, Zhu Q, Dabi T, Li D, Weigel D, Lamb C (2000). Transformation of rice with the *Arabidopsis* floral regulator LEAFY causes early heading. Trans Res 9: 223-227

Hiei et al. (1994) Plant Journal 6, 271-282

Jensen C S, Salchert K, Nielsen K K (2001). A TERMINAL ELOWER1-like gene from perennial ryegrass involved in floral transition and axillary meristem identity. Plant Physiol 125: 1517-1528

Kang H. G, Jang 5, Chung J-E, Cho Y G, An G (1997). Characterisation of two rice MADS box genes that control flowering time. Mol Cells 7: 559-566

Kardailsky I, Shukla V K, Ahn J H, Dagenais N, Christensen S K, Nguyen J T, Chory J, Harrison M J, Weigel D (1999) Activation tagging of the floral inducer FT. Science 286: 1962-1965

Kobayashi Y, Kaya H, Goto K, Iwabuchi M, Araki T (1999) A pair of related genes with antagonistic roles in mediating flowering signals. Science 286:1960-1962

Koncz C, Schell J (1986) The promoter of the $T_L$-DNA gene 5 controls the tissue-specific expression of chimeric genes carried by a novel type of *Agrobacterium* binary vector. Mol Gen Genet 204: 383-396

Mandel M A, Gustafson-Brown C, Savidge B, Yanofsky M F (1992) Molecular characterisation of the *Arabidopsis* floral homeotic gene APETALA1. Nature 360: 273-277

Mandel M A, Yanofsky M F (1995) A gene triggering flower formation in *Arabidopsis*. Nature 377: 522-524

Michaels S D, Amasino R M (1999). FLOWERING LOCUS C encodes a novel MADS domain protein that acts as a repressor of flowering. Plant Cell. 11: 949-956

Mimida N, Sakamoto W, Murata M, Motoyoshi F (1999) TERMINAL FLOWER1-like genes in *Brassica* species. Plant Sci 142: 155-162

Murashige T, Skoog F (1962). A revised medium for rapid growth and bioassays with tobacco tissue cultures. Physiol Plant 15: 473 -497

Nakagawa M, Shimamoto K, Kyozuka J (2002). Overexpression of RCN1 and RCN2, rice TERMINAL FLOWER 1/CENTRORADIALIS homologs, confers delay of phase transition and altered panicle morphology in rice. Plant J 29: 743-750

Oba M, Allen M S (1999). Evaluation of the importance of the digestibility of neutral detergent fibre from forage: effects on dry matter intake and milk yield of dairy cows, J Dairy Sci 82: 589-96

Ohshima S, Murata M, Sakamoto W, Ogura Y, Motoyoshi F (1997) Cloning and molecular analysis of the *Arabidopsis* gene Terminal Flower1. Mol Gen Genet 254:186-194

Pnueli L, Carmel-Goren L, Hareven D, Gutfinger T, Alvarez J, Ganal M, Zamir D, Lifschitz E (1998) The SELFPRUNING gene of tomato regulates vegetative to reproductive switching of sympodial meristems and is the ortholog of CEN and TFL1. Development 125: 1979-1989

Poethig R S (1990) Phase change and the regulation of shoot morphogenesis in plants. Science 250: 923-930

Ratcliffe O J, Amaya I, Vincent C A, Rothstein 5, Carpenter R, Coen ES, Bradley D J (1998) A common mechanism controls the life cycle and architecture of plants. Development 125: 1609-1615

Ratcliffe O J, Bradley D J, Coen E S (1999) Separation of shoot and floral meristem identity in *Arabidopsis*. Development 126:1109-1120

Samach A, Onouchi H, Gold S E, Ditta G S, Schwartz-Sommer Z, Yanofsky M F, Coupland G (2000) Distinct roles of CONSTANS target genes in reproductive development of *Arabidopsis*. Science 288:1613-1616

Sambrook J, Fritsch E F, Maniatis T (1989). Molecular cloning: a laboratory manual. Cold Spring Harbor Laboratory Press, NY Shanon S, Meek-Wagner D R (1991) A mutation in the *Arabidopsis* TFL1 gene affects inflorescence meristem development. Plant Cell 3: 877-892

Sharp P A (1999) RNAi and double-strand RNA. Genes Dev. 13(2): 139-41.

Sheldon C S, Burn J E, Perez P P, Metzger J, Edwards J A, Peacock W J, Dennis E S (1999) The FLF MADS box gene: a repressor of flowering in *Arabidopsis* regulated by vernalization and methylation. Plant Cell 11: 445-458

Simpson G G, Gendall A R, Dean C (1999) When to switch to flowering. Annu Rev Cell Dev Biol 99: 519-550

Spangenberg, G., Wang, Z. Y., Wu, X. L., Nagel, J., Iglesias, V. A. and 1. Potrykus. 1995. Transgenic tall fescue (*Festuca arundinacea*) and red fescue (*F. rubra*) plants from microprojectile bombardment of embryogenic suspension cells. J. Plant Physiol. 145: 693-701.

Telfer A, Bollman K M, Poethig R S (1997) Phase change and the regulation of trichome distribution in *Arabidopsis thaliana*. Development 124: 645-654

Tingay et al. (1997) Plant Journal 11,1369-1376

Vasil (1994) Plant Mol. Biol. 25, 925-937

Weberling F (1989) Morphology of Flowers and Inflorescences. Cambridge University Press, Cambridge, UK Weigel D, Nilsson O (1995) A developmental switch sufficient for flower initiation in diverse plants. Nature 377: 495-500

Wilman D, Ojuederie B M, Asare E O (1976). Nitrogen and Italian ryegrass III. Growth up to 14 weeks: yields, proportions, digestibilities and nitrogen contents of crop fractions, and tiller populations. J Br Grassl Soc 31: 73-79

Yeung K, Seitz T, Li S F, Janosh P, McFerran B, Mischak H, Sedivy J M, Kolch W (1999) Suppression of Raf-1 kinase activity and MAP kinase signaling by RKIP. Nature 401: 173-177

The invention claimed is:

1. A method of reducing or preventing flowering in a plant, the method comprising expressing a polynucleotide comprising a heterologous nucleotide sequence selected from the group consisting of:
   (a) nucleotide sequences encoding a polypeptide having the amino acid sequence as shown in SEQ ID NO: 3;
   (b) the coding sequence shown in SEQ ID NO: 1 or SEQ ID NO: 2; and
   (c) nucleotide sequences having at least 95% identity with the nucleotide sequence of (a) or (b) wherein said nucleotide sequences encode a polypeptide comprising the amino acid sequence YESP(K/R), of SEQ ID No. 30 or 31 and which, when expressed, extends the vegetative-inflorescence phase, increases lateral branching, represses flowering in said plant in the first year of growth, and/or represses flowering in said plant after the first year of growth.

2. The method of claim 1, wherein the polynucleotide defined in section (c) has a percentage value of identity with the sequence of (b) selected from the group consisting of 95%, 97% and 99%.

3. The method of any one of claims 1 to 2, wherein the polypeptide encoded by said polynucleotide fragment includes the sequence YESP(K/R) located between residues about 100 and about 120 of SEQ ID NO: 3.

4. The method of any one of claims 1 to 2, wherein said plant is a biennial or a perennial.

5. The method according to claim 4, wherein said plant is a perennial.

6. The method according to any one of claims 1 to 2, wherein said plant is selected from the group consisting of crops belonging to the grass family of *Poaceae*; soybean; potato; oilseed rape; sunflower; alfalfa; sugar cane; cotton; herbs; fruits and vegetables; rosaceous fruits; vegetable brassicas; and woody species.

7. The method according to any one of claims 1 to 2, wherein said plant is a monocot plant.

8. The method according to claim 1, the method comprising inserting an expression cassette which comprises a promoter operably linked to the polynucleotide as defined in claim 1 into a plant host cell, growing the said transformed host cell in a suitable culture medium to produce a plant that expresses said polynucleotide to produce the protein encoded by said polynucleotide, and wherein said expressed protein reduces or prevents flowering in said plant.

9. The method according to claim 8, wherein said promoter is selected from the group consisting of a constitutive promoter, an inducible promoter and a developmentally regulated promoter.

10. The method according to claim 8, wherein said promoter is selected from the group consisting of the monocot and dicot actin and ubiquitin promoters, monocot and dicot glyceraldehyde dehyrogenase (GAPDH) promoters, the cauliflower mosaic virus 35S (CaMV 35S) and 19S (CaMV 19S) promoters, the 35S CaMV promoter containing the translational enhancer (TMV omega element), the nopaline synthase (NOS) promoter, the octopine synthase (OCS) promoter.

11. A transgenic plant transformed with the polynucleotide as defined in claim 1 or the expression cassette as defined in claim 8.

12. The transgenic plant according to claim 11, wherein said plant is a biennial or a perennial.

13. The transgenic plant according to claim 12, wherein said plant is a perennial.

14. The transgenic plant according to claim 11, wherein said plant is selected from the group consisting of crops such as those belonging to the grass family of *Poaceae*; soybean; potato; oilseed rape; sunflower; alfalfa; sugar cane; cotton; herbs; fruits and vegetables; rosaceous fruits; vegetable brassicas; and woody species.

15. The transgenic plant of claim 11, which is a monocot plant.

16. The method of claim 1, wherein the polynucleotide defined in section (c) has 95% sequence identity with the sequence of (b).

17. The method of claim 1, wherein the polynucleotide defined in section (c) has 100% sequence identity with the sequence of (b).

18. The method according to claim 16 or 17 wherein said plant is a plant belonging to the grass family of *Poaceae*.

19. The method according to claim 6, wherein said herbs are selected from the group consisting of anise, basil, bay laurel, caper, caraway, cayenne pepper, celery, chervil, chives, coriander, dill, fennel, garlic, horseradish, leeks, lemon balm, liquorice, marjoram, mint, oregano, parsley, rosemary, sesame, tarragon and thyme.

20. The method according to claim 6, wherein said fruits and vegetables are selected from the group consisting of banana, blackberry, blueberry, strawberry, raspberry, carrot, coffee, eggplant, grapes, honeydew, mango, onion, papaya, peas, peppers, and pineapple.

21. The method according to claim 6, wherein said rosaceous fruits are selected from the group consisting of apple, peach, pear, cherry and plum.

22. The method according to claim 6, wherein said vegetable brassicas is brussel sprouts.

23. The method according to claim 6, wherein said woody species is selected from the group consisting of eucalyptus, oak, pine, and poplar.

24. The plant according to claim 14, wherein said plant is a plant belonging to the grass family of *Poaceae*.

25. The plant according to claim 14, wherein said herbs are selected from the group consisting of: anise, basil, bay laurel, caper, caraway, cayenne pepper, celery, chervil, chives, coriander, dill, fennel, garlic, horseradish, leeks, lemon balm, liquorice, marjoram, mint, oregano, parsley, rosemary, sesame, tarragon and thyme.

26. The plant according to claim 14, wherein said fruits and vegetables are selected from the group consisting of: banana, blackberry, blueberry, strawberry, and raspberry, carrot, coffee, eggplant, grapes, honeydew, mango, onion, papaya, peas, peppers, pineapple.

27. The plant according to claim 14, wherein said rosaceous fruits are selected from the group consisting of: apple, peach, pear, cherry and plum.

28. The plant according to claim 14, wherein said vegetable brassicas is brussel sprouts.

29. The plant according to claim 14, wherein said woody species is selected from the group consisting of: eucalyptus, oak, pine, and poplar.

30. The plant according to claim 24, wherein the polynucleotide defined in section (c) has 95% identity with the nucleotide sequence of (a) or (b), wherein said nucleotide sequences encode a polypeptide comprising the amino acid sequence YESP(K/R) of SEQ ID No. 30 or 31 and wherein said plant possesses extended vegetative-inflorescence phase, increased lateral branching, repressed flowering in the first year of growth, and/or repressed flowering after the first year of growth.

31. The plant according to claim 24, wherein the polynucleotide defined in section (c) has 100% identity with the nucleotide sequence of (a) or (b) wherein said nucleotide sequences encode a polypeptide having LpTFL1-like activity and comprising the amino acid sequence YESP(K/R) of SEQ ID No. 30 or 31 in said plant.

32. A transgenic plant comprising a first and a second polynucleotide, wherein
  (i) said first polynucleotide is selected from the group consisting of:
    (a) nucleotide sequences encoding a polypeptide having the amino acid sequence as shown in SEQ ID NO: 3;
    (b) the coding sequence shown in SEQ ID NO: 1 or SEQ ID NO: 2; and
    (c) nucleotide sequences having at least 95% identity with the nucleotide sequence of (a) or (b) wherein expression of said nucleotide sequence extends the vegetative-inflorescence phase, increases lateral branching, represses flowering in said plant in the first year of growth, and/or represses flowering in said plant after the first year of growth, and
  (ii) said second polynucleotide is capable of regulating expression of said first polynucleotide sequence, and
  wherein at least one of said first and second polynucleotide sequences is heterologous to said plant.

33. The transgenic plant according to claim 32, wherein said plant is a biennial or a perennial.

34. The transgenic plant according to claim 32, wherein said plant is selected from the group consisting of crops such as those belonging to the grass family of *Poaceae*; soybean; potato; oilseed rape; sunflower; alfalfa; sugar cane; cotton; herbs; fruits and vegetables; rosaceous fruits; vegetable brassicas; and woody species.

35. The transgenic plant of claim 32, which is a monocot plant.

* * * * *

```
                        SEQUENCE LISTING

<160> NUMBER OF SEQ ID NOS: 31

<210> SEQ ID NO 1
<211> LENGTH: 929
<212> TYPE: DNA
<213> ORGANISM: Lolium perenne

<400> SEQUENCE: 1
gcccaagcca cttcaaagct tgctactac cagatagagc attcaccgtg caatatagaa      60
atacttgcct ctccaaccat gtctaggtct gtggagcctc ttattgttgg tcgtgtcatt    120
ggagaagttc tcgatccatt taacccatgt gtgaagatgg tagcaaccta taactcaaac   180
aagctggtct tcaatggtca tgagctctac ccatcagcag ttgtatctaa accaagagta    240
gaggttcagg ggggtgactt gcgatcctta ttcacattgg ttatgacgga cccagatgtg    300
ccaggaccaa gtgatccgta tctgcgggag catcttcact ggattgtcag taatatacct    360
gggacaacag atgcttcatt tgggggggag gtcatgagct atgagagccc aaagcccaac    420
attggaatcc acaggttcat ttttgtgctc ttcaagcaga agcgaaggca gactgtatct    480
gtgccttcct tcagggatca tttcaacacc cgccagtttg ctgtggataa tgatcttggc    540
ctccctgtgg ctgctgttta cttcaattgt cagagagaga ctgctgccag gaggcgctga    600
aaatcgagtt cttggctatc ccagttgtgc caaataaagg cttttggagt tatgcacctt    660
ctttctgaag tcaatgctcc tcttctacat tacttcctcg tggaccattg cttctttact    720
acagtttttg ctcagggatc aaataaatca agtgcatttt ggagattgta ttagattata    780
ttgtaagcag tgagatcagc aaccatgtgt taacataagc cagtacatta gcaggtccat    840
gtttatggtt tcatgttgtg tgtaagcagt tatcactaga aggaaggtca ggtagacaac    900
ccaaactggc aaaaaaaaag ctttatcta                                      929
```

<210> SEQ ID NO 2
<211> LENGTH: 5224
<212> TYPE: DNA
<213> ORGANISM: Lolium perenne

<400> SEQUENCE: 2

| | | | | | |
|---|---|---|---|---|---|
| cactagtaac | ggccgccagt | gtgctggaat | tcagggtaat | acgactcact | ataggmgct 60 |
| cgaggatctt | cccaccagtg | tgcattcatg | tgttacttac | cactctccaa | cttgagggac 120 |
| tcaagattgg | tgggcggctc | cttttcgctg | aagcgatcca | aaggtgtcgg | gtaacggtta 180 |
| tgacagcaaa | cagaaaacat | cgccatctgc | acggaagcca | gaagtagtta | ctatgtcaaa 240 |
| gggatataaa | aaactcacta | atgaaggggg | atgctattgc | tgagataaac | tgctatctca 300 |
| tctacaggtg | agattgcaag | tatacttgac | aacaggcca | gatggtatgg | catgaagaaa 360 |
| attagggctg | gagtagaaag | gtaagatatg | catggatttg | gatgagatgg | ctagagggtt 420 |
| gcgagatatc | aaatagaaga | cacttcttca | atgattcaat | agaagatgca | tgtgccatta 480 |
| cagagtggat | tattatgtcc | ttttaaaga | gatgcttacg | tccctgacct | ttcctataac 540 |
| acaattacac | tcctttgcta | gacttttcct | gctataattg | tctttcctcg | ccaaaagaat 600 |
| aatactatag | aacttcctaa | tttaatttcc | ccttatttc | ttggactcta | tcttaattct 660 |
| cctcctattg | ttcagccaag | gactgctcct | tccatttact | tgcgccacgg | gctgactgac 720 |
| aatgacacct | gcgcgctttg | tgatcaagag | cctgaatcta | tttctcacct | catgctgcaa 780 |
| tgctccttct | cacagcaaat | atggtatgat | atctgcagta | agctcaacct | tctgccatgt 840 |
| atgccagttg | gcaacgccga | gttcagcatt | tggttcgccg | cagctgccgc | caacgctcaa 900 |
| ccagccctgc | agaagggtgc | taaatccatc | atcatcctta | ctctctggag | attatggaag 960 |
| acgaggaacg | atgctatctt | caaaaatctg | gcccccaaca | gactcgcctt | agttcagtcg 1020 |
| atcctagatg | aagcctgtca | atggtcgtta | gccggtgcta | aggcgctacg | tcagttacct 1080 |
| ttacatgcta | gaccccctga | tgttagcctt | gatgaggaac | tctaggtcta | actaagttag 1140 |
| ccctgtacag | tttttttttc | tcttttcctt | ttctttttt | tgctttctct | tcttttcgtt 1200 |
| tttggtagct | ttgctactct | tgtatgctcc | cgtcttctcg | acggcttctt | ctaatatata 1260 |
| atgacgcatg | ctttggcatg | tgttcgagaa | aaaaatttac | ttacctctta | ggctatattc 1320 |
| tcttcaccaa | cttggactcc | acaaagcttc | aatcgcaact | tgtccaagct | gctgccgctg 1380 |
| gtgctgctgt | ccttttccaa | tgcatccata | cactgtccta | gtcagcatac | caaacaaaaa 1440 |
| agctaatgcc | gccctgttg | tttcaaatga | attatctgat | tgtgatgctg | ctaatctttt 1500 |
| gcatatgagt | ctcgggcata | tgaatgaact | tggtttggca | gaatgaaaca | agagaggact 1560 |
| tcttgatgga | tatagcactg | gtaagctgaa | gttctgtgag | caggctatga | tgttcccctg 1620 |
| ttaaaaaaaa | ggctatgaaa | aacttgtgat | aggtgttaag | tattggtttt | attttgcgtg 1680 |
| caaattggta | tgcatgaaaa | gttgtagtgc | tactagtctg | tggtgctact | gtgctaccaa 1740 |
| cacactgtag | cactgccaaa | aatttatgaa | aaagtctgaa | cagacgagat | gtatctatca 1800 |
| attcatggac | ccattttgtt | ataatttct | tttaaataa | aaaattccgt | aaagaatcaa 1860 |
| taagtggaat | tattggaaat | gaaaaaagta | accaaaatac | taaactttt | ttcaaataca 1920 |
| gatcggatat | catggagaca | cactggctac | cattggttgg | aatagctact | agattccact 1980 |
| acagctaggt | gtcaagcaac | tataatggca | tcagaatgga | gcagaaaaat | gtcacaagct 2040 |
| gtacttcact | ccactacttc | tagctgcaca | aatgtcaagc | aggcatgatt | gcactagacc 2100 |
| agaacatagt | aatgcataaa | gctgtaattg | gctccactac | ttatggaaac | gaagaaatct 2160 |

```
attatttatt gttttaatcg agatgaagct gtgataattt tatcgctgaa atgacatttc     2220
agcactagac agcaccctag acaattaagt ggtggtggca ctgtattcca ttcctttatt     2280
ctcttccatg gtgtgttccc atagtactac aaagaagaga ataaacagat aataatggta     2340
atgcacttgg gtatcgaagt tttaggaaag attctaattc tagagcaatt gaactcaaca     2400
acaacttccc ttttccttaa cagaaaaaga atcggtcaaa cgaggcttgc ctaaaccaac     2460
aacactataa agacgaacat tgagggtga agaggcttcc acgtggacag tgccgcatgt      2520
ttctgtccac tagataacac ctaaataata gttaaaaaac aagaggataa gaatatcaga     2580
aagccagacc ttaaatttct gcaagcaaac atcaaatgaa gtatgcaaaa acgaattgat     2640
agtttaggaa agcatcactc caaagtgttt tattcccgtt cttttcatt tgctccacaa      2700 gggcatactt cctaaatttc tgcgaacaat tacatctaga tcttttaaa actgaagtat      2760 tttagcatga aaacgcattg ttctgtaatg tggctgtgaa tttcggactg ctcatctgat     2820
ttccctctgg tagaatacat aaataattat acacaacagc atgataatgt gcaaaactaa    2880
gcatcaaaat ctgcacattg tcatgcagaa actaggacag gaggaccagc actttgtcgt     2940
ttgtcctaac caatattaac atagttcagc aacataatct tcagagaccc actagcatga    3000
aggtgtgtta tgtttcctaa agaaataaca tgtaggtagt gatctacaat accttttttg    3060
gggactataa ggtgggaaac catcaacttg aaaaggtttc catttaatca agtaaaaaaa    3120
acagtatttt ttaactatca ataactaaaa ttaaaacaga atagagatat actaacaatg    3180
aaaatcaaac agttgtgcaa attgtattta tcgtagttag tatctcatgt ttctggtgaa    3240
aaaattctct gccccctagaa cttggaagaa gatgcatgaa gtattactcc aaactccaac   3300
actgtgcaac tgatagaaaa gaaacaagac ccttggttgg ctgtctcgga aaaagtggtt    3360
aggtcctttc tgtggccttt tcagttcttt ccacgcatac ccaaccaaaa aagaacacag    3420
atactactca tgtctcacat tctcttttga gcttacactc gaagcaggct tcttgcctct    3480
ataagtagag gctcgtcgta ctctagcaat gctcagtaag cagcccaagc cacttcaaag    3540 cttgctact accagataga gcattcaccg tgcaatatag aaatacttgc ctctccaacc     3600
atgtctaggt ctgtggagcc tcttattgtt ggtcgtgtca ttggagaagt tctcgatcca    3660
tttaacccat gtgtgaagat ggtagcaacc tataactcaa acaagctggt cttcaatggt    3720
catgagctct acccatcagc agttgtatct aaaccaagag tagaggttca ggggggtgac    3780
ttgcgatcct tattcacatt ggtagaatgc actcgactcg atcttggaac tccatattca    3840
acttcgagta ttgtatgctt gttttcttct ttcgcagtgg ccataattat tcatatttca    3900
ggttatgacg gacccagatg tgccaggacc aagtgatccg tatctgcggg agcatcttca    3960
ctggtaacct ttctcatgca cagttttttc tgctgggtgg ctactaagca cctaaatata    4020
ttagtatatt tttttgaaag gaaaatatat tagtatatgt tgctaaggaa tatagaagta    4080
catcttcttc ttgcacatat atagacagag agactatttt aatagcactt ctaacgagag    4140
tcatttacca ataccttta cacttacaca ggattgtcag taatatacct gggacaacag     4200
atgcttcatt tggtaggtcc ttctctgaga tttgaattgg tatattctat gttctgcatt    4260
ttgaatgaat aaccactgac cttttgaatt gcagggggg aggtcatgag ctatgagagc     4320
ccaaagccca acattggaat ccacaggttc attttttgtgc tcttcaagca gaagcgaagg   4380
cagactgtat ctgtgccttc cttcagggat catttcaaca cccgccagtt tgctgtggat    4440
aatgatcttg gcctccctgt ggctgctgtt tacttcaatt gtcagagaga gactgctgcc    4500
```

-continued

```
aggaggcgct gaaaatcgag ttcttggcta tcccagttgt gccaaataaa ggcttttgga    4560
gttatgcacc ttctttctga agtcaatgct cctcttctac attacttcct cgtggaccat    4620
tgcttcttta ctacagtttt tgctcaggga tcaaataaat caagtgcatt ttggagattg    4680
tattagatta tattgtaagc agtgagatca gcaaccatgt gttaacataa gccagtacat    4740
tagcaggtcc atgtttatgg tttcatgttg tgtgtaagca gttatcacta gaaggaaggt    4800
caggtagaca acccaaactg gcaaaaaaaa aagcttatc tactgtatgg cccttgccgg     4860
cttgatgttc catgcacctt ttctgacatg ctgtctactg tatgccaccg ccactataat    4920
gtatgagata tgaatataaa atggagatat ccaaaatatc cagatgattg cccactaaat    4980
gctaaatgta catagtgggt tttccaccta ttttgacttc atcatgtcct tacacaaaat    5040
cagaaaacat ccatttcatg cacattgatg cacactgcat attaacaatc tattcagatt    5100
tggctgtaaa cacacccta ttttccgcat ccattaatat tatattagta ccctggacag     5160
gttaagcttt tgcagcacag taagtaaccg gatgaaatta caatatgatc ctcgagcgcc    5220
ctat                                                                 5224
```

<210> SEQ ID NO 3
<211> LENGTH: 173
<212> TYPE: PRT
<213> ORGANISM: Lolium perenne

<400> SEQUENCE: 3

```
Met Ser Arg Ser Val Glu Pro Leu Ile Val Gly Arg Val Ile Gly Glu
1               5                   10                  15

Val Leu Asp Pro Phe Asn Pro Cys Val Lys Met Val Ala Thr Tyr Asn
            20                  25                  30

Ser Asn Lys Leu Val Phe Asn Gly His Glu Leu Tyr Pro Ser Ala Val
        35                  40                  45

Val Ser Lys Pro Arg Val Glu Val Gln Gly Gly Asp Leu Arg Ser Leu
    50                  55                  60

Phe Thr Leu Val Met Thr Asp Pro Asp Val Pro Gly Pro Ser Asp Pro
65                  70                  75                  80

Tyr Leu Arg Glu His Leu His Trp Ile Val Ser Asn Ile Pro Gly Thr
                85                  90                  95

Thr Asp Ala Ser Phe Gly Gly Glu Val Met Ser Tyr Glu Ser Pro Lys
            100                 105                 110

Pro Asn Ile Gly Ile His Arg Phe Ile Phe Val Leu Phe Lys Gln Lys
        115                 120                 125

Arg Arg Gln Thr Val Ser Val Pro Ser Phe Arg Asp His Phe Asn Thr
    130                 135                 140

Arg Gln Phe Ala Val Asp Asn Asp Leu Gly Leu Pro Val Ala Ala Val
145                 150                 155                 160

Tyr Phe Asn Cys Gln Arg Glu Thr Ala Ala Arg Arg Arg
                165                 170
```

<210> SEQ ID NO 4
<211> LENGTH: 177
<212> TYPE: PRT
<213> ORGANISM: Arabidopsis sp.

<400> SEQUENCE: 4

```
Met Glu Asn Met Gly Thr Arg Val Ile Glu Pro Leu Ile Met Gly Arg
1               5                   10                  15

Val Val Gly Asp Val Leu Asp Phe Phe Thr Pro Thr Thr Lys Met Asn
```

-continued

```
                  20                  25                  30
Val Ser Tyr Asn Lys Lys Gln Val Ser Asn Gly His Glu Leu Phe Pro
            35                  40                  45
Ser Ser Val Ser Ser Lys Pro Arg Val Glu Ile His Gly Gly Asp Leu
        50                  55                  60
Arg Ser Phe Phe Thr Leu Val Met Ile Asp Pro Asp Val Pro Gly Pro
65                  70                  75                  80
Ser Asp Pro Phe Leu Lys Glu His Leu His Trp Ile Val Thr Asn Ile
                85                  90                  95
Pro Gly Thr Thr Asp Ala Thr Phe Gly Lys Glu Val Val Ser Tyr Glu
            100                 105                 110
Leu Pro Arg Pro Ser Ile Gly Ile His Arg Phe Val Phe Val Leu Phe
        115                 120                 125
Arg Gln Lys Gln Arg Val Ile Phe Pro Asn Ile Pro Ser Arg Asp
130                 135                 140
His Phe Asn Thr Arg Lys Phe Ala Val Glu Tyr Asp Leu Gly Leu Pro
145                 150                 155                 160
Val Ala Ala Val Phe Phe Asn Ala Gln Arg Glu Thr Ala Ala Arg Lys
                165                 170                 175
Arg

<210> SEQ ID NO 5
<211> LENGTH: 178
<212> TYPE: PRT
<213> ORGANISM: Brassica napus

<400> SEQUENCE: 5

Met Glu Asn Met Gly Thr Arg Val Ile Glu Pro Leu Ile Val Gly Arg
1               5                   10                  15
Val Val Gly Asp Val Leu Asp Asn Phe Thr Pro Thr Ile Lys Met Asn
            20                  25                  30
Val Ser Tyr Asn Lys Lys Gln Val Ser Asn Gly His Glu Leu Phe Pro
        35                  40                  45
Leu Ala Val Ser Ser Lys Pro Arg Val Glu Ile His Asp Gly Asp Leu
    50                  55                  60
Arg Ser Phe Phe Thr Leu Val Met Thr Asp Pro Asp Val Pro Asn Pro
65                  70                  75                  80
Ser Asp Pro Phe Leu Lys Glu Arg Leu His Trp Leu Val Met Asn Ile
                85                  90                  95
Pro Gly Thr Thr Asp Ala Thr Phe Gly Lys Glu Val Val Ser Tyr Glu
            100                 105                 110
Leu Pro Lys Pro Asn Ile Gly Ile His Arg Tyr Val Phe Val Leu Phe
        115                 120                 125
Arg Gln Lys Gln Arg Val Lys Phe Pro Ser Asn Ile Ile Ser Arg
130                 135                 140
Asp Gln Phe Asn Thr Arg Glu Phe Ala Ile Glu Asn Asp Leu Gly Leu
145                 150                 155                 160
Pro Val Ala Ala Val Phe Phe Asn Ala Gln Arg Glu Thr Ala Ser Arg
                165                 170                 175
Arg Arg

<210> SEQ ID NO 6
<211> LENGTH: 178
<212> TYPE: PRT
<213> ORGANISM: Brassica napus
```

```
<400> SEQUENCE: 6

Met Glu Asn Met Gly Thr Arg Val Ile Glu Pro Leu Ile Val Gly Arg
1               5                   10                  15

Val Val Gly Asp Val Leu Asp Asn Phe Ala Pro Thr Ile Lys Met Asn
            20                  25                  30

Val Ser Tyr Asn Lys Lys Gln Val Ser Asn Gly His Glu Leu Phe Pro
        35                  40                  45

Leu Ala Val Ser Ser Lys Pro Arg Val Glu Ile His Asp Gly Asp Leu
    50                  55                  60

Arg Ser Phe Phe Thr Leu Val Met Thr Asp Pro Asp Val Pro Asn Pro
65                  70                  75                  80

Ser Asp Pro Phe Leu Lys Glu Arg Leu His Trp Leu Val Met Asn Ile
                85                  90                  95

Pro Gly Thr Thr Asp Ala Thr Phe Gly Lys Glu Val Val Ser Tyr Glu
            100                 105                 110

Leu Pro Lys Pro Asn Ile Gly Ile His Arg Tyr Val Phe Val Leu Phe
        115                 120                 125

Arg Gln Lys Gln Arg Arg Val Lys Phe Pro Ser Asn Ile Ile Ser Arg
    130                 135                 140

Asp Gln Phe Asn Thr Arg Glu Phe Ala Ile Glu Asn Asp Leu Gly Leu
145                 150                 155                 160

Pro Val Ala Ala Val Phe Phe Asn Ala Gln Arg Glu Thr Ala Ser Arg
                165                 170                 175

Arg Arg

<210> SEQ ID NO 7
<211> LENGTH: 181
<212> TYPE: PRT
<213> ORGANISM: Antirrhinum sp.

<400> SEQUENCE: 7

Met Ala Ala Lys Val Ser Ser Asp Pro Leu Val Ile Gly Arg Val Ile
1               5                   10                  15

Gly Asp Val Val Asp His Phe Thr Ser Thr Val Lys Met Ser Val Ile
            20                  25                  30

Tyr Asn Ser Asn Asn Ser Ile Lys His Val Tyr Asn Gly His Glu Leu
        35                  40                  45

Phe Pro Ser Ala Val Thr Ser Thr Pro Arg Val Glu Val His Gly Gly
    50                  55                  60

Asp Met Arg Ser Phe Phe Thr Leu Ile Met Thr Asp Pro Asp Val Pro
65                  70                  75                  80

Gly Pro Ser Asp Pro Tyr Leu Arg Glu His Leu His Trp Ile Val Thr
                85                  90                  95

Asp Ile Pro Gly Thr Thr Asp Ser Ser Phe Gly Lys Glu Val Val Ser
            100                 105                 110

Tyr Glu Met Pro Arg Pro Asn Ile Gly Ile His Arg Phe Val Phe Leu
        115                 120                 125

Leu Phe Lys Gln Lys Lys Arg Gly Gln Ala Met Leu Ser Pro Pro Val
    130                 135                 140

Val Cys Arg Asp Gly Phe Asn Thr Arg Lys Phe Thr Gln Glu Asn Glu
145                 150                 155                 160

Leu Gly Leu Pro Val Ala Ala Val Phe Phe Asn Cys Gln Arg Glu Thr
                165                 170                 175
```

Ala Ala Arg Arg Arg
            180

<210> SEQ ID NO 8
<211> LENGTH: 175
<212> TYPE: PRT
<213> ORGANISM: Nicotiana tabacum

<400> SEQUENCE: 8

Met Gly Ser Lys Met Ser Asp Pro Leu Val Ile Gly Arg Val Ile Gly
1               5                   10                  15

Glu Val Val Asp Tyr Phe Thr Pro Ser Val Lys Met Ser Val Thr Tyr
            20                  25                  30

Asn Ser Ser Lys His Val Tyr Asn Gly His Glu Leu Phe Pro Ser Ser
        35                  40                  45

Val Thr Ser Lys Pro Arg Val Glu Val His Gly Gly Asp Leu Arg Ser
    50                  55                  60

Phe Phe Thr Met Ile Met Ile Asp Pro Asp Pro Gly Pro Ser Asp
65                  70                  75                  80

Pro Tyr Leu Arg Glu His Leu His Trp Ile Val Thr Asp Ile Pro Gly
                85                  90                  95

Thr Thr Asp Cys Ser Phe Gly Lys Glu Ile Val Gly Tyr Glu Met Pro
            100                 105                 110

Arg Pro Asn Ile Gly Ile His Arg Phe Val Phe Leu Leu Phe Lys Gln
        115                 120                 125

Lys Lys Arg Gln Thr Val Leu Thr Ala Pro Leu Ser Arg Asp Arg Phe
    130                 135                 140

Asn Thr Arg Lys Phe Ala Glu Glu Asn Glu Leu Gly Ser Pro Val Ala
145                 150                 155                 160

Ala Val Phe Phe Asn Cys Gln Arg Glu Thr Ala Ala Arg Arg
                165                 170                 175

<210> SEQ ID NO 9
<211> LENGTH: 175
<212> TYPE: PRT
<213> ORGANISM: Nicotiana tabacum

<400> SEQUENCE: 9

Met Gly Ser Lys Met Ser Asp Pro Leu Val Ile Gly Arg Val Ile Gly
1               5                   10                  15

Glu Val Val Asp Tyr Phe Thr Pro Ser Val Lys Met Ser Val Thr Tyr
            20                  25                  30

Asn Ser Ser Lys His Val Tyr Asn Gly His Glu Leu Phe Pro Ser Ser
        35                  40                  45

Val Thr Ser Lys Pro Arg Val Glu Val His Gly Gly Asp Leu Arg Ser
    50                  55                  60

Phe Phe Thr Leu Ile Met Ile Asp Pro Asp Val Pro Gly Pro Ser Asp
65                  70                  75                  80

Pro Tyr Leu Arg Glu His Leu His Trp Ile Val Thr Asp Ile Pro Gly
                85                  90                  95

Thr Thr Asp Cys Ser Phe Gly Arg Glu Ile Val Gly Tyr Glu Met Pro
            100                 105                 110

Arg Pro Asn Ile Gly Ile His Arg Phe Val Phe Leu Leu Phe Lys Gln
        115                 120                 125

Lys Lys Arg Gln Thr Leu Leu Ser Ala Pro Leu Ser Arg Asp Arg Phe
    130                 135                 140

-continued

Asn Thr Arg Lys Phe Ser Glu Glu Asn Glu Leu Gly Ser Pro Val Ala
145                 150                 155                 160

Ala Ala Phe Phe Asn Cys Gln Arg Glu Thr Ala Ala Arg Arg Arg
                165                 170                 175

<210> SEQ ID NO 10
<211> LENGTH: 175
<212> TYPE: PRT
<213> ORGANISM: Lycopersicon esculentum

<400> SEQUENCE: 10

Met Ala Ser Lys Met Cys Glu Pro Leu Val Ile Gly Arg Val Ile Gly
1               5                   10                  15

Glu Val Val Asp Tyr Phe Cys Pro Ser Val Lys Met Ser Val Val Tyr
                20                  25                  30

Asn Asn Asn Lys His Val Tyr Asn Gly His Glu Phe Phe Pro Ser Ser
            35                  40                  45

Val Thr Ser Lys Pro Arg Val Glu Val His Gly Gly Asp Leu Arg Ser
    50                  55                  60

Phe Phe Thr Leu Ile Met Ile Asp Pro Asp Val Pro Gly Pro Ser Asp
65                  70                  75                  80

Pro Tyr Leu Arg Glu His Leu His Trp Ile Val Thr Asp Ile Pro Gly
                85                  90                  95

Thr Thr Asp Cys Ser Phe Gly Arg Glu Val Val Gly Tyr Glu Met Pro
                100                 105                 110

Arg Pro Asn Ile Gly Ile His Arg Phe Val Phe Leu Leu Phe Lys Gln
            115                 120                 125

Lys Lys Arg Gln Thr Ile Ser Ser Ala Pro Val Ser Arg Asp Gln Phe
130                 135                 140

Ser Ser Arg Lys Phe Ser Glu Glu Asn Glu Leu Gly Ser Pro Val Ala
145                 150                 155                 160

Ala Val Phe Phe Asn Cys Gln Arg Glu Thr Ala Ala Arg Arg Arg
                165                 170                 175

<210> SEQ ID NO 11
<211> LENGTH: 174
<212> TYPE: PRT
<213> ORGANISM: Nicotiana tabacum

<400> SEQUENCE: 11

Met Ala Ser Arg Val Val Glu Pro Leu Val Val Ala Arg Val Ile Gly
1               5                   10                  15

Glu Val Val Asp Ser Phe Asn Pro Ser Val Lys Leu Asn Val Ile Tyr
                20                  25                  30

Asn Gly Ser Lys Gln Val Phe Asn Gly His Glu Leu Met Pro Ala Val
            35                  40                  45

Ile Ala Ala Lys Pro Arg Val Glu Ile Gly Gly Glu Asp Met Arg Ser
    50                  55                  60

Ala Tyr Thr Leu Ile Met Thr Asp Pro Asp Val Pro Gly Pro Ser Asp
65                  70                  75                  80

Pro Tyr Leu Arg Glu His Leu His Trp Ile Val Thr Asp Ile Pro Gly
                85                  90                  95

Ser Thr Asp Ser Ser Phe Gly Arg Glu Ile Val Ser Tyr Glu Ser Pro
                100                 105                 110

Lys Pro Val Ile Gly Ile His Arg Tyr Val Leu Leu Leu Tyr Lys Gln
            115                 120                 125

Ser Gly Arg Gln Thr Val Lys Pro Ala Ala Thr Arg Asp His Phe Asn
            130                 135                 140

Thr Arg Arg Tyr Thr Ala Glu Asn Gly Leu Gly Ser Pro Val Ala Ala
145                 150                 155                 160

Val Tyr Phe Asn Ala Gln Arg Glu Thr Ala Ala Arg Arg Arg
                165                 170

<210> SEQ ID NO 12
<211> LENGTH: 173
<212> TYPE: PRT
<213> ORGANISM: Oryza sativa

<400> SEQUENCE: 12

Met Ser Arg Ser Val Glu Pro Leu Val Val Gly Arg Val Ile Gly Glu
1               5                   10                  15

Val Leu Asp Thr Phe Asn Pro Cys Met Lys Met Ile Val Thr Tyr Asn
            20                  25                  30

Ser Asn Lys Leu Val Phe Asn Gly His Glu Leu Tyr Pro Ser Ala Val
        35                  40                  45

Val Ser Lys Pro Arg Val Glu Val Gln Gly Gly Asp Leu Arg Ser Phe
    50                  55                  60

Phe Thr Leu Val Met Thr Asp Pro Asp Val Pro Gly Pro Ser Asp Pro
65                  70                  75                  80

Tyr Leu Arg Glu His Leu His Trp Ile Val Thr Asp Ile Pro Gly Thr
                85                  90                  95

Thr Asp Ala Ser Phe Gly Arg Glu Val Ile Ser Tyr Glu Ser Pro Lys
            100                 105                 110

Pro Asn Ile Gly Ile His Arg Phe Ile Phe Val Leu Phe Lys Gln Lys
        115                 120                 125

Arg Arg Gln Thr Val Ile Val Pro Ser Phe Arg Asp His Phe Asn Thr
    130                 135                 140

Arg Arg Phe Ala Glu Glu Asn Asp Leu Gly Leu Pro Val Ala Ala Val
145                 150                 155                 160

Tyr Phe Asn Ala Gln Arg Glu Thr Ala Ala Arg Arg Arg
                165                 170

<210> SEQ ID NO 13
<211> LENGTH: 173
<212> TYPE: PRT
<213> ORGANISM: Oryza sativa

<400> SEQUENCE: 13

Met Ser Arg Ser Val Glu Pro Leu Val Val Gly Arg Val Ile Gly Glu
1               5                   10                  15

Val Ile Asp Ser Phe Asn Pro Cys Thr Lys Met Ile Val Thr Tyr Asn
            20                  25                  30

Ser Asn Lys Leu Val Phe Asn Gly His Glu Phe Tyr Pro Ser Ala Val
        35                  40                  45

Val Ser Lys Pro Arg Val Glu Val Gln Gly Gly Asp Met Arg Ser Phe
    50                  55                  60

Phe Thr Leu Val Met Thr Asp Pro Asp Val Pro Gly Pro Ser Asp Pro
65                  70                  75                  80

Tyr Leu Arg Glu His Leu His Trp Ile Val Thr Asp Ile Pro Gly Thr
                85                  90                  95

Thr Asp Ala Ser Phe Gly Arg Glu Ile Ile Ser Tyr Glu Ser Pro Lys
            100                 105                 110

```
Pro Ser Ile Gly Ile His Arg Phe Val Phe Val Leu Phe Lys Gln Lys
        115                 120                 125

Arg Arg Gln Ala Val Val Pro Ser Ser Arg Asp His Phe Asn Thr
130                 135                 140

Arg Gln Phe Ala Glu Glu Asn Glu Leu Gly Leu Pro Val Ala Ala Val
145                 150                 155                 160

Tyr Phe Asn Ala Gln Arg Glu Thr Ala Ala Arg Arg Arg
                165                 170

<210> SEQ ID NO 14
<211> LENGTH: 175
<212> TYPE: PRT
<213> ORGANISM: Arabidopsis sp.

<400> SEQUENCE: 14

Met Ser Ile Asn Ile Arg Asp Pro Leu Ile Val Ser Arg Val Val Gly
1               5                   10                  15

Asp Val Leu Asp Pro Phe Asn Arg Ser Ile Thr Leu Lys Val Thr Tyr
            20                  25                  30

Gly Gln Arg Glu Val Thr Asn Gly Leu Asp Leu Arg Pro Ser Gln Val
        35                  40                  45

Gln Asn Lys Pro Arg Val Glu Ile Gly Gly Glu Asp Leu Arg Asn Phe
    50                  55                  60

Tyr Thr Leu Val Met Val Asp Pro Asp Val Pro Ser Pro Ser Asn Pro
65                  70                  75                  80

His Leu Arg Glu Tyr Leu His Trp Leu Val Thr Asp Ile Pro Ala Thr
                85                  90                  95

Thr Gly Thr Thr Phe Gly Asn Glu Ile Val Cys Tyr Glu Asn Pro Ser
            100                 105                 110

Pro Thr Ala Gly Ile His Arg Val Val Phe Ile Leu Phe Arg Gln Leu
        115                 120                 125

Gly Arg Gln Thr Val Tyr Ala Pro Gly Trp Arg Gln Asn Phe Asn Thr
    130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175

<210> SEQ ID NO 15
<211> LENGTH: 22
<212> TYPE: DNA
<213> ORGANISM: Artificial Sequence
<220> FEATURE:
<223> OTHER INFORMATION: Synthetic primer

<400> SEQUENCE: 15
ggttatgaca gacccagatg tg                                          22

<210> SEQ ID NO 16
<211> LENGTH: 20
<212> TYPE: DNA
<213> ORGANISM: Artificial Sequence
<220> FEATURE:
<223> OTHER INFORMATION: Synthetic primer

<400> SEQUENCE: 16
cgaacctgtg gataccaatg                                             20

<210> SEQ ID NO 17
```

<211> LENGTH: 20
<212> TYPE: DNA
<213> ORGANISM: Artificial Sequence
<220> FEATURE:
<223> OTHER INFORMATION: Synthetic primer

<400> SEQUENCE: 17
cacattggtt atgacggacc                                              20

<210> SEQ ID NO 18
<211> LENGTH: 18
<212> TYPE: DNA
<213> ORGANISM: Artificial Sequence
<220> FEATURE:
<223> OTHER INFORMATION: Synthetic primer

<400> SEQUENCE: 18
ctccccccca aatgaagc                                                18

<210> SEQ ID NO 19
<211> LENGTH: 18
<212> TYPE: DNA
<213> ORGANISM: Artificial Sequence
<220> FEATURE:
<223> OTHER INFORMATION: Synthetic primer

<400> SEQUENCE: 19
caaggactgg agaggtgg                                                18

<210> SEQ ID NO 20
<211> LENGTH: 18
<212> TYPE: DNA
<213> ORGANISM: Artificial Sequence
<220> FEATURE:
<223> OTHER INFORMATION: Synthetic primer

<400> SEQUENCE: 20
ttgactcgtt gtcgtacc                                                18

<210> SEQ ID NO 21
<211> LENGTH: 26
<212> TYPE: DNA
<213> ORGANISM: Artificial Sequence
<220> FEATURE:
<223> OTHER INFORMATION: Synthetic primer

<400> SEQUENCE: 21
ggatccccat gtctaggtct gtggag                                       26

<210> SEQ ID NO 22
<211> LENGTH: 24
<212> TYPE: DNA
<213> ORGANISM: Artificial Sequence
<220> FEATURE:
<223> OTHER INFORMATION: Synthetic primer

<400> SEQUENCE: 22
gggatcccac aactgggata gcca                                         24

<210> SEQ ID NO 23
<211> LENGTH: 22
<212> TYPE: DNA
<213> ORGANISM: Artificial Sequence
<220> FEATURE:
<223> OTHER INFORMATION: Synthetic primer

<400> SEQUENCE: 23

```
atgtctaggt ctgtggagcc tc                                          22
```

<210> SEQ ID NO 24
<211> LENGTH: 21
<212> TYPE: DNA
<213> ORGANISM: Artificial Sequence
<220> FEATURE:
<223> OTHER INFORMATION: Synthetic primer

<400> SEQUENCE: 24

```
accggcaaca ggattcaatc t                                           21
```

<210> SEQ ID NO 25
<211> LENGTH: 18
<212> TYPE: DNA
<213> ORGANISM: Artificial Sequence
<220> FEATURE:
<223> OTHER INFORMATION: Synthetic primer

<400> SEQUENCE: 25

```
cgtggcggag cggcagac                                               18
```

<210> SEQ ID NO 26
<211> LENGTH: 24
<212> TYPE: DNA
<213> ORGANISM: Artificial Sequence
<220> FEATURE:
<223> OTHER INFORMATION: Synthetic primer

<400> SEQUENCE: 26

```
tagtacatcc atttagggtt tagg                                        24
```

<210> SEQ ID NO 27
<211> LENGTH: 20
<212> TYPE: DNA
<213> ORGANISM: Artificial Sequence
<220> FEATURE:
<223> OTHER INFORMATION: Synthetic primer

<400> SEQUENCE: 27

```
tatttatttg cttggtactg                                             20
```

<210> SEQ ID NO 28
<211> LENGTH: 20
<212> TYPE: DNA
<213> ORGANISM: Artificial Sequence
<220> FEATURE:
<223> OTHER INFORMATION: Synthetic primer

<400> SEQUENCE: 28

```
cgaacctgtg gataccaatg                                             20
```

<210> SEQ ID NO 29
<211> LENGTH: 30
<212> TYPE: DNA
<213> ORGANISM: Artificial Sequence
<220> FEATURE:
<223> OTHER INFORMATION: Synthetic primer

<400> SEQUENCE: 29

```
gggatcccac aactgggata gccaagaact                                  30
```

<210> SEQ ID NO 30
<211> LENGTH: 5
<212> TYPE: PRT

```
-continued

<213> ORGANISM: Artificial Sequence
<220> FEATURE:
<223> OTHER INFORMATION: Synthetic peptide

<400> SEQUENCE: 30

Tyr Glu Ser Pro Lys
1               5

<210> SEQ ID NO 31
<211> LENGTH: 5
<212> TYPE: PRT
<213> ORGANISM: Artificial Sequence
<220> FEATURE:
<223> OTHER INFORMATION: Synthetic peptide

<400> SEQUENCE: 31

Tyr Glu Ser Pro Arg
1               5
```